United States Patent [19]

Shimada et al.

[11] Patent Number: 5,462,826
[45] Date of Patent: * Oct. 31, 1995

[54] CHARGE TRANSPORTING MATERIALS AND ELECTROPHOTOGRAPHIC PHOTOCONDUCTORS USING THE SAME

[75] Inventors: Tomoyuki Shimada, Numazu; Masaomi Sasaki, Susono; Mitsuru Hashimoto; Tamotsu Aruga, both of Numazu, all of Japan

[73] Assignee: Ricoh Company, Ltd., Tokyo, Japan

[*] Notice: The portion of the term of this patent subsequent to Jun. 15, 2010, has been disclaimed.

[21] Appl. No.: 197,854

[22] Filed: Feb. 17, 1994

Related U.S. Application Data

[62] Division of Ser. No. 77,968, Jun. 18, 1993, Pat. No. 5,298,661, which is a continuation of Ser. No. 817,975, Jan. 8, 1992, abandoned, which is a continuation of Ser. No. 442,533, Nov. 28, 1989, abandoned, which is a continuation-in-part of Ser. No. 260,063, Oct. 20, 1988, Pat. No. 4,898,800.

[30] Foreign Application Priority Data

Jan. 27, 1989 [JP] Japan ..................... 1-18698
Jan. 27, 1989 [JP] Japan ..................... 1-18699

[51] Int. Cl.$^6$ ..................... G03G 5/04
[52] U.S. Cl. ..................... 430/59; 430/64; 430/73
[58] Field of Search ..................... 430/59, 58, 73, 430/64

[56] References Cited

U.S. PATENT DOCUMENTS

| | | | |
|---|---|---|---|
| 4,898,800 | 2/1990 | Shimada et al. | 430/59 |
| 4,937,165 | 6/1990 | Ong et al. | 430/59 |
| 5,202,207 | 4/1993 | Kanemaru et al. | 430/59 |
| 5,219,692 | 6/1993 | Shimada et al. | 430/59 |

*Primary Examiner*—John Goodrow
*Attorney, Agent, or Firm*—Oblon, Spivak, McClelland, Maier & Neustadt

[57] ABSTRACT

Charge transporting materials having general formula (I):

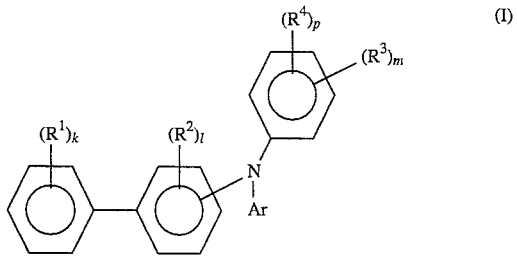

wherein $R^1$ represents hydrogen; an unsubstituted or substituted alkyl group; an alkoxyl group having 1 to 4 carbon atoms; a thioalkoxyl group having 1 to 4 carbon atoms; an aryloxy group; an aralkyl group; a nitro group; an unsubstituted or substituted aryl group; a halogen; an amino group; an unsubstituted or substituted dialkylamino group; $R^2$ represents hydrogen; an unsubstituted or substituted alkyl group; an alkoxyl group having 1 to 4 carbon atoms; or a halogen; $R^3$ represents hydrogen; an alkyl group having 1 to 4 carbon atoms; an alkoxyl group having 1 to 4 carbon atoms; a halogen; a dialkylamino group; an amino group; a thioalkoxyl group having 1 to 4 carbon atoms; an aryloxy group; a methylenedioxy group; an aralkyl group; or an unsubstituted or substituted aryl group; $R^4$ represents hydrogen; an alkoxyl group; or a halogen; Ar represents an unsubstituted or substituted monocyclic hydrocarbon group, non-condensed polycyclic hydrocarbon group or heterocyclic group; k is an integer of 0 to 5, l is an integer of 0 to 4, and (p+m) is 0 to 5, provided that when Ar is an unsubstituted phenyl group, $R^1$, $R^2$, $R^3$, and $R^4$ cannot be hydrogen at the same time.

41 Claims, 14 Drawing Sheets

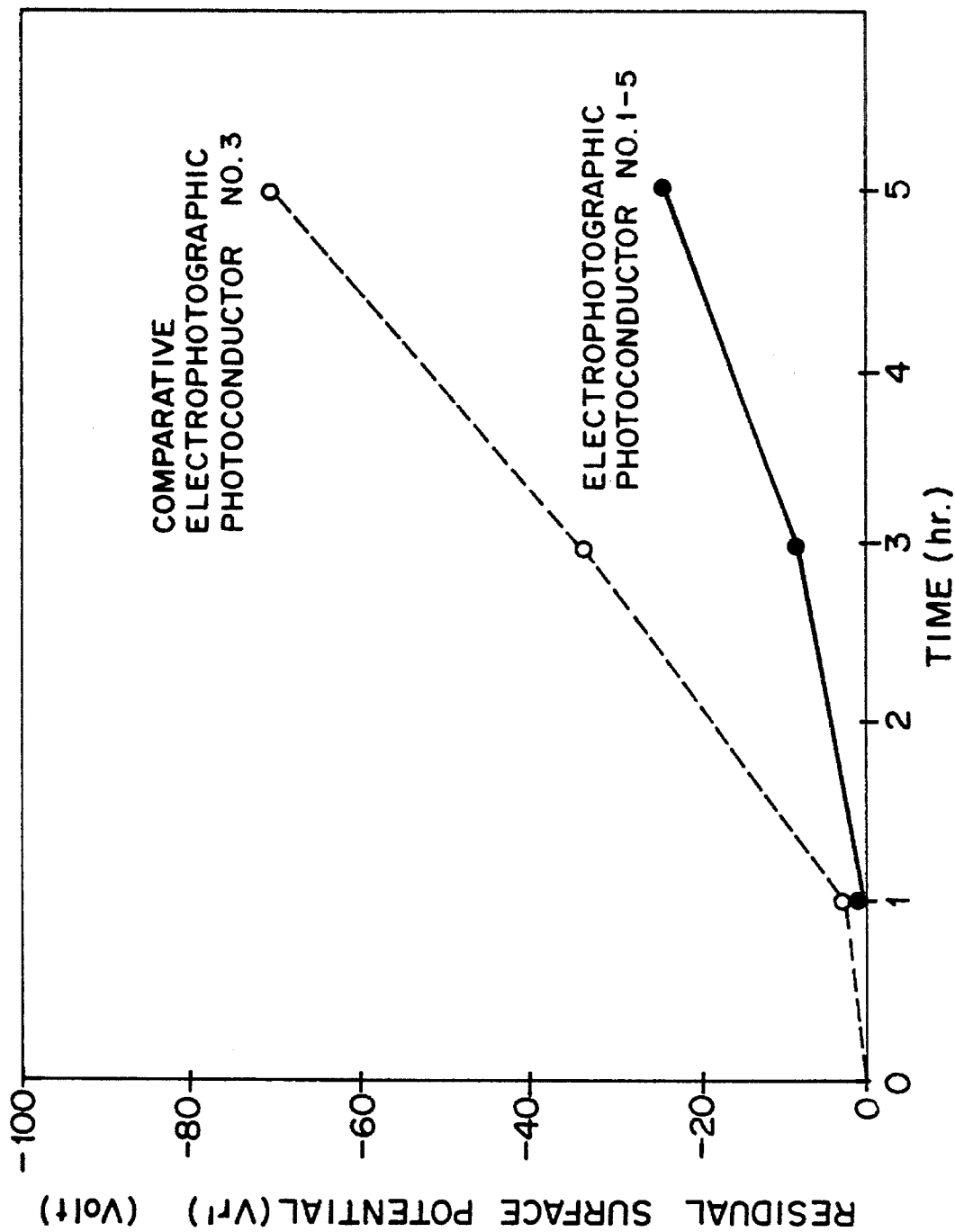

CHARGE TRANSPORTING MATERIALS AND ELECTROPHOTOGRAPHIC PHOTOCONDUCTORS USING THE SAME

This is a division of application Ser. No. 08/077,968, filed on Jun. 18, 1993, now U.S. Pat. No. 5,298,661 which is a continuation of application Ser. No. 07/817,975, filed on Jan. 8, 1992 now abandoned, which is a continuation of application Ser. No. 07/442,533, filed on Nov. 28, 1989 now abandoned, which is a Continuation-in-Part of application Ser. No. 07/260,063, filed on Oct. 20, 1988, now U.S. Pat. No. 4,898,800.

BACKGROUND OF THE INVENTION

The present invention relates to charge transporting materials and electrophotographic photoconductors using the same, and more particularly, novel aminobiphenyl compounds used as the charge transporting materials, and electrophotographic photoconductors comprising any of the aminobiphenyl compounds as an organic photoconductive material or charge transporting material.

Conventionally a variety of inorganic and organic electrophotographic photoconductors are known. As inorganic photoconductors for use in electrophotography, there are known types in which the photoconductive materials, for instance, selenium, cadmium sulfide, and zinc oxide.

In an electrophotographic process, a photoconductor is first exposed to corona charges in the dark, so that the surface of the photoconductor is electrically charged uniformly to a predetermined polarity. The thus uniformly charged photoconductor is then exposed to original light images and the portions exposed to the original light images selectively become electroconductive so that electric charges dissipate from the exposed portions of the photoconductor, whereby latent electrostatic images corresponding to the original light images are formed on the surface of the photoconductor. The latent electrostatic images are then developed by the so-called toner which comprises a colorant, such as a dye or a pigment, and a binder agent made, for instance, of a polymeric material; thus, visible developed images can be obtained on the photoconductor. It is necessary that the photoconductors for use in electrophotography have at least the following fundamental properties: (1) chargeability to a predetermined potential in the dark; (2) minimum electric charge dissipation in the dark; and (3) quick dissipation of electric charges upon exposure to light.

While the above-mentioned inorganic electrophotographic photoconductors have many advantages over other conventional electrophotographic photoconductors, at the same time they have several shortcomings from the viewpoint of practical use.

For instance, a selenium photoconductor, which is widely used at present and sufficiently meets the above-mentioned requirements (1) to (3), has the shortcoming that its production is difficult and, accordingly, its production cost is high. Further, it is difficult to work it into the form of a belt flue to its poor flexibility, and it is so vulnerable no bean and mechanical shocks that it must be handled with the utmost care.

Cadmium sulfide photoconductors and zinc oxide photoconductors are prepared by dispersing cadmium sulfide or zinc oxide in a binder resin. They can be produced inexpensively compared with selenium photoconductors and are also used commonly in practice. However, the cadmium sulfide and zinc oxide photoconductors are poor in surface smoothness, hardness, tensile strength and wear resistance. Therefore, they are not suitable as photoconductors for use in plain paper copiers in which the photoconductors are used in quick repetition.

Recently, organic electrophotographic photoconductors, which are said not to have such shortcomings of the inorganic electrophotographic photoconductors, have been proposed, and some of them are in fact used in practice.

Representative examples of such organic electrophotographic photoconductors are an electrophotographic photoconductor comprising poly-N-vinylcarbazole and 2,4,7-trinitrofluorenon-9-one (U.S. Pat. No. 3,484,237), an electrophotographic photoconductor comprising poly-N-vinylcarbazole which is sensitized by a pyrylium salt type dye (Japanese Patent Publication 48-25658), photoconductors containing as the main component organic pigments (Japanese Laid-Open Patent Application 47-37543), a photoconductor comprising as the main component an eutectic crystalline complex consisting of a dye and a resin (Japanese Laid-Open Patent Application 47-10735), a photoconductor comprising a triphenylamine compound which is sensitized by a dye (U.S. Pat. No. 3,180,730), and a photoconductor comprising as charge transporting materials poly-N-vinylcarbazole and an amide derivative (Japanese Laid-Open Patent Application 58-1155).

Although the above-mentioned organic electrophotographic photoconductors have various advantages over other conventional electrophotographic photoconductors, they do not meet various requirements in view of the practical use thereof.

Furthermore, polyfunctional tertiary amine compounds, in particular, aminobiphenyl derivatives (or benzidine derivatives), are known as excellent photoconductive materials for use in electrophotographic photoconductors, as disclosed in U.S. Pat. No. 3,265,496, Japanese Patent Publication 39-11546, and Japanese Laid-Open Patent Application 53-27033. These compounds, however, have the shortcoming that they are so slightly soluble in adhesive resins that they tend to be crystallized in a photoconductive layer of an electrophotographic photoconductor. In order to eliminate this shortcoming, it is tried to use the above compounds in combination with low-molecular weight compounds for minimizing the crystallization of the amine compounds as disclosed in Japanese Laid-Open Patent Application 62-11216.

In addition to the above aminobiphenyl compounds, N,N-diphenyl-[1,1-biphenyl]-4-amine (Helv. Chim. Acta. 6 1011P, 1923), N,N-bis(4-methoxyphenyl)-[1,1'-biphenyl-4-amine, N,N-bis([1,1'-biphenyl]-4-yl)-[1,1'-biphenyl]-4-amine and N-[1,1'-biphenyl]-4-yl-N-(4-methoxyphenyl)-[1, 1'-biphenyl] -4-amine (J. Prakt. Chem. 317 (2) 284P, 1975) are known. These compounds, however, are not useful as organic photoconductive materials for electrophotography.

Furthermore, Japanese Laid-Open Patent Application 57-195254 discloses N,N-diphenyl[1,1'-biphenyl]-4-amine as a carrier transporting material for use in an electrophotographic photoconductor. However, the electrophotographic photoconductor using the above compound has the shortcomings that the-residual potential thereof is built up while in repeated use thereof and accordingly the obtained image quality is degraded while in use, with the production unclear images.

Japanese Laid-Open Patent Application 62-201447 discloses carrier transporting materials such as 4-dimethylamino-4'-diphenylaminobiphenyl and 4-diethylamino-4'-di(m-tolylamino)-biphenyl. The electrophotographic photoconductors using these compounds, however, have the shortcomings that the chargeability thereof decreases while in repeated use and accordingly the obtained images become unclear.

SUMMARY OF THE INVENTION

It is therefore a first object of the present invention to provide charge transporting materials for use in an electrophotographic photoconductor, which charge transporting materials, when used in electrophotographic photoconductors, are capable of providing electrophotographic photoconductors which are excellent in electrostatic durability, in particular, capable of maintaining a minimum residual potential even when used in repetition, and are inexpensive.

A second object of the present invention is to provide electrophotographic photoconductors comprising the above charge transporting materials, which are excellent in electrostatic durability, in particular, in the maintenance of a minimum residual potential thereof even when used in repetition, and are inexpensive.

A third object of the present invention is to provide aminobiphenyl compounds, which can be used as the abovementioned charge transporting materials.

The first and second objects of the present invention are respectively attained by using the following biphenylamino compounds as the charge transporting material, and by an electrophotographic photoconductor comprising an electroconductive support and a photoconductive layer formed thereon comprising as an effective component at least one aminobiphenyl compound of formula (I)

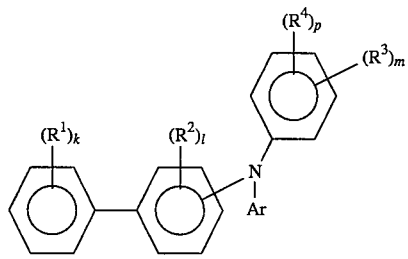

wherein $R^1$ represents hydrogen; an unsubstituted or substituted alkyl group such as an alkyl group having 1 to 4 carbon atoms; an alkoxyl group having 1 to 4 carbon atoms; a thioalkoxyl group having 1 to 4 carbon atoms; an aryloxy group such as a phenoxy group and a naphthoxy group; a methylenedioxy group; an aralkyl group such as $C_6H_5(CH_2)_n$— where n is 1 to 4; a nitro group; an unsubstituted or substituted aryl group such as a phenyl group and a naphthyl group, which may have a substituent such as an alkyl group having 1 to 4 carbon atoms, and an alkoxyl group having 1 to 4 carbon atoms; a halogen; an amino group; an unsubstitued or substituted dialkylamino group; $R^2$ represents hydrogen; an unsubstituted or substituted alkyl group such as an alkyl group having 1 to 4 carbon atoms; an alkoxyl group having 1 to 4 carbon atoms: or a halogen; $R^3$ represents hydrogen; an alkyl group having 1 to 4 carbon atoms; an alkoxyl group having 1 to 4 carbon atoms; a halogen; a dialkylamino group; an amino group; a thioalkoxyl group having 1 to 4 carbon atoms; an aryloxy group such as a phenoxy group and a naphthoxy group; a methylenedioxy group; an aralkyl group such as $C_6H_5(CH_2)_n$—, where n is 1 to 4; or an unsubstituted or substituted aryl group such as a phenyl group and a naphthyl group, which may have a substituent such as an amino group, an unsubstituted or substituted dialkylamino group, an alkoxyl group, a thioalkyl group, an aryloxy group, an unsubstituted or substituted alkyl group such as an alkyl group having 1 to 4 carbon atoms, an alkoxyl group having 1 to 4 carbon atoms, and a halogen; $R^4$ represents hydrogen; an alkoxyl group such as an alkoxyl group having 1 to 4 carbon atoms, an unsubstituted or substituted alkyl group such as an alkyl group having 1 to 4 carbon atoms; or a halogen; Ar represents an unsubstituted or substituted monocyclic hydrocarbon group, non-condensed polycyclic hydrocarbon group or heterocyclic group, which includes

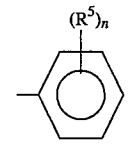

wherein $R^5$ represents hydrogen; an unsubstituted or substituted alkyl group such as an alkyl group having 1 to 4 carbon atoms; an alkoxyl group having 1 to 4 carbon atoms; a thioalkoxyl group having 1 to 4 carbon atoms; an aryloxy group such as a phenoxy group and a naphthoxy group; a methylenedioxy group; an aralkyl group such as $C_6H_5(CH_2)_n$— where n is 1 to 4; a nitro group; an unsubstituted or substituted aryl group such as a phenyl group and a naphthyl group, which may have a substituent such as an alkyl group having 1 to 4 carbon atoms, an alkoxyl group having 1 to 4 carbon atoms; a halogen; an amino group; or an unsubstituted or substituted dialkylamino group, k is an integer of 0 to 5, l is an integer of 0 to 4, and (p+m) is 0 to 5, provided that when Ar is an unsubstituted phenyl group, $R^1$, $R^2$, $R^3$, and $R^4$ cannot be hydrogen at the same time, namely $R^1$, $R^2$, $R^3$ and $R^5$ cannot be hydrogen at the same time.

In the above formula (I), when ($R^4$) is hydrogen, and Ar is

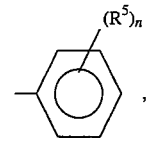

$R^1$, $R^2$, $R^3$ and $R^5$ may each represent hydrogen, an alkyl group having 1 to 4 carbon atoms, or an alkoxyl group having 1 to 4 carbon atoms, k, m and n may each represent an integer of 0 to 5, and l may represent and integer of 0 to 4, provided that $R^1$, $R^2$, $R^3$ and $R^5$ cannot be hydrogen at the same time, which provides preferable charge transporting materials for use in the present invention.

The third object of the present invention is attained by the aminobiphenyl compounds of formula (I'):

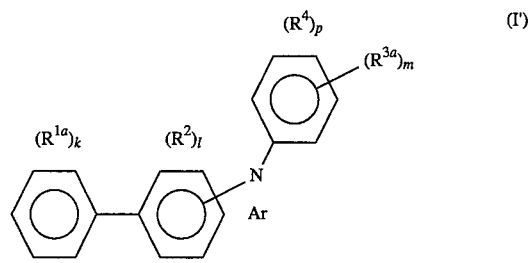

wherein $R^{1a}$ represents hydrogen; an unsubstituted or substituted alkyl group such as an alkyl group having 1 to 4 carbon atoms; an alkoxyl group having 1 to 4 carbon atoms; a thioalkoxyl group having 1 to 4 carbon atoms; an aryloxy group such as a phenoxy group and a naphthoxy group; a methylenedioxy group; an aralkyl group such as $C_6H_5(CH_2)_n$— where n is 1 to 4; a nitro group; an unsubstituted or substituted aryl group such as alphenyl group and a naphthyl group, which may have a substituent such as an alkyl group having 1 to 4 carbon atoms, an alkoxyl group having 1 to 4 carbon atoms; a halogen; an unsubstitued or substituted dialkylamino group; $R^2$ represents hydrogen; an unsubstituted or substituted alkyl group such as an alkyl group having 1 to 4 carbon atoms; an alkoxyl group having 1 to 4 carbon atoms, or a halogen; $R^{3a}$ represents hydrogen; an alkyl group having 1 to 4 carbon atoms; an alkoxyl group having 1 to 4 carbon atoms; a halogen; a dialkylamino group; an amino group; a thioalkoxyl group having 1 to 4 carbon atoms; an aryloxy group such as a phenoxy :group and a naphthoxy group; a methylenedioxy group; an aralkyl group such as $C_6H_5(CH_2)_n$—, where n is 1 to 4; or an unsubstituted or substituted aryl group such as a phenyl group and a naphthyl group, which may have a substituent such as an unsubstituted or substituted dialkylamino group, an alkoxyl group, a thioalkyl group, an aryloxy group, an unsubstituted or substituted alkyl group such as an alkyl group having 1 to 4 carbon atoms, an alkoxyl group having 1 to 4 carbon atoms, and a halogen; $R^4$ represents hydrogen; an alkoxyl group such as an alkoxyl group having 1 to 4 carbon atoms, an unsubstituted or substituted alkyl group such as an alkyl group having 1 to 4 carbon atoms, or a halogen; Ar represents an unsubstituted or substituted monocyclic hydrocarbon group, non-condensed polycyclic hydrocarbon group or heterocyclic group, which includes

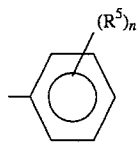

wherein $R^5$ represents hydrogen; an unsubstituted or substituted alkyl group such as an alkyl group having 1 to 4 carbon atoms; an alkoxyl group having 1 to 4 carbon atoms; a thioalkoxyl group having 1 to 4 carbon atoms; an aryloxy group such as a phenoxy group and a naphthoxy group; a methylenedioxy group; an aralkyl group such as $C_6H_5(CH_2)_n$— where n is 1 to 4; a nitro group; an unsubstituted or substituted aryl group such as a phenyl group and a naphthyl group, which may have a substituent such as an alkyl group having 1 to 4 carbon atoms, an alkoxyl group having 1 to 4 carbon atoms; a halogen; an unsubstitued or substituted dialkylamino group, k is an integer of 0 to 5, l is an integer of 0 to 4, and (p+m) is 0 to 5, provided that $R^{1a}$, $R^2$, $R^{3a}$ and $R^5$ cannot be hydrogen at the same time.

BRIEF DESCRIPTION OF THE DRAWINGS

In the drawings,

FIG. 18 is a graph showing the residual surface potentials (Vr') of Comparative Electrophotographic Photoconductor No. 1-1 and Electrophotographic Photoconductor No. 1-5 according to the present invention for comparison.

DETAILED DESCRIPTION OF THE PREFERRED EMBODIMENTS

Figure 1:
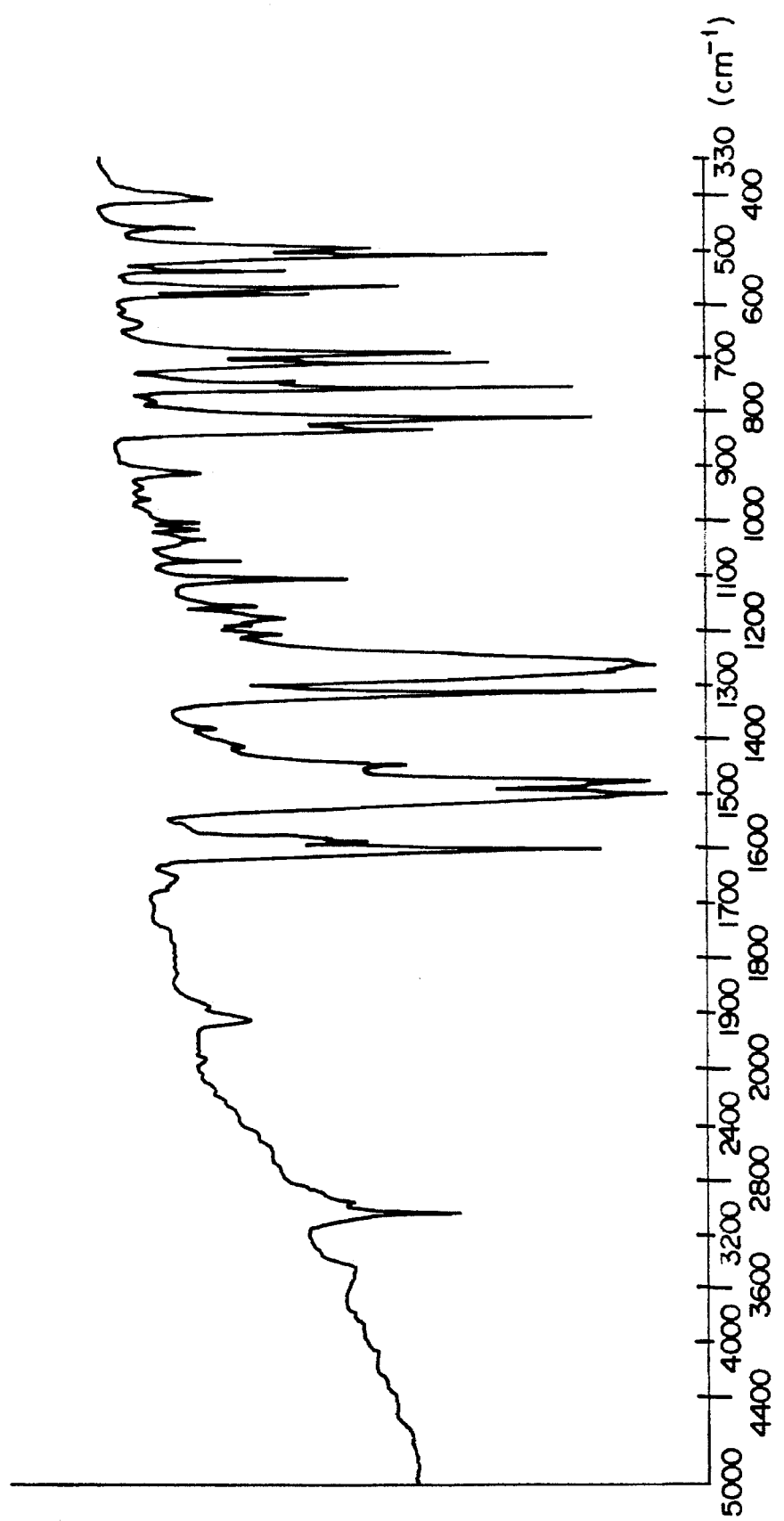
FIG. 1 is an infrared spectrum of an aminobiphenyl compound No 1-2 for use in the present invention.
Figure 2:
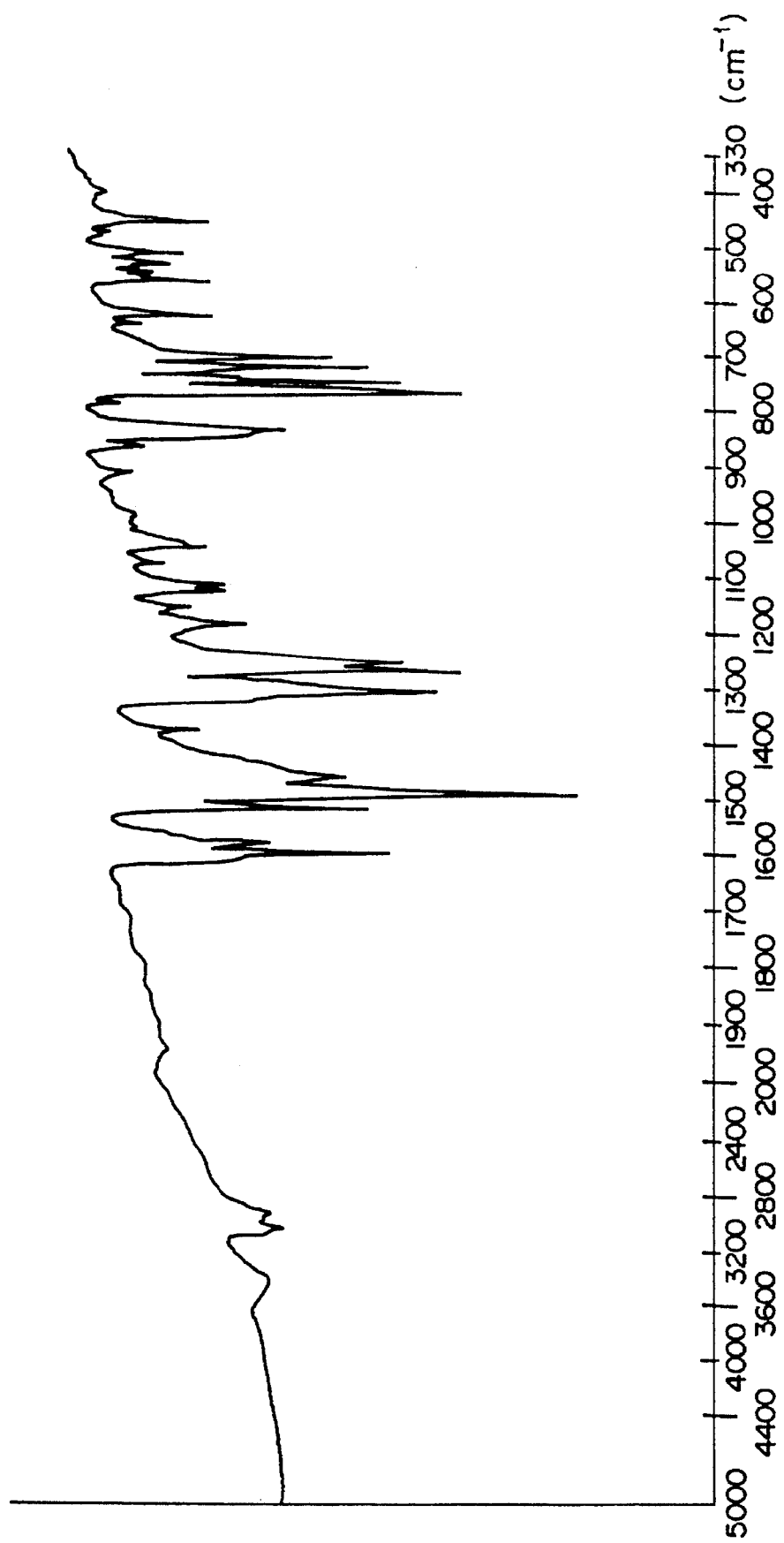
FIG. 2 is an infrared spectrum of an aminobiphneyl compound No. 1-4 for use in the present invention.
Figure 3:
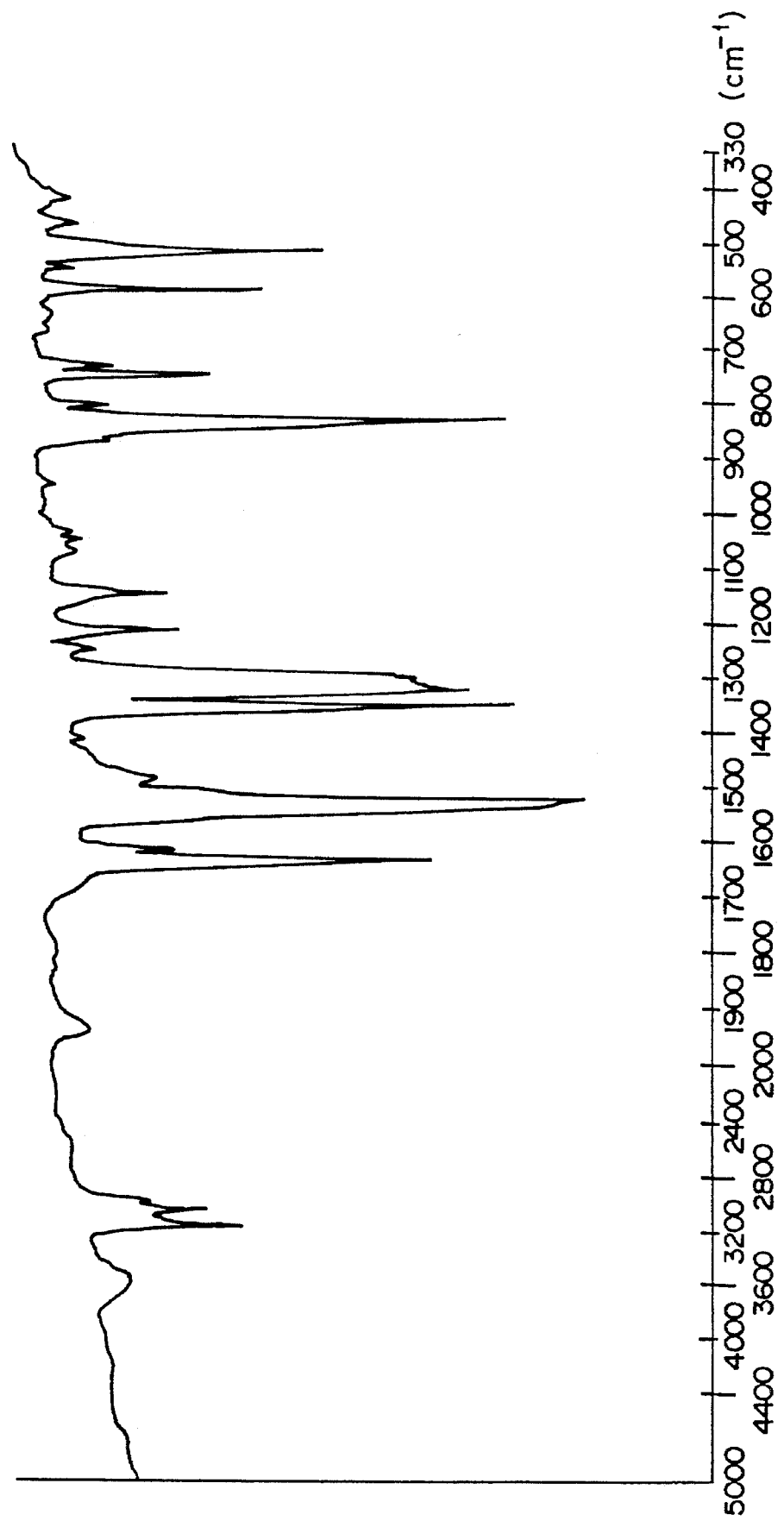
FIG. 3 is an infrared spectrum of an aminobiphneyl compound No. 1-21 for use in the present invention.
Figure 4:
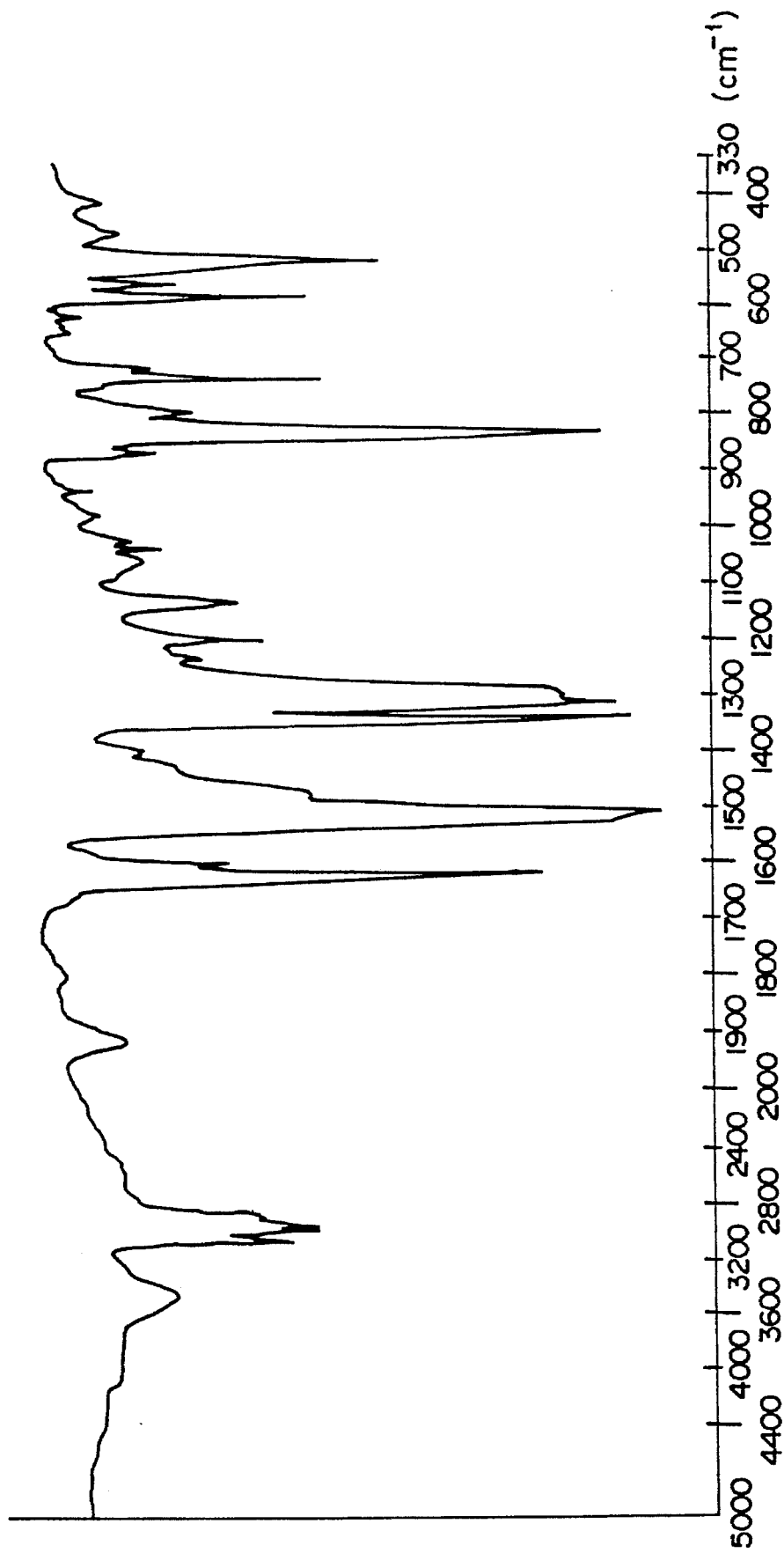
FIG. 4 is an infrared spectrum of an aminobiphenyl compound No. 1-35 for use in the present invention.
Figure 5:
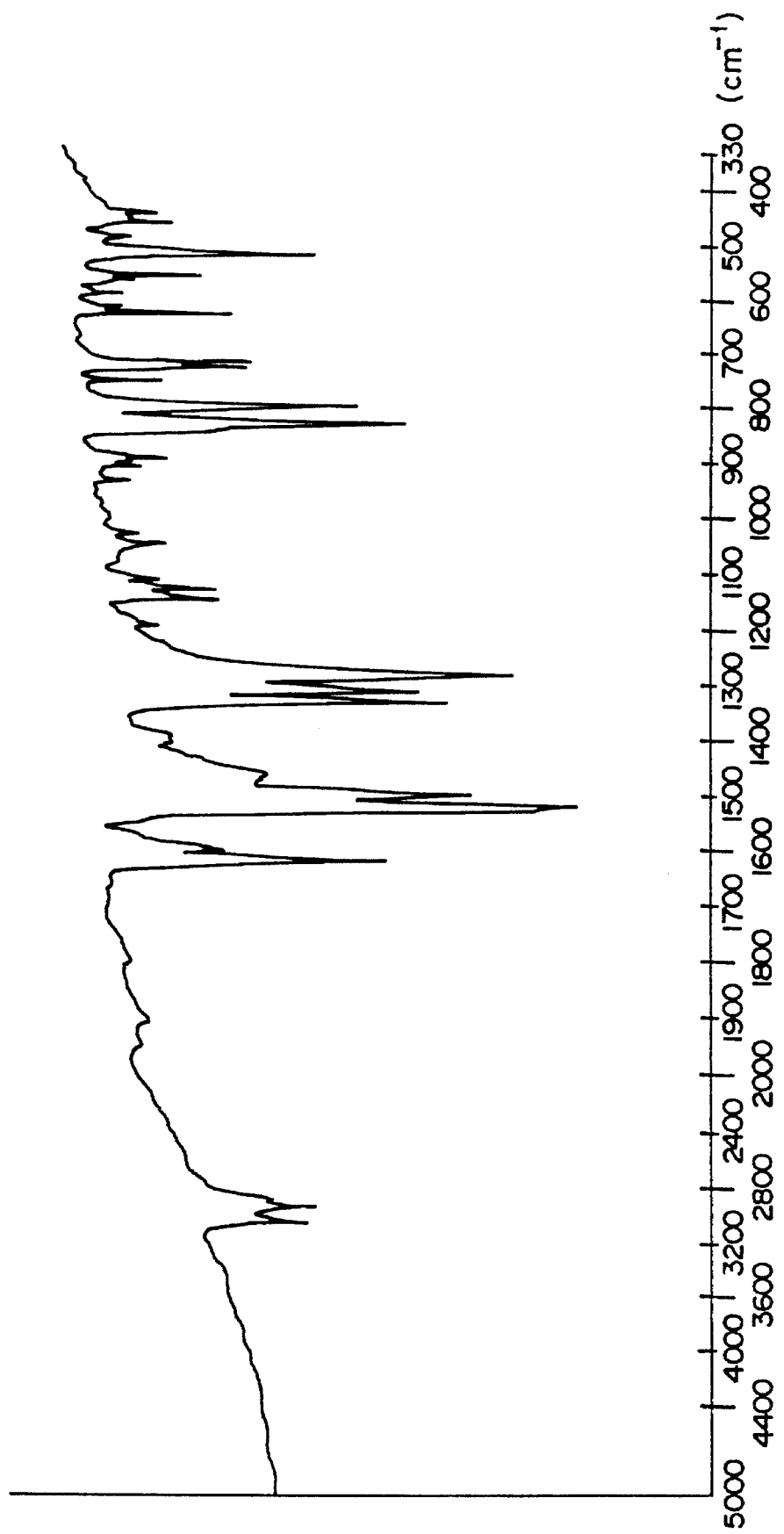
FIG. 5 is an infrared spectrum of an aminobiphenyl compound No. 1-43 for use in the present invention.
Figure 6:
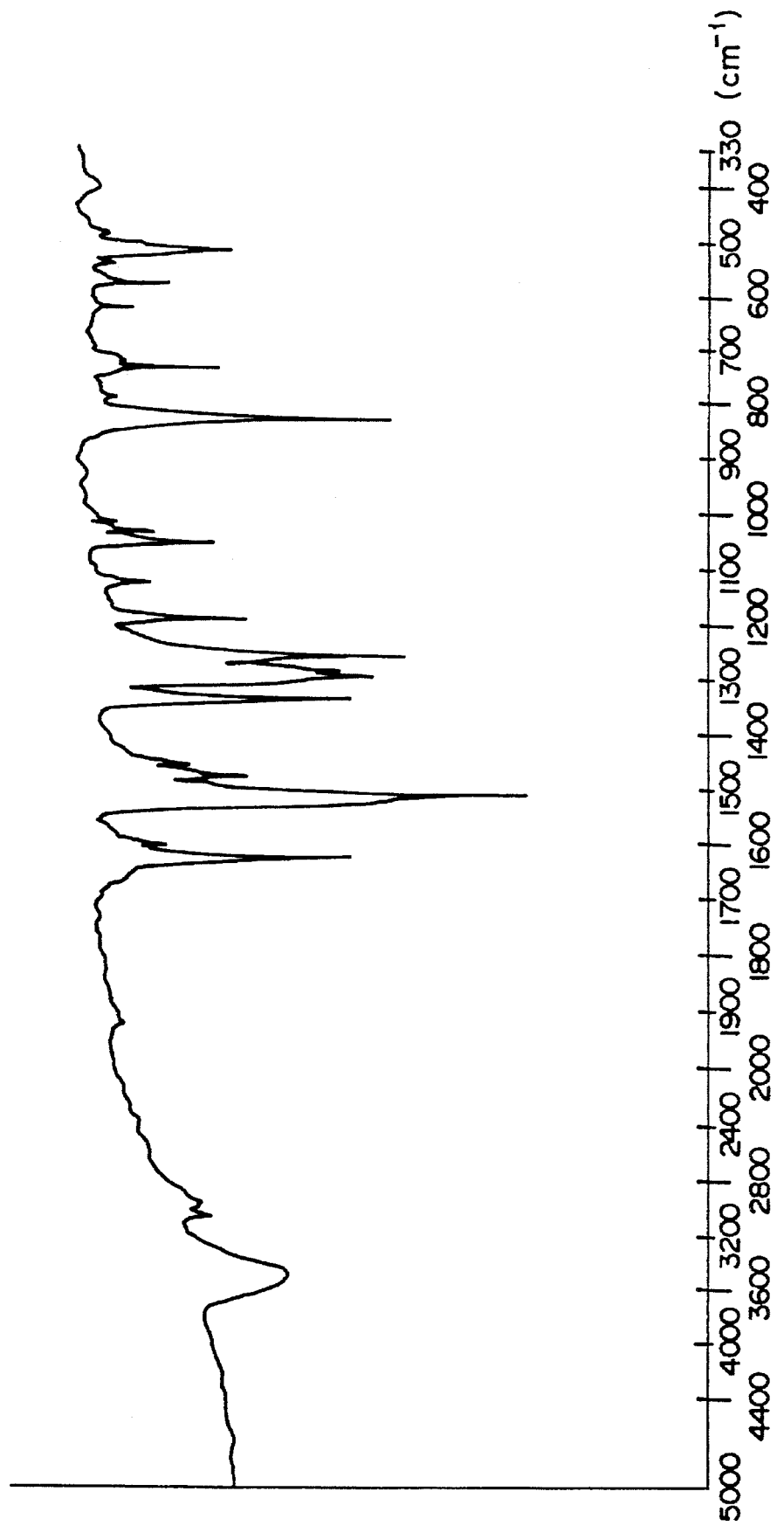
FIG. 6 is an infrared spectrum of an aminobiphenyl compound No. 1-67 for use in the present invention.
Figure 7:
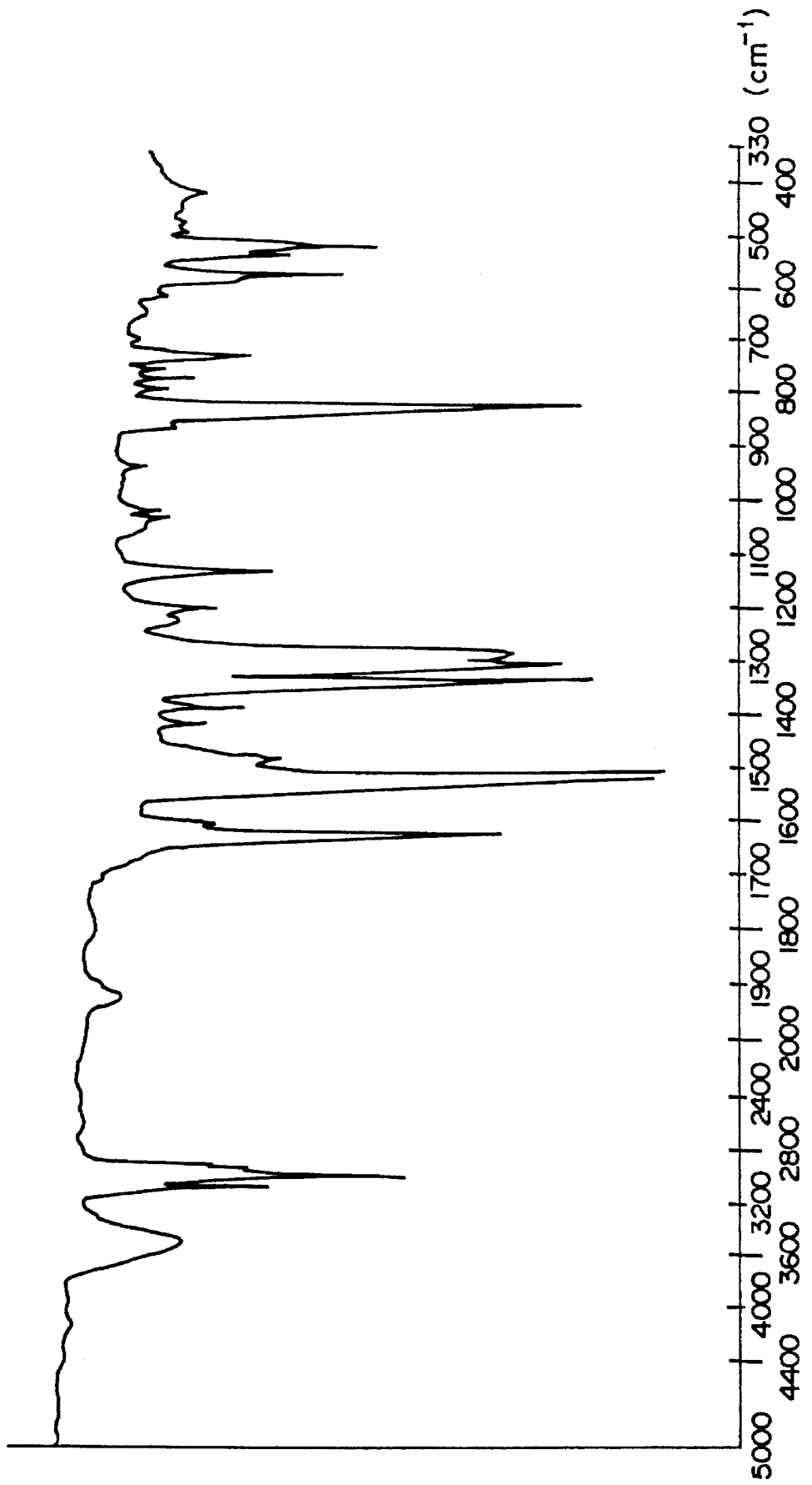
FIG. 7 is an infrared spectrum of an aminobiphneyl compound No. 1-109 for use in the present invention.
Figure 8:
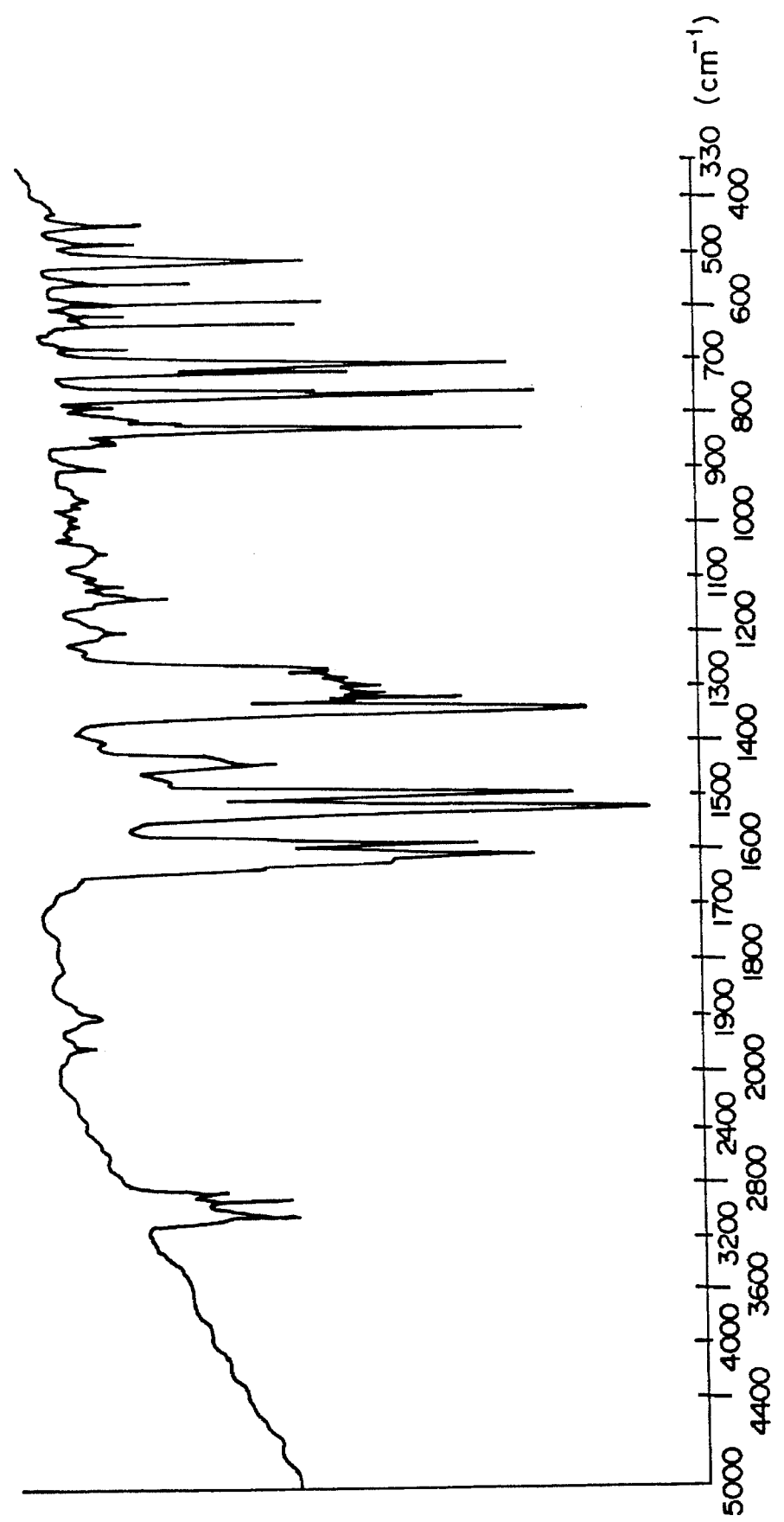
FIG. 8 is an infrared spectrum of an aminobiphneyl compound No. 1-134 for use in the present invention.
Figure 9:
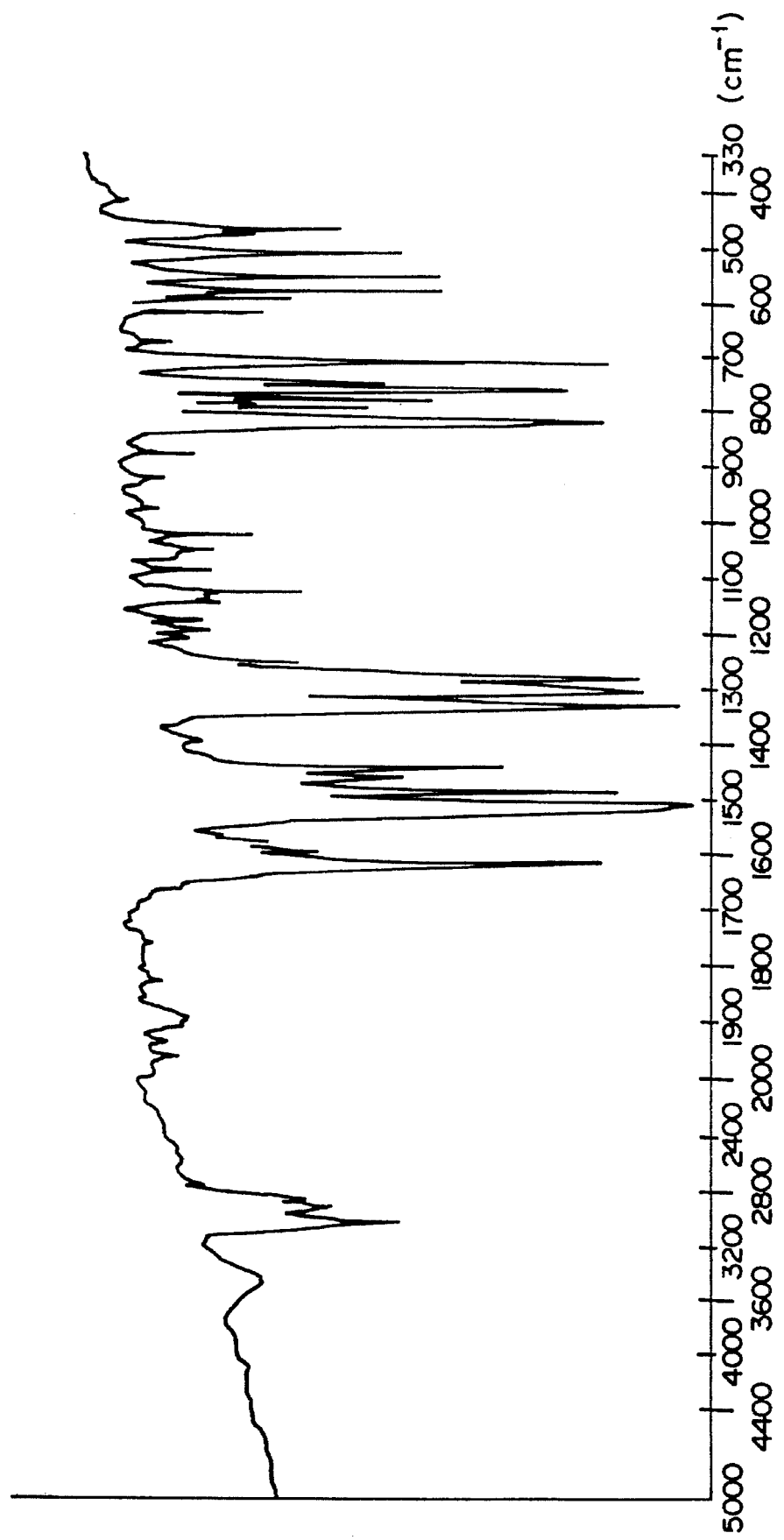
FIG. 9 is an infrared spectrum of an aminobiphenyl compound No. 1-135 for use in the present invention.

The aminobipheny compounds of the following general formula (I), which are novel and used in the present invention, can be prepared, for example, by a known condensation reaction of condensing (a-1) a halobiphenyl derivative of general formula (II), and (b-1) an arylamine derivative of general formula (III) in the presence finely-divided copper, copper oxide or copper halogenide, and (d) a sufficient amount of an alkali or alkali salt for the neutralization of hydrogen halogenide which is produced in the course of this condensation reaction, with or without (e) a reaction solvent, in an atmosphere of nitrogen at temperatures of about 150° C. to about 250° C.:

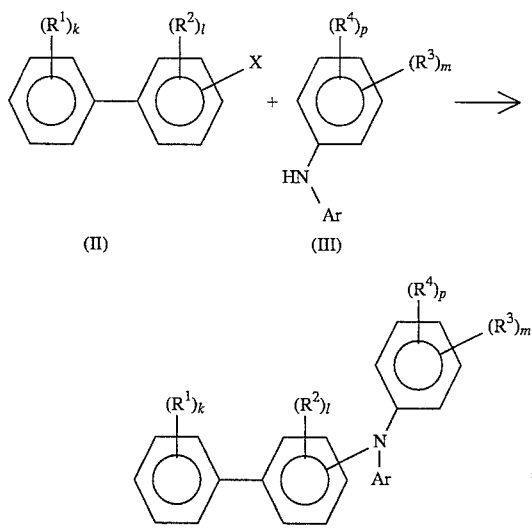

wherein $R^1$, $R^2$, $R^3$, $R^4$, k, l, m and p are respectively the same as defined previously, and X represents a halogen.

In the above condensation reaction, as the alkali or alkali salt, for example, sodium hydroxide and potassium hydroxide, sodium carbonate and potassium carbonate can be employed.

Further as the reaction solvent, nitrobenezene, dichlorobenzene, N,N-dimethylformamide, dimethyl sulfoxide, N-methylpyrrolidone, and 1,3-dimethyl-2-imidazolidinone can be employed.

Specific examples of the aminobiphenyl compounds for use in the present invention are collectively listed in Table 1. Those aminobiphenyl compounds can be synthesized in the manner as mentioned above.

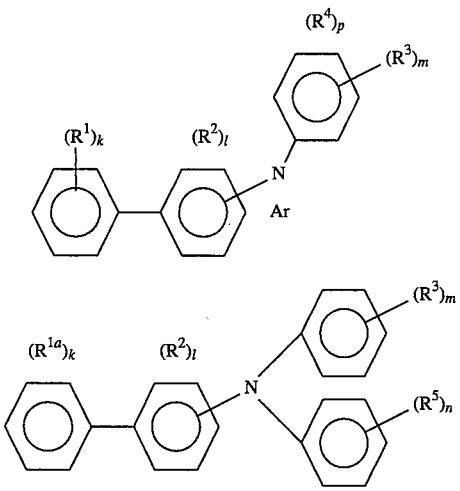

The above formula (I-1) corresponds to the case where $R^4$ and Ar in formula (I) are respectively hydrogen and

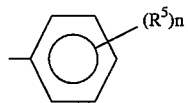

| Compounds No. | $R^1$ | $R^2$ | $R^3$ | $R^5$ |
|---|---|---|---|---|
| 1-1 | H | H | 4-$C_6H_4CH_3$ (p) | H |
| 1-2 | H | H | 4-$CH_3$ | 4-$CH_3$ |
| 1-3 | H | H | 3-$CH_3$ | 3-$CH_3$ |
| 1-4 | H | H | 2-$CH_3$ | 2-$CH_3$ |
| 1-5 | H | H | 4-$CH_3$ | H |
| 1-6 | H | H | 4-$C_2H_5$ | 4-$C_2H_5$ |
| 1-7 | H | H | 4-$C_2H_5$ | H |
| 1-8 | H | H | 4-$OCH_3$ | 4-$OCH_3$ |
| 1-9 | H | H | 3-$OCH_3$ | 3-$OCH_3$ |
| 1-10 | H | H | 2-$OCH_3$ | 2-$OCH_3$ |
| 1-11 | H | H | 4-$OCH_3$ | H |
| 1-12 | H | H | 4-$OCH_3$ | 4-$CH_3$ |
| 1-13 | H | H | 4-$OC_6H_5$ | H |
| 1-14 | H | H | 4-$iC_3H_7$ | 4-$iC_3H_7$ |
| 1-15 | H | H | 4-$NEt_2$ | H |
| 1-16 | H | H | 4-$C_6H_5$ | H |
| 1-17 | H | H | 4-$C_6H_5$ | 4-$C_6H_5$ |
| 1-18 | H | H | 4-$CH_2C_6H_5$ | H |
| 1-19 | H | H | 4-Cl | H |
| 1-20 | 4-$CH_3$ | H | H | H |
| 1-21 | 4-$CH_3$ | H | 4-$CH_3$ | 4-$CH_3$ |
| 1-22 | 4-$CH_3$ | H | 3-$CH_3$ | 3-$CH_3$ |
| 1-23 | 4-$CH_3$ | H | 2-$CH_3$ | 2-$CH_3$ |
| 1-24 | 4-$CH_3$ | H | 4-$CH_3$ | H |
| 1-25 | 4-$CH_3$ | H | 4-$C_2H_5$ | H |
| 1-26 | 4-$CH_3$ | H | 4-$C_2H_5$ | 4-$C_2H_5$ |
| 1-27 | 4-$CH_3$ | H | 4-$CH_3$ | 4-$OCH_3$ |
| 1-28 | 4-$CH_3$ | H | 4-$OCH_3$ | 4-$OCH_3$ |
| 1-29 | 4-$CH_3$ | H | 3-$OCH_3$ | 3-$OCH_3$ |
| 1-30 | 4-$CH_3$ | H | 4-$OCH_3$ | H |
| 1-31 | 4-$CH_3$ | H | 4-$OC_6H_5$ | H |
| 1-32 | 4-$CH_3$ | H | 4-$NEt_2$ | H |
| 1-33 | 4-$CH_3$ | H | 4-$C_6H_5$ | 4-$C_6H_5$ |
| 1-34 | 4-$CH_3$ | H | 4-$C_6H_5$ | H |
| 1-35 | 4-$CH_3$ | H | 3-Cl | H |
| 1-36 | 4-$C_2H_5$ | H | 4-$CH_3$ | 4-$CH_3$ |
| 1-37 | 4-$C_2H_5$ | H | 4-$OCH_3$ | 4-$OCH_3$ |
| 1-38 | 4-$C_2H_5$ | H | 3-$CH_3$ | H |
| 1-39 | 4-$C_2H_5$ | H | 3-$CH_3$ | 3-$CH_3$ |
| 1-40 | 3-$CH_3$ | H | 4-$CH_3$ | 4-$CH_3$ |
| 1-41 | 3-$CH_3$ | H | 3-$CH_3$ | 3-$CH_3$ |
| 1-42 | 3-$CH_3$ | H | 2-$CH_3$ | 2-$CH_3$ |
| 1-43 | 3-$CH_3$ | 3-$CH_3$ | 4-$CH_3$ | 4-$CH_3$ |
| 1-44 | H | 3-$CH_3$ | H | H |
| 1-45 | H | 3-$CH_3$ | 4-$CH_3$ | 4-$CH_3$ |
| 1-46 | H | 3-$CH_3$ | 3-$CH_3$ | 3-$CH_3$ |
| 1-47 | H | 2-$CH_3$ | 4-$CH_3$ | 4-$CH_3$ |
| 1-48 | 4-$C_2H_5$ | H | H | H |
| 1-49 | 3-$CH_3$ | H | H | H |
| 1-50 | 2-$CH_3$ | H | H | H |
| 1-51 | 2-$CH_3$ | H | 4-$CH_3$ | 4-$CH_3$ |
| 1-52 | 2-$CH_3$ | H | 3-$CH_3$ | 3-$CH_3$ |
| 1-53 | H | H | 2,4-$(CH_3)_2$ | H |
| 1-54 | H | H | 3,4-$CH_2O_2$ | H |
| 1-55 | 4-$CH_3$ | H | 3,4-$CH_2O_2$ | H |
| 1-56 | 4-$C_2H_5$ | H | 4-$C_6H_5$ | H |
| 1-57 | 4-$C_2H_5$ | H | 4-$C_6H_5$ | 4-$C_6H_5$ |
| 1-58 | 4-$C_6H_5$ | H | H | H |
| 1-59 | 4-$C_6H_5$ | H | 4-$CH_3$ | 4-$CH_3$ |
| 1-60 | 4-$C_6H_5$ | H | 3-$CH_3$ | 3-$CH_3$ |
| 1-61 | 4-$C_6H_5$ | H | 4-$C_2H_5$ | 4-$C_2H_5$ |
| 1-62 | 4-$OCH_3$ | H | H | H |
| 1-63 | 4-$OCH_3$ | H | 4-$CH_3$ | 4-$CH_3$ |
| 1-64 | 4-$OCH_3$ | H | 3-$CH_3$ | 3-$CH_3$ |
| 1-65 | 4-$OCH_3$ | H | 4-$CH_3$ | H |
| 1-66 | 4-$OCH_3$ | H | 4-$OCH_3$ | 4-$OCH_3$ |
| 1-67 | 4-$OCH_3$ | H | 4-$OCH_3$ | H |
| 1-68 | 4-$OCH_3$ | H | 4-$OCH_3$ | 4-$CH_3$ |
| 1-69 | 4-$OC_6H_5$ | H | H | H |
| 1-70 | 4-$OC_6H_5$ | H | 4-$CH_3$ | 4-$CH_3$ |
| 1-71 | 4-$OC_6H_5$ | H | 3-$CH_3$ | 3-$CH_3$ |
| 1-72 | 4-$OC_6H_5$ | H | 4-$CH_3$ | H |
| 1-73 | 3-Cl | H | 4-$CH_3$ | 4-$CH_3$ |
| 1-74 | 3-Cl | H | 4-$OCH_3$ | 4-$OCH_3$ |
| 1-75 | 3-$OC_6H_5$ | H | H | H |
| 1-76 | 3-$OC_6H_5$ | H | 4-$CH_3$ | 4-$CH_3$ |
| 1-77 | 3-$OC_6H_5$ | H | 3-$CH_3$ | 3-$CH_3$ |
| 1-78 | H | H | 4-$nC_3H_7$ | H |
| 1-79 | 4-$nC_3H_7$ | H | H | H |
| 1-80 | 4-$nC_3H_7$ | H | 4-$CH_3$ | 4-$CH_3$ |
| 1-81 | 4-$C_6H_5$ | H | 4-$nC_3H_7$ | 4-$nC_3H_7$ |
| 1-82 | 4-$SCH_3$ | H | H | H |
| 1-83 | 4-$SCH_3$ | H | 4-$CH_3$ | 4-$CH_3$ |
| 1-84 | H | H | 4-$SCH_3$ | 4-$SCH_3$ |
| 1-85 | H | H | 4-$SCH_3$ | H |
| 1-86 | H | H | 4-$tC_4H_9$ | 4-$tC_4H_9$ |
| 1-87 | H | H | 4-$nC_4H_9$ | 4-$nC_4H_9$ |
| 1-88 | 4-$CH_2C_6H_5$ | H | H | H |
| 1-89 | 4-$CH_2C_6H_5$ | H | 4-$CH_3$ | 4-$CH_3$ |
| 1-90 | 4-$CH_2C_6H_5$ | H | 4-$OCH_3$ | H |
| 1-91 | 4-$CH_2C_6H_5$ | H | 3-$CH_3$ | 3-$CH_3$ |
| 1-92 | 4-$CH_2C_6H_5$ | H | 2-$CH_3$ | 2-$CH_3$ |
| 1-93 | 4-$CH_2C_6H_5$ | H | 4-$OCH_3$ | 4-$OCH_3$ |
| 1-94 | 4-$CH_2C_6H_5$ | H | 3-$OCH_3$ | 3-$OCH_3$ |
| 1-95 | 4-$CH_3$ | H | 4-$C_6H_4CH_3$ (p) | H |
| 1-96 | 4-$CH_3$ | H | 4-$tC_4H_9$ | 4-$tC_4H_9$ |
| 1-97 | 4-$CH_3$ | H | 4-$iC_3H_7$ | 4-$iC_3H_7$ |
| 1-98 | 4-$C_2H_5$ | H | 4-$C_6H_4CH_3$ (p) | H |

-continued

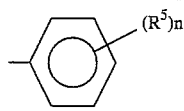

| Compounds No. | R¹ | R² | R³ | R⁵ |
|---|---|---|---|---|
| 1-99 | 4-C₂H₅ | H | 4-tC₄H₉ | 4-tC₄H₉ |
| 1-100 | 4-C₂H₅ | H | 4-iC₃H₇ | 4-iC₃H₇ |
| 1-101 | 4-OCH₃ | H | 4-C₆H₄CH₃ (p) | H |
| 1-102 | 4-OCH₃ | H | 4-tC₄H₉ | 4-tC₄H₉ |
| 1-103 | 4-OCH₃ | H | 4-iC₃H₇ | 4-iC₃H₇ |
| 1-104 | 4-tC₄H₉ | H | H | H |
| 1-105 | 4-tC₄H₉ | H | 4-CH₃ | 4-CH₃ |
| 1-106 | 4-tC₄H₉ | H | 3-CH₃ | 3-CH₃ |
| 1-107 | 4-tC₄H₉ | H | 2-CH₃ | 2-CH₃ |
| 1-108 | 4-tC₄H₉ | H | 4-OCH₃ | 4-OCH₃ |
| 1-109 | 4-tC₄H₉ | H | 4-OCH₃ | H |
| 1-110 | 4-tC₄H₉ | H | 4-tC₄H₉ | 4-tC₄H₉ |
| 1-111 | 4-tC₄H₉ | H | 4-iC₃H₇ | 4-iC₃H₇ |
| 1-112 | 4-tC₄H₉ | H | 4-C₆H₄CH₃ (p) | H |
| 1-113 | 4-OC₂H₅ | H | 4-CH₃ | 4-CH₃ |
| 1-114 | 4-OC₂H₅ | H | 3-CH₃ | 3-CH₃ |
| 1-115 | 4-OC₂H₅ | H | 2-CH₃ | 2-CH₃ |
| 1-116 | 4-OC₂H₅ | H | 4-OCH₃ | 4-OCH₃ |
| 1-117 | 4-OC₂H₅ | H | 4-OCH₃ | H |
| 1-118 | 4-OC₂H₅ | H | 4-tC₄H₉ | 4-tC₄H₉ |
| 1-119 | 4-OC₂H₅ | H | 4-iC₃H₇ | 4-iC₃H₇ |
| 1-120 | 4-OC₂H₅ | H | 4-C₆H₄CH₃ (p) | H |
| 1-121 | H | 3-CH₃ | 4-tC₄H₉ | 4-tC₄H₉ |
| 1-122 | H | 3-CH₃ | 4-C₆H₄CH₃ (p) | H |
| 1-123 | H | 3-OCH₃ | 4-CH₃ | 4-CH₃ |
| 1-124 | H | 3-OCH₃ | 3-CH₃ | 3-CH₃ |
| 1-125 | H | 3-OCH₃ | 4-OCH₃ | 4-OCH₃ |
| 1-126 | H | 3-OCH₃ | 4-tC₄H₉ | 4-tC₄H₉ |
| 1-127 | H | 3-OCH₃ | 4-C₆C₄CH₃ (p) | H |
| 1-128 | 3-CH₃ | 3-CH₃ | 4-CH₃ | 4-CH₃ |
| 1-129 | 3-CH₃ | 3-CH₃ | 3-CH₃ | 3-CH₃ |
| 1-130 | 3-CH₃ | 3-CH₃ | 2-CH₃ | 2-CH₃ |
| 1-131 | 3-CH₃ | 3-CH₃ | 4-OCH₃ | 4-OCH₃ |
| 1-132 | H | 3-CH₃ | 4-OCH₃ | 4-OCH₃ |
| 1-133 | 4-NO₂ | H | 4-CH₃ | 4-CH₃ |

1-134

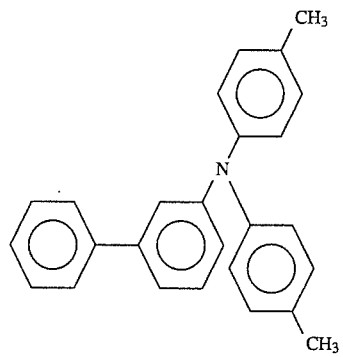

1-135

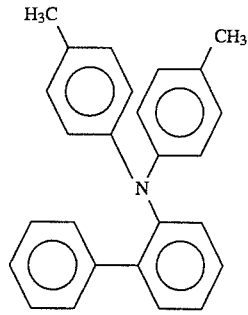

The following are examples of the procedure for the preparation of representative aminobiphenyl compounds for use in the present invention:

Preparation of Aminobiphenyl Compound No. 1-2 in Table 1

600 ml of nitrobenzene was added to a mixture of 49.90 g (0.253 mol) of 4,4'-dimethyldiphenylamine, 78.00 g (0.278 mol) of 4-iodine biphenyl, 38.42 g (0.278 mol) of potassium carbonate, and 0.10 g of copper powder. The mixture was placed in an ester pipe and azeotropically heated for dehydration, with stirring, at 208° C. to 209° C. for 15 hours as a nitrogen gas was caused to flow over the reaction mixture.

The reaction mixture was then cooled to room temperature and filtered through a Celite filter to obtain a filtrate. The nitrobenzene was distilled away from the filtrate under reduced pressure. The residue was extracted with toluene, washed with water, dried by use of magnesium sulfate, and condensed under reduced pressure, whereby a dark brown oily material was obtained.

The thus obtained product Was subjected to a silica gel column chromatography by use of a toluene-n-hexane mixed solvent as an eluent, and recrystallized from a mixed solvent of ethanol and ethyl acetate, whereby N,N-bis(4-methylphenyl)-[1,1'-biphenyl]-4-amine was obtained in the form of colorless needles with a yield of 52.98 g (59.9%). The melting point of the product was 129.5° C. to 130.5° C.

The results of the elemental analysis of the thus obtained N,N-bis(4-methylphenyl)-[1,1'-biphenyl]-4-amine were as follows:

|  | % C | % H | % N |
|---|---|---|---|
| Found | 89.28 | 6.72 | 3.85 |
| Calculated | 89.36 | 6.63 | 4.01 |

The above calculation was based on the formula for N,N-bis(4-methylphenyl)-[1,1'-biphenyl]-4-amine of $C_{26}H_{23}N$.

An infrared spectrum of the N,N-bis(4-methylphenyl)-[1,1'-biphenyl]-4-amine (Aminobiphenyl Compound No. 1-2 in Table 2), taken by use of a KBr tablet, is shown in FIG. 1.

Preparation of Aminobiphenyl Compound No. 1-21 in Table 1

50 ml of nitrobenzene was added to a mixture of 2.27 g of 4,4'-ditolylamine, 3.38 g of 4-methyl-4'-iodine biphenyl, 1.67 g of potassium carbonate, and 50 mg of copper powder. The mixture was placed in an ester pipe and azeotropically heated for dehydration, with stirring, at 205° C. to 208° C. for 11 hours as a nitrogen gas was caused to flow over the mixture. The reaction mixture Was then cooled to room temperature and filtered through a Celite filter to obtain a filtrate. The nitrobenzene was distilled away from the filtrate under reduced pressure. The residue was extracted with toluene, washed with water, dried by use of magnesium sulfate, and condensed under reduced pressure, whereby a dark brown oily material was obtained. The thus obtained product was subjected to a silica gel column chromatography two times, first by use of toluene, and subsequently by a toluene—n-hexane mixed solvent as eluents, and recrystallized from ethanol, whereby 4-methyl-4'-N,N-bis(4-methyphenyl] aminobiphenyl (Aminobiphenyl Compound No. 1-21 in Table 1) was obtained in the form of colorless needles with a yield of 3.08 g (52%). The melting point of the product was 118.0° C. to 119.0° C.

The results of the elemental analysis of the thus obtained 4-methyl-4'-N,N-bis(4-methylphenly)aminobiphenyl were as follows:

|  | % C | % H | % N |
|---|---|---|---|
| Found | 88.97 | 6.84 | 3.65 |
| Calculated | 89.21 | 6.93 | 3.86 |

The above calculation was based on the formula for 4-methyl- 4'-N,N-bis(4-methylphenyl)aminobiphenyl of $C_{27}H_{25}N$.

In addition to the above aminobiphenyl compounds for use in the present invention, the aminobiphenyl compounds listed in Table 2 were synthesized in the same manner as mentioned above.

The melting points and the results of elemental analysis of further representative examples of the aminobiphenyl compounds for use in the present invention are shown in Table 2:

TABLE 2

| Aminobiphenyl Compounds | $R^1$ | $R^2$ | $R^3$ | $R^5$ | m.p. (°C.) | Elemental Found Analysis (Calculated) | | |
|---|---|---|---|---|---|---|---|---|
| | | | | | | % C | % H | % N |
| No. 1-3 | H | H | 3-$CH_3$ | 3-$CH_3$ | 104.5–105.5 | 89.48 (89.36) | 6.71 (6.63) | 3.76 (4.01) |
| No. 1-4 | H | H | 2-$CH_3$ | 2-$CH_3$ | 118.5–120.0 | 89.30 (89.36) | 6.59 (6.63) | 3.98 (4.01) |
| No. 1-5 | H | H | 4-$CH_3$ | H | 96.0–98.0 | 89.64 (89.51) | 6.30 (6.31) | 3.92 (4.18) |
| No. 1-16 | H | H | H | H | 161.0–162.0 | 91.05 (90.64) | 5.71 (5.83) | 3.49 (3.52) |
| No. 1-20 | 4-$CH_3$ | H | H | H | 104.0–105.0 | 89.27 (89.51) | 6.10 (6.31) | 4.02 (4.18) |
| No. 1-22 | 4-$CH_3$ | H | 3-$CH_3$ | 3-$CH_3$ | 111.0–112.0 | 89.37 (89.21) | 6.74 (6.93) | 3.66 (3.86) |
| No. 1-24 | 4-$CH_3$ | H | 4-$CH_3$ | H | 87.5–89.5 | 89.07 (89.36) | 6.52 (6.63) | 3.75 (4.01) |
| No. 1-27 | 4-$CH_3$ | H | 4-$CH_3$ | 4-$OCH_3$ | 94.0–95.0 | 85.20 (85.45) | 6.52 (6.64) | 3.55 (3.69) |
| No. 1-28 | 4-$CH_3$ | H | 4-$OCH_3$ | 4-OCH3 | 113.5–114.0 | 81.95 (81.98) | 6.38 (6.38) | 3.35 (3.54) |
| No. 1-30 | 4-$CH_3$ | H | 4-$OCH_3$ | H | 103.5–104.5 | 85.47 (85.45) | 6.22 (6.34) | 3.80 (3.83) |
| No. 1-36 | 4-$CH_2CH_3$ | H | 4-$CH_3$ | 4-$CH_3$ | 87.0–88.0 | 89.24 (89.08) | 7.29 (7.21) | 3.49 (3.71) |
| No. 1-37 | 4-$CH_2CH_3$ | H | 4-$OCH_3$ | 4-$OCH_3$ | 129.0–129.5 | 81.94 (82.11) | 6.67 (6.66) | 3.26 (3.42) |
| No. 1-39 | 4-$CH_2CH_3$ | H | 3-$CH_3$ | 3-$CH_3$ | 123.5–124.5 | 89.33 (89.08) | 7.40 (7.21) | 3.51 (3.71) |
| No. 1-43 | 3-$CH_3$ | 3-$CH_3$ | 4-$CH_3$ | 4-$CH_3$ | 71.5–73.5 | 88.91 (89.08) | 7.15 (7.21) | 3.45 (3.71) |
| No. 1-48 | 4-$CH_2CH_3$ | H | H | H | 94.0–95.0 | 89.23 (89.34) | 6.49 (6.65) | 3.81 (4.01) |
| No. 1-62 | 4-$OCH_3$ | H | H | H | 132.5–133.5 | 85.42 (85.44) | 5.96 (6.02) | 3.98 (3.99) |
| No. 1-63 | 4-$OCH_3$ | H | 4-$CH_3$ | 4-$CH_3$ | 142.7–143.7 | 85.59 (85.45) | 6.71 (6.64) | 3.80 (3.69) |
| No. 1-64 | 4-$OCH_3$ | H | 3-$CH_3$ | 3-$CH_3$ | 102.5–103.5 | 85.49 (85.45) | 6.43 (6.64) | 3.59 (3.69) |
| No. 1-66 | 4-$OCH_3$ | H | 4-$OCH_3$ | 4-$OCH_3$ | 116.0–117.5 | 78.50 (78.81) | 5.98 (6.12) | 3.35 (3.40) |
| No. 1-104 | 4-tert-$C_4H_9$ | H | H | H | 124.5–125.0 | 89.19 (89.08) | 6.92 (7.21) | 3.63 (3.71) |
| No. 1-105 | 4-tert-$C_4H_9$ | H | 4-$CH_3$ | 4-$CH_3$ | 101.0–103.0 | 88.99 (88.84) | 7.56 (7.71) | 3.58 (3.45) |
| No. 1-106 | 4-tert-$C_4H_9$ | H | 3-$CH_3$ | 3-$CH_3$ | 90.5–93.5 | 88.78 (88.84) | 7.81 (7.71) | 3.75 (3.45) |
| No. 1-108 | 4-tert-$C_4H_9$ | H | 4-$OCH_3$ | 4-$OCH_3$ | 89.5–100.5 | 82.39 (83.33) | 7.14 (7.15) | 3.22 (3.20) |
| No. 1-133 | 4-$NO_2$ | H | 4-$CH_3$ | 4-$CH_3$ | 161.0–162.0 | 79.16 (79.16) | 5.45 (5.62) | 6.98 (7.10) |

TABLE 2-continued
| Aminobiphenyl Compounds | Structural Formula | m.p. (°C.) | Elemental Found Analysis (Calculated) | | |
|---|---|---|---|---|---|
| | | | % C | % H | % N |
| No. 1-134 | 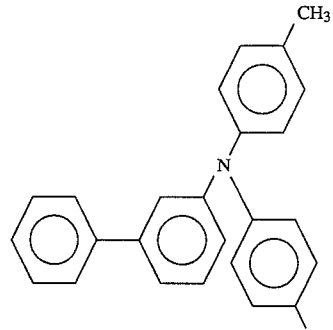 | 105.0–105.7 | 89.04 (89.36) | 6.35 (6.63) | 3.92 (4.01) |
| No. 1-135 | 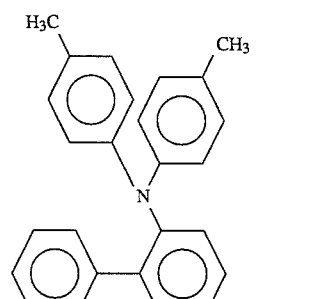 | 136.0–136.5 | 89.25 (89.36) | 6.59 (6.63) | 3.96 (4.01) |
Further specific examples of the aminobiphenyl compounds for use in the present invention are collectively listed in Table 3.
TABLE 3
| Compounds No. | $R^1$ | $R^2$ | $R^3$ | $R^4$ | Ar |
|---|---|---|---|---|---|
| | 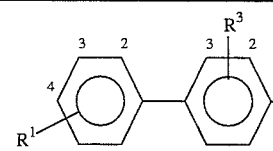 | | | | (I)-2 |
| 2-1 | H | H | H | H | 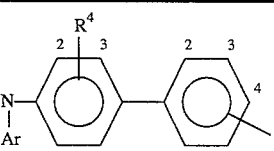 |
| 2-2 | 4-$CH_3$ | 4-$CH_3$ | H | H |  |
| 2-3 | 4-$C_2H_5$ | 4-$C_2H_5$ | H | H | 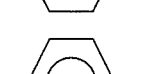 |
| 2-4 | 3-$CH_3$ | 3-$CH_3$ | H | H |  |

TABLE 3-continued

| Compounds No. | R¹ | R² | R³ | R⁴ | Ar |
|---|---|---|---|---|---|
| 2-5 | 3-CH₃ | 2-CH₃ | H | H | —C₆H₄—CH₃ |
| 2-6 | 4-NMe₂ | 4-NMe₂ | H | H | —C₆H₄—CH₃ |
| 2-7 | 4-NEt₂ | 4-NEt₂ | H | H | —C₆H₄—CH₃ |
| 2-8 | 4-OCH₃ | 4-OCH₃ | H | H | —C₆H₄—CH₃ |
| 2-9 | 4-OC₆H₅ | 4-OC₆H₅ | H | H | —C₆H₄—CH₃ |
| 2-10 | 4-nC₃H₇ | 4-nC₃H₇ | H | H | —C₆H₄—CH₃ |
| 2-11 | 4-SCH₃ | 4-SCH₃ | H | H | —C₆H₄—CH₃ |
| 2-12 | 4-OC₂H₅ | 4-OC₂H₅ | H | H | —C₆H₄—CH₃ |
| 2-13 | 4-tC₄H₉ | 4-tC₄H₉ | H | H | —C₆H₄—CH₃ |
| 2-14 | 4-NH₂ | 4-NH₂ | H | H | —C₆H₄—CH₃ |
| 2-15 | 4-C₅H₅ | 4-C₅C₅ | H | H | —C₆H₄—CH₃ |
| 2-16 | 4-CH₃ | 4-CH₃ | H | H | —C₆H₅ |
| 2-17 | 4-C₂H₅ | 4-C₂H₅ | H | H | —C₆H₅ |
| 2-18 | 4-NMe₂ | 4-NMe₂ | H | H | —C₆H₅ |

TABLE 3-continued
| Compounds No. | R¹ | R² | R³ | R⁴ | Ar |
|---|---|---|---|---|---|
| 2-19 | 4-OCH₃ | 4-OCH₃ | H | H |  |
| 2-20 | H | H | H | H | 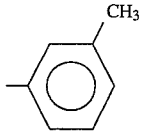 |
| 2-21 | 4-CH₃ | 4-CH₃ | H | H | 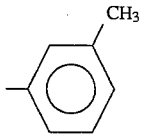 |
| 2-22 | 4-C₂H₅ | 4-C₂H₅ | H | H | 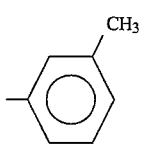 |
| 2-23 | 4-NMe₂ | 4-NMe₂ | H | H | 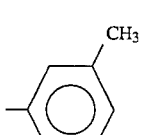 |
| 2-24 | 4-NEt₂ | 4-NEt₂ | H | H | 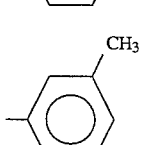 |
| 2-25 | 4-OCH₃ | 4-OCH₃ | H | H | 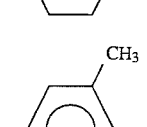 |
| 2-26 | H | H | H | H | 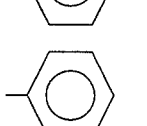 |
| 2-27 | 4-CH₃ | 4-CH₃ | H | H | 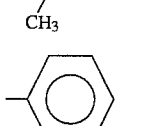 |
| 2-28 | 4-C₂H₅ | 4-C₂H₅ | H | H | 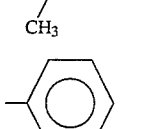 |
| 2-29 | H | H | H | H | 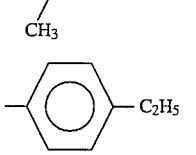 |

TABLE 3-continued
| Compounds No. | R¹ | R² | R³ | R⁴ | Ar |
|---|---|---|---|---|---|
| 2-30 | 4-CH₃ | 4-CH₃ | H | H | 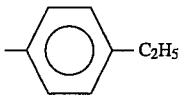—C₂H₅ |
| 2-31 | 4-C₂H₅ | 4-C₂H₅ | H | H | 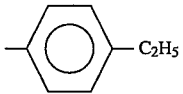—C₂H₅ |
| 2-32 | 4-OCH₃ | 4-OCH₃ | H | H | 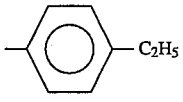—C₂H₅ |
| 2-33 | H | H | H | H | 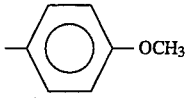—OCH₃ |
| 2-34 | 4-CH₃ | 4-CH₃ | H | H | 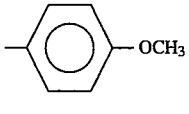—OCH₃ |
| 2-35 | 4-C₂H₅ | 4-C₂H₅ | H | H | —OCH₃ |
| 2-36 | 4-OCH₃ | 4-OCH₃ | H | H | —OCH₃ |
| 2-37 | H | H | H | H | —C₃H₇(i) |
| 2-38 | 4-CH₃ | 4-CH₃ | H | H | —C₃H₇(i) |
| 2-39 | H | H | H | H | 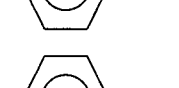—C₃H₇(n) |
| 2-40 | 4-CH₃ | 4-CH₃ | H | H | —C₃H₇(n) |
| 2-41 | H | H | H | H | 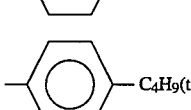—C₄H₉(t) |
| 2-42 | 4-CH₃ | 4-CH₃ | H | H | 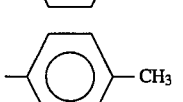—C₄H₉(t) |
| 2-43 | 3-CH₃ | 3-CH₃ | 2-CH₃ | 2-CH₃ | —CH₃ |

TABLE 3-continued
| Compounds No. | R¹ | R² | R³ | R⁴ | Ar |
|---|---|---|---|---|---|
| 2-44 | 3-CH₃ | 3-CH₃ | 2-CH₃ | 2-CH₃ | 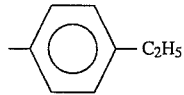 |
| 2-45 | H | H | 2-CH₃ | 2-CH₃ | 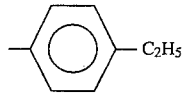 |
| 2-46 | 3-CH₃ | 3-CH₃ | 3-CH₃ | 3-CH₃ | 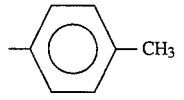 |
| 2-47 | H | H | 3-CH₃ | 3-CH₃ | 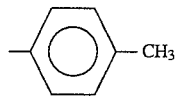 |
| 2-48 | H | H | 2-OCH₃ | 2-OCH₃ | 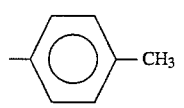 |
| 2-49 | 4-CH₃ | H | H | H | 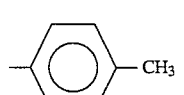 |
| 2-50 | 4-CH₃ | 3-CH₃ | H | H | 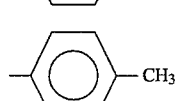 |
| 2-51 | 4-CH₃ | 2-CH₃ | H | H | 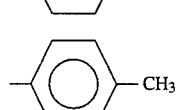 |
| 2-52 | 4-CH₃ | 4-OCH₃ | H | H | 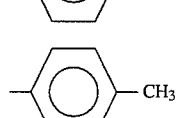 |
| 2-53 | 4-CH₃ | 4-C₂H₅ | H | H |  |
| 2-54 | 4-CH₃ | 4-NMe₂ | H | H |  |
| 2-55 | 4-CH₃ | 4-OC₆H₅ | H | H | 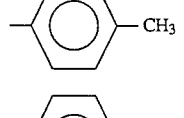 |
| 2-56 | 4-CH₃ | 4-C₆H₅ | H | H | 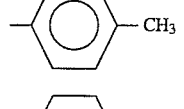 |
| 2-57 | 4-CH₃ | 4-nC₃H₇ | H | H | 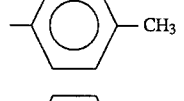 |

TABLE 3-continued
| Compounds No. | R¹ | R² | R³ | R⁴ | Ar |
|---|---|---|---|---|---|
| 2-58 | 4-CH₃ | 3-CH₃ | H | 2-CH₃ | 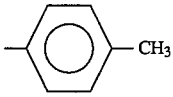 |
| 2-59 | 3-CH₃ | H | H | H | 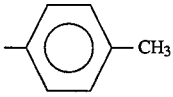 |
| 2-60 | 3-CH₃ | 2-CH₃ | H | H | 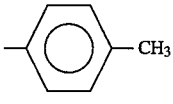 |
| 2-61 | 3-CH₃ | 4-OCH₃ | H | H | 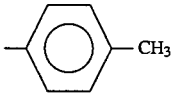 |
| 2-62 | 4-OCH₃ | 4-C₂H₅ | H | H | 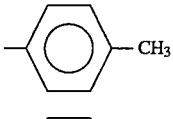 |
| 2-63 | 4-C₂H₅ | 4-nC₃H₇ | H | H | 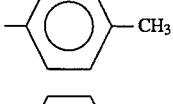 |
| 2-64 | 4-CH₃ | 3-CH₃ | H | H |  |
| 2-65 | 4-CH₃ | 4-OCH₃ | H | H |  |
| 2-66 | 4-CH₃ | 4-C₂H₅ | H | H |  |
| 2-67 | 3-CH₃ | H | H | H |  |
| 2-68 | 3-CH₃ | 4-OCH₃ | H | H |  |
| 2-69 | 4-OCH₃ | 4-C₂H₅ | H | H |  |
| 2-70 | 4-CH₃ | H | H | H | 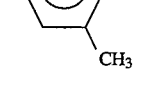 |

TABLE 3-continued
| Compounds No. | R¹ | R² | R³ | R⁴ | Ar |
|---|---|---|---|---|---|
| 2-71 | 4-CH₃ | 3-CH₃ | H | H | 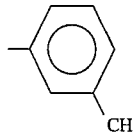 |
| 2-72 | 4-CH₃ | 4-OCH₃ | H | H | 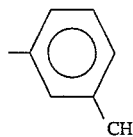 |
| 2-73 | 4-CH₃ | 4-C₂H₅ | H | H | 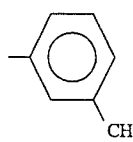 |
| 2-74 | 3-CH₃ | H | H | H | 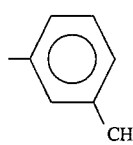 |
| 2-75 | 3-CH₃ | 4-OCH₃ | H | H | 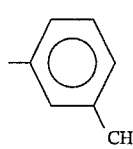 |
| 2-76 | 4-OCH₃ | 4-C₂H₅ | H | H | 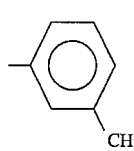 |
| 2-77 | 4-CH₃ | H | H | H | 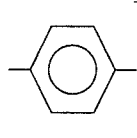 |
| 2-78 | 4-CH₃ | 3-CH₃ | H | H | 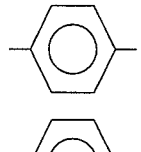 |
| 2-79 | 4-CH₃ | 4-OCH₃ | H | H | 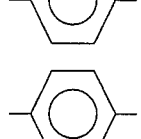 |
| 2-80 | 3-CH₃ | H | H | H |  |
| 2-81 | 3-CH₃ | 4-OCH₃ | H | H | 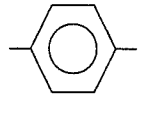 |
| 2-82 | 4-CH₃ | H | H | H | 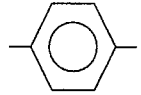 |

TABLE 3-continued
| Compounds No. | R¹ | R² | R³ | R⁴ | Ar |
|---|---|---|---|---|---|
| 2-83 | 4-CH₃ | 3-CH₃ | H | H | 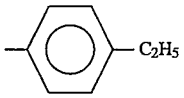 |
| 2-84 | 4-CH₃ | 4-OCH₃ | H | H | 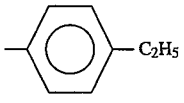 |
| 2-85 | 3-CH₃ | H | H | H | 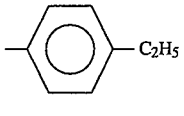 |
| 2-86 | 3-CH₃ | 4-OCH₃ | H | H | 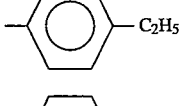 |
| 2-87 | 4-C₂H₅ | H | H | H |  |
| 2-88 | H | H | H | H | 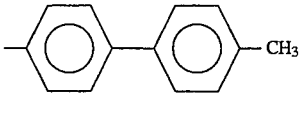 |
| 2-89 | 4-CH₃ | 4-CH₃ | H | H | 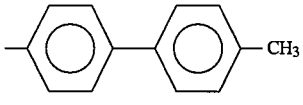 |
| 2-90 | 4-C₂H₅ | 4-C₂H₅ | H | H | 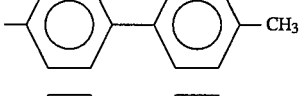 |
| 2-91 | 3-CH₃ | 3-CH₃ | H | H | 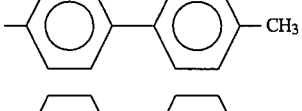 |
| 2-92 | 2-CH₃ | 2-CH₃ | H | H | 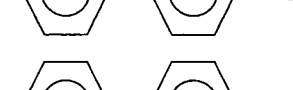 |
| 2-93 | 4-NMe₂ | 4-NMe₂ | H | H | 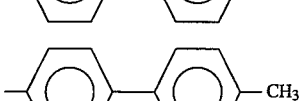 |
| 2-94 | 4-NEt₂ | 4-NEt₂ | H | H | 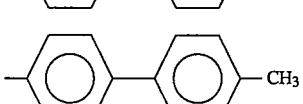 |
| 2-95 | 4-OCH₃ | 4-OCH₃ | H | H | 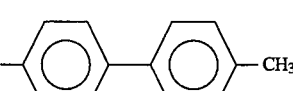 |
| 2-96 | 4-OC₆H₅ | 4-OC₆H₅ | H | H | 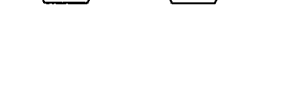 |

TABLE 3-continued

| Compounds No. | R¹ | R² | R³ | R⁴ | Ar |
|---|---|---|---|---|---|
| 2-97 | 4-nC₃H₇ | 4-nC₃H₇ | H | H | -C₆H₄-C₆H₄-CH₃ |
| 2-98 | 4-SCH₃ | 4-SCH₃ | H | H | -C₆H₄-C₆H₄-CH₃ |
| 2-99 | 4-OC₂H₅ | 4-OC₂H₅ | H | H | -C₆H₄-C₆H₄-CH₃ |
| 2-100 | 4-tC₄H₉ | 4-tC₄H₉ | H | H | -C₆H₄-C₆H₄-CH₃ |
| 2-101 | 4-NH₂ | 4-NH₂ | H | H | -C₆H₄-C₆H₄-CH₃ |
| 2-102 | 4-C₆H₅ | 4-C₆H₅ | H | H | -C₆H₄-C₆H₄-CH₃ |
| 2-103 | 4-CH₃ | 4-CH₃ | H | H | -C₆H₄-C₆H₅ |
| 2-104 | 4-C₂H₅ | 4-C₂H₅ | H | H | -C₆H₄-C₆H₅ |
| 2-105 | 3-CH₃ | 3-CH₃ | H | H | -C₆H₄-C₆H₅ |
| 2-106 | 4-tC₄H₉ | 4-tC₄H₉ | H | H | -C₆H₄-C₆H₅ |
| 2-107 | 4-OCH₃ | 4-OCH₃ | H | H | -C₆H₄-C₆H₅ |
| 2-108 | H | H | H | H | -C₆H₄-C₆H₄-OCH₃ |
| 2-109 | 4-CH₃ | 4-CH₃ | H | H | -C₆H₄-C₆H₄-OCH₃ |
| 2-110 | 4-C₂H₅ | 4-C₂H₅ | H | H | -C₆H₄-C₆H₄-OCH₃ |

TABLE 3-continued

| Compounds No. | R¹ | R² | R³ | R⁴ | Ar |
|---|---|---|---|---|---|
| 2-111 | 3-CH₃ | 3-CH₃ | H | H | —C₆H₄—C₆H₄—OCH₃ |
| 2-112 | 4-NMe | 4-NMe₂ | H | H | —C₆H₄—C₆H₄—OCH₃ |
| 2-113 | 4-OCH₃ | 4-OCH₃ | H | H | —C₆H₄—C₆H₄—OCH₃ |
| 2-114 | H | H | H | H | —C₆H₄—C₆H₄—C₂H₅ |
| 2-115 | 4-CH₃ | 4-CH₃ | H | H | —C₆H₄—C₆H₄—C₂H₅ |
| 2-116 | 4-C₂H₅ | 4-C₂H₅ | H | H | —C₆H₄—C₆H₄—C₂H₅ |
| 2-117 | 3-CH₃ | 3-CH₃ | H | H | —C₆H₄—C₆H₄—C₂H₅ |
| 2-118 | 4-NMe₂ | 4-NMe₂ | H | H | —C₆H₄—C₆H₄—C₂H₅ |
| 2-119 | 4-OCH₃ | 4-OCH₃ | H | H | —C₆H₄—C₆H₄—C₂H₅ |
| 2-120 | 4-nC₃H₇ | 4-nC₃H₇ | H | H | —C₆H₄—C₆H₄—C₂H₅ |
| 2-121 | H | H | H | H | —C₆H₄—C₆H₄—C₃H₇(n) |
| 2-122 | 4-CH₃ | 4-CH₃ | H | H | —C₆H₄—C₆H₄—C₃H₇(n) |
| 2-123 | 4-C₂H₅ | 4-C₂H₅ | H | H | —C₆H₄—C₆H₄—C₃H₇(n) |
| 2-124 | 3-CH₃ | 3-CH₃ | H | H | —C₆H₄—C₆H₄—C₃H₇(n) |

TABLE 3-continued
| Compounds No. | R¹ | R² | R³ | R⁴ | Ar |
|---|---|---|---|---|---|
| 2-125 | 4-NMe₂ | 4-NMe₂ | H | H | 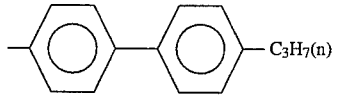 |
| 2-126 | 4-OCH₃ | 4-OCH₃ | H | H | 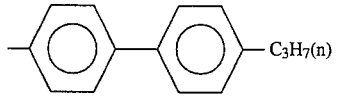 |
| 2-127 | 4-nC₃H₇ | 4-nC₃H₇ | H | H | 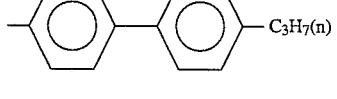 |
| 2-128 | H | H | H | H | 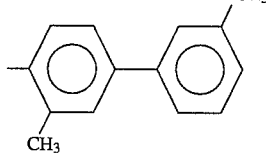 |
| 2-129 | 4-CH₃ | 4-CH₃ | H | H | 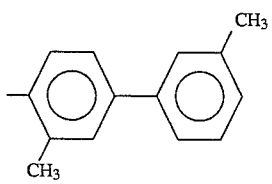 |
| 2-130 | 4-C₂H₅ | 4-C₂H₅ | H | H | 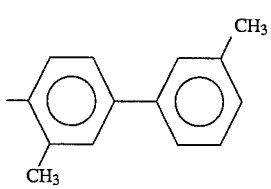 |
| 2-131 | 3-CH₃ | 3-CH₃ | H | H | 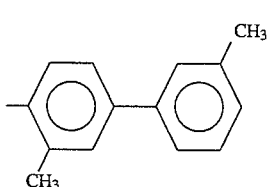 |
| 2-132 | 4-NMe₂ | 4-NMe₂ | H | H | 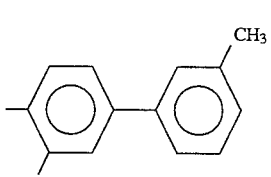 |
| 2-133 | 4-OCH₃ | 4-OCH₃ | H | H | 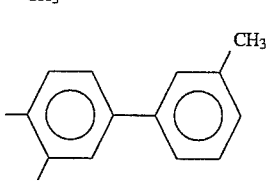 |
| 2-134 | H | H | H | H | 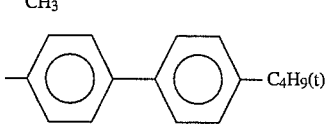 |

TABLE 3-continued
| Compounds No. | R¹ | R² | R³ | R⁴ | Ar |
|---|---|---|---|---|---|
| 2-135 | 4-CH₃ | 4-CH₃ | H | H | 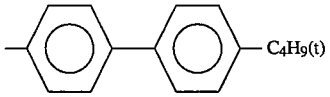 |
| 2-136 | 4-C₂H₅ | 4-C₂H₅ | H | H | 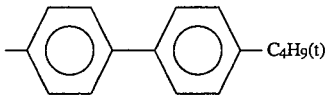 |
| 2-137 | 3-CH₃ | 3-CH₃ | 2-CH₃ | 2-CH₃ | 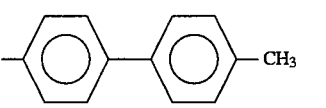 |
| 2-138 | 3-CH₃ | 3-CH₃ | H | H | 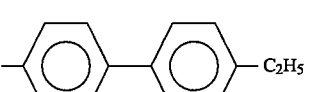 |
| 2-139 | H | H | 2-CH₃ | 2-CH₃ | 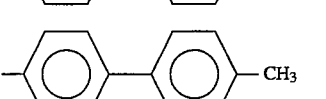 |
| 2-140 | H | H | 2-OCH₃ | 2-OCH₃ | 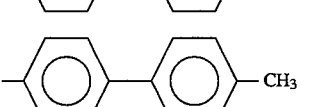 |
| 2-141 | 4-CH₃ | 3-CH₃ | H | H |  |
| 2-142 | 4-CH₃ | 4-OCH₃ | H | H |  |
| 2-143 | 4-CH₃ | 4-C₂H₅ | H | H |  |
| 2-144 | 3-CH₃ | H | H | H |  |
| 2-145 | 3-CH₃ | 4-OCH₃ | H | H | 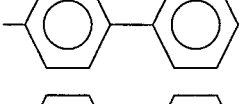 |
| 2-146 | 4-OCH₃ | 4-C₂H₅ | H | H | 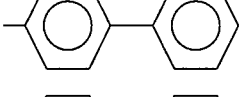 |
| 2-147 | 4-CH₃ | 4-C₂H₅ | H | H | 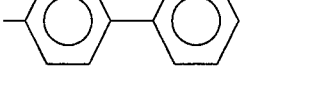 |
| 2-148 | H | H | H | H | 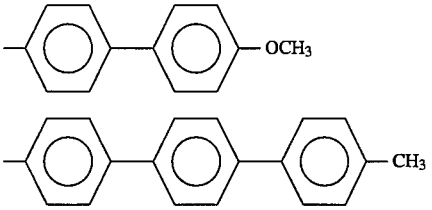 |

TABLE 3-continued
| Compounds No. | R¹ | R² | R³ | R⁴ | Ar |
|---|---|---|---|---|---|
| 2-149 | 4-CH₃ | 4-CH₃ | H | H | 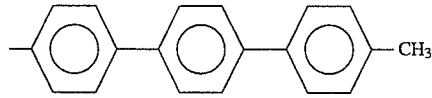 |
| 2-150 | 4-C₂H₅ | 4-C₂H₅ | H | H | 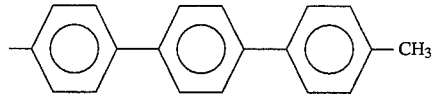 |
| 2-151 | 4-CH₃ | 4-CH₃ | H | H | 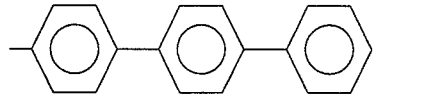 |
| 2-152 | 4-C₂H₅ | 4-C₂H₅ | H | H | 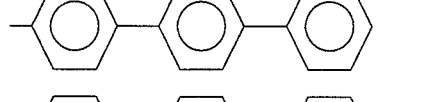 |
| 2-153 | 4-CH₃ | 4-CH₃ | H | H | 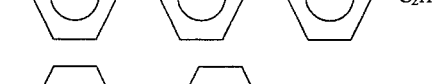 |
| 2-154 | H | H | H | H |  |
| 2-155 | 4-CH₃ | 4-CH₃ | H | H |  |
| 2-156 | 4-C₂H₅ | 4-C₂H₅ | H | H | 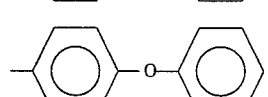 |
| 2-157 | 4-OCH₃ | 4-OCH₃ | H | H | 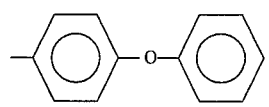 |
| 2-158 | 4-CH₃ | H | H | H | 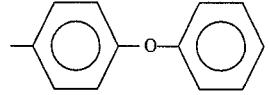 |
| 2-159 | 4-CH₃ | 4-OCH₃ | H | H | 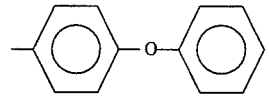 |
| 2-160 | 4-CH₃ | 4-CH₃ | H | H |  |
| 2-161 | 4-C₂H₅ | 4-C₂H₅ | H | H |  |

TABLE 3-continued
| Compounds No. | R¹ | R² | R³ | R⁴ | Ar |
|---|---|---|---|---|---|
| 2-162 | H | H | H | H | 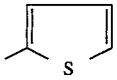 |
| 2-163 | 4-CH₃ | 4-CH₃ | H | H | 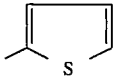 |
| 2-164 | 4-CH₃ | 4-CH₃ | H | H | 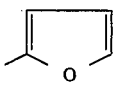 |
| 2-165 | 4-C₂H₅ | H | H | H | 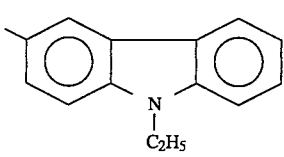 |
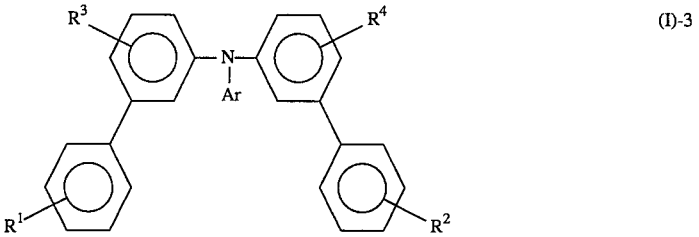  (I)-3
| 2-166 | H | H | H | H | 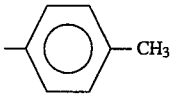 |
| 2-167 | H | H | H | H | 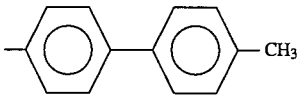 |
| 2-168 | H | H | H | H | 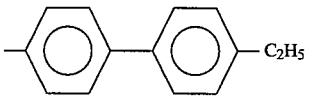 |
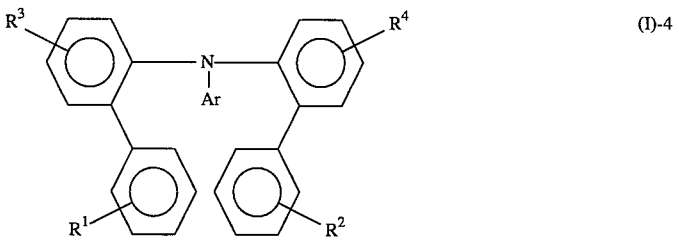  (I)-4
| 2-169 | H | H | H | H | 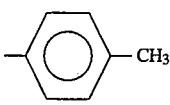 |
| 2-170 | H | H | H | H | 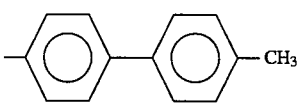 |

TABLE 3-continued

| Compounds No. | R¹ | R² | R³ | R⁴ | Ar |
|---|---|---|---|---|---|
| 2-171 | H | H | H | H | 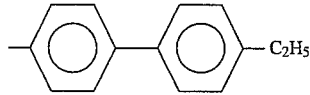 |

The following are examples of the procedure for the preparation of representative aminobiphenyl compounds in Table 3 for use in the present invention:

Preparation of Aminobiphenyl Compound No. 2-2 in Table 3

60 ml of nitrobenzene was added to a mixture of 8.82 g (30 mmol) of 4'-iodide-4-methyl-[1,1'-biphenyl], 1.61 g (15 mmol) of p-toluidine, 6.22 g of potassium carbonate, and 0.48 g of copper powder. The mixture was placed in an ester pipe and azeotropically heated for dehydration, with stirring, at 210° C. to 211° C. for 20 hours as a nitrogen gas was caused to flow over the reaction mixture.

The reaction mixture was then cooled to room temperature and filtered through a Celite filter to obtain a filtrate. The nitrobenzene was distilled away from the filtrate under reduced pressure. The residue was extracted with ether, washed with water, dried by use of magnesium sulfate, and condensed under reduced pressure, whereby a dark brown oily material was obtained.

The thus obtained product was subjected to a silica gel column chromatography by use of a toluene-n-hexane mixed solvent as an eluent, and recrystallized from a mixed solvent of ethanol and ethyl acetate, whereby 4'-methyl-N-( 4'-methyl-[1,1'-biphenyl]-4-yl)-N-(4-methylphenyl)-[1,1'-biphenyl] -4-amine was obtained in the form of colorless needles with a yield of 1.76 g (26.7%). The melting point of the product was 147.0° C. to 148° C.

The results of the elemental analysis of the thus obtained 4'-methyl-N-(4'-methyl-[1,1'-biphenyl]-4-yl-(4 -methylphenyl)-[1,1'-biphenyl]-4-amine (Aminobiphenyl Compound No. 2-2 in Table 3) were as follows:

|  | % C | % H | % N |
|---|---|---|---|
| Found | 90.28 | 6.69 | 3.02 |
| Calculated | 90.16 | 6.65 | 3.19 |

The above calculation was based on the formula for 4'-methyl-N-( 4'-methyl-[1,1'-biphenyl]-4-yl) -N-(4-methylphenyl)-[ 1,1'-biphenyl]-4-amine of $C_{33}H_{29}N$.

Figure 10:
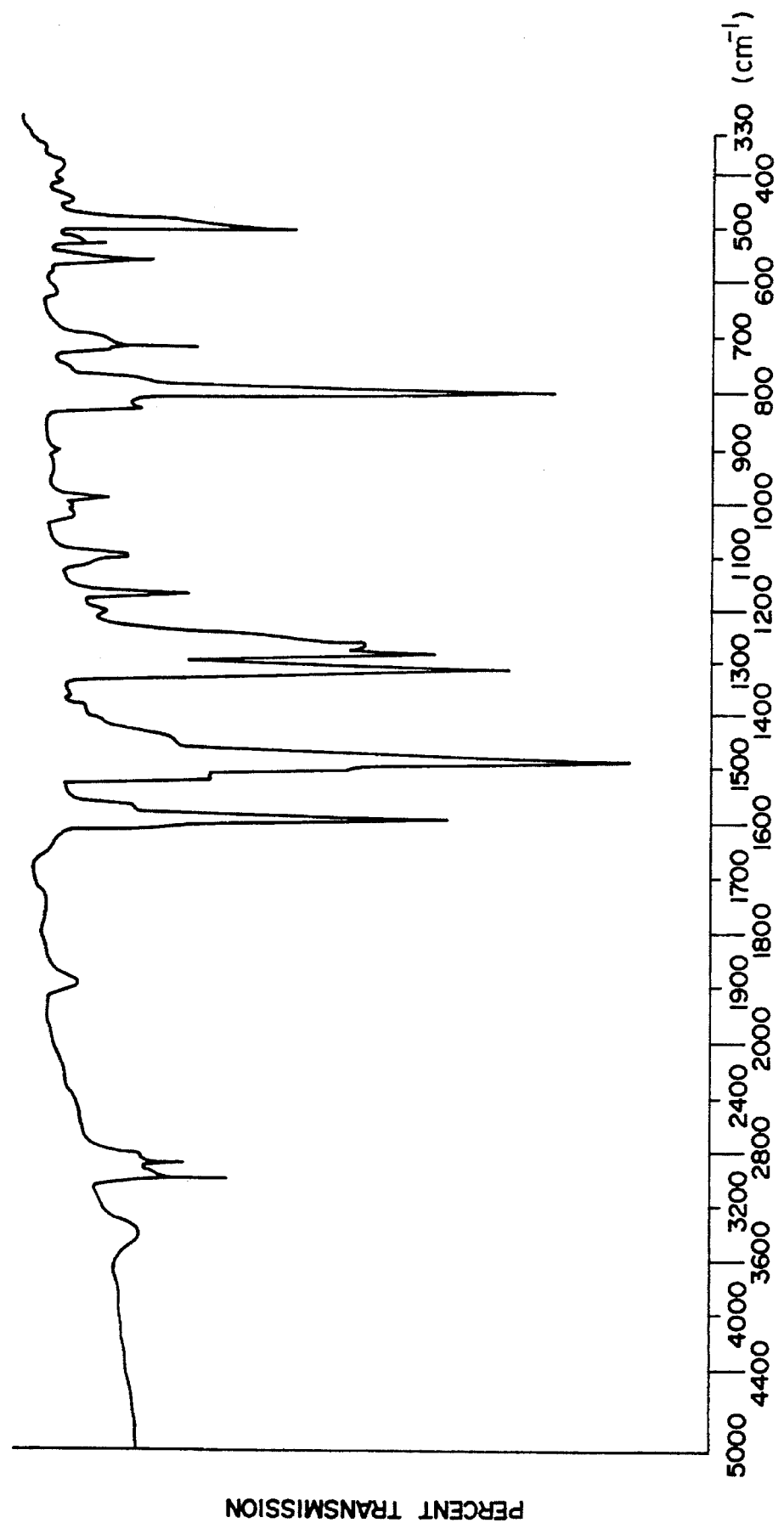
FIG. 10 is an infrared spectrum of an aminobiphenyl compound No. 2-2 for use in the present invention.

An infrared spectrum of the above product, taken by use of a KBr tablet, is shown in FIG. 10.

Preparation of Aminobiphenyl Compound No. 2-104 in Table 3

80 ml of nitrobenzene was added to a mixture of 2.12 g (12.5 mmol) of 4'-aminobiphenyl, 8.11 g (26.3 mmol) of 4-ethyl-4'-iodine-[1,1'-biphenyl], 3.65 g of potassium carbonate, and 0.1 mg of copper powder. The mixture was placed in an ester pipe and azeotropically heated for dehydration, with stirring, at 209° C. for 25 hours as a nitrogen gas was caused to flow over the mixture. The reaction mixture was then cooled to room temperature and filtered through a Celite filter to obtain a filtrate. The nitrobenzene was distilled away from the filtrate under reduced pressure. The residue was subjected to a silica gel column chromatography two times, first by use of toluene, and subsequently by a toluene-n-hexane mixed solvent as eluents, and recrystallized from a mixed solvent of ethanol and cyclohexane, whereby N,N-bis(4'-ethyl-[1,1'-biphenyl]- 4'-yl)-[1,1'-biphenyl]-4-amine (Aminobiphenyl Compound No. 2-104 in Table 3) was obtained in the form of colorless plates with a yield of 1.40 g (21.1%). The melting point of the product was 152.0° C. to 153.0° C.

The results of the elementals analysis of the thus obtained N,N-bis(4'-ethyl-[1,1'-biphenyl]-4'-yl)-[1,1' -biphenyl]-4-amine were as follows:

|  | % C | % H | % N |
|---|---|---|---|
| Found | 90.57 | 6.62 | 2.58 |
| Calculated | 90.68 | 6.67 | 2.64 |

The above calculation was based on the formula for N,N-bis(4' -ethyl-[1,1'-biphenyl]-4'-yl)-[1,1'-biphenyl]-4-amine of $C_{40}H_{35}N$.

Figure 11:
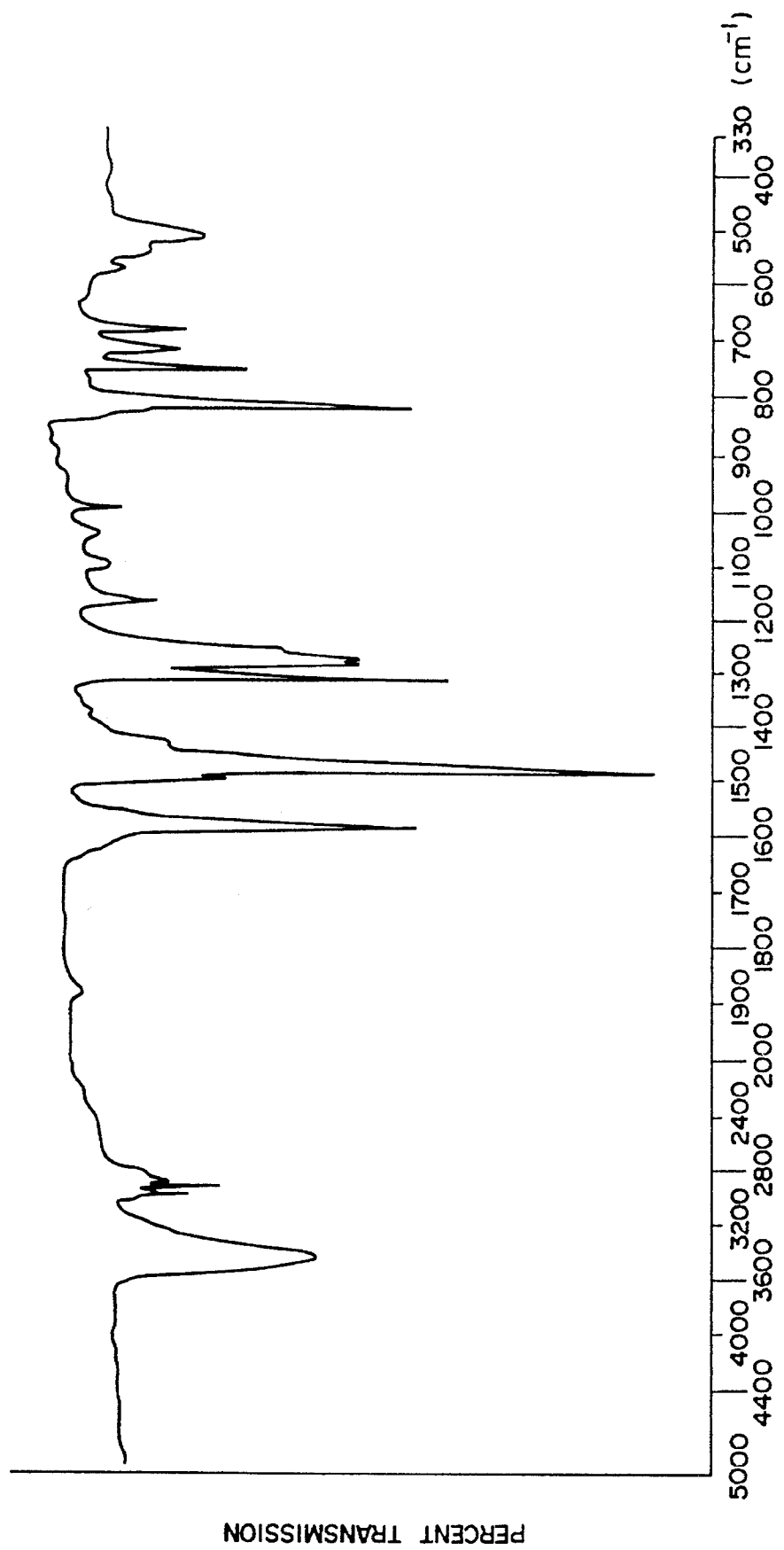
FIG. 11 is an infrared spectrum of an aminobiphenyl compound No. 2-104 for use in the present invention.

An infrared spectrum of the aove product, taken by use of a Far tablet, is shown in FIG. 11.

Preparation of Aminobiphenyl Compound No. 2-62 in Table 3

120 ml of nitrobenzene was added to a mixture of 14.92 g (0.100 mol) of p-acetotoluidine, 36.98 g (0.120 mol) of 4-ethyl-4'-iodine-[1,1'-biphenyl], 41.46 g of potassium carbonate, and 9.52 g of copper iodide. The mixture was placed in an ester pipe and azeotropically heated for dehydration, with stirring, at 213° C. to 214° C. for 8 hours as a nitrogen gas was caused to flow over the reaction mixture.

The reaction mixture was then cooled to room temperature and filtered through a Celite filter to obtain a filtrate. The nitrobenzene was distilled away from the filtrate under reduced pressure. The residue was extracted with toluene, washed with water, dried by use of magnesium sulfate, and condensed under reduced pressure, whereby a dark brown oily material was obtained.

The thus obtained product was subjected to a silica gel column chromatography by use of a toluene-n-hexane mixed solvent as an eluent, whereby N-acetyl-N-(4-methylphenyl)-4'-ethyl-[1,1'-biphenyl]-4-amine was obtained in the form of light brown crystals with a yield of 20.16 g (61.2%). The melting point of the product was 98.0° C. to 99.0° C.

To 19.96 g of the thus obtained N-acetyl-N-(4-methylphenyl)- 4'-ethyl-[1,1'-biphenyl]-4-amine were added 150 ml of ethanol and 150 ml of concentrated hydrochloric acid. The reaction mixture was refluxed with stirring for 7 hours and then added to 1 l of ice water. The reaction mixture was then extracted with toluene and the obtained organic portion was washed with water two times, with a saturated aqueous solution of sodium hydrogencarbonate one time, and then with water two times, and dried by use of magnesium sulfate, and condedsed under reduced pressure, whereby brown crystals were obtained. The thus obtained product was subjected to a silica gel column chromatography by use of toluene as an eluent, and recrystallized from a mixed solvent of n-hexane and toluene, whereby 4'-ethyl-N-(4-methylphenyl)-[1,1'-biphenyl]-4-amine (Aminobiphenyl Compound No. 2-62 in Table 3) was obtained in the form of colorless plates with a yield of 15.84 g (91.0%). The melting point of the product was 132.5° C. to 133.0° C.

To 4.31 g (15.0 mmol) of the thus obtained 4'-ethyl-N-(4-methylphenyl)-[1,1'-biphenyl]-4-amine were added 60 ml of nitrobenzene, 5.58 g (18.0 mmol) of 4'-iodine-4'-methoxy-[1,1'-biphenyl], 4.15 g of potassium carbonate, and 0.48 g of copper powder. The mixture was placed in an ester pipe and azeotropically heated for dehydration, with stirring, at 210° C. for 11 hours as a nitrogen gas was caused to flow over the mixture. The reaction mixture was then cooled to room tempereature and filtered through a Celite filter to obtain a filtrate. The nitrobenzene was distilled away from the filtrate under reduced pressure. The residue was extracted with toluene, washed with water, dried by use of magnesium sulfate, and condensed under reduced pressure, whereby orange brown crystals were obtained. The thus obtained product was subjected to a silica gel column chromatography by use of a mixed solvent of cyclohexane and toluene as an eluent, and recrystallized from a mixed solvent of ethanol and toluene, whereby 4'-ethyl-N-(4'-methoxy-[1,1'-biphenyl]-4-yl)-N-4-methylphenyl)-[1,1'-biphenyl]-4-amine (Aminobiphenyl Compound No. 2-62 in Table 3) was obtained in the form of colorless needles with a yield of 4.00 g (56.8%). The melting point of the product was 159.5° C. to 161.5° C.

The results of the elemental analysis of the thus obtained 4'-ethyl-N-(4'-methoxy-[1,1'-biphenyl]-4-yl)-N-(4-methylphenyl)-[1,1'-biphenyl]-4-amine were as follows:

|  | % C | % H | % N |
|---|---|---|---|
| Found | 87.00 | 6.62 | 2.78 |
| Calculated | 86.95 | 6.65 | 2.98 |

The above calculation was based on the formula for 4'-ethyl-N-(4'-methoxy-[1,1'-biphenyl]-4-yl)-N-(4-methylphenyl)-[1,1'-biphenyl]-4-amine of $C_{34}H_{31}N$.

Figure 12:
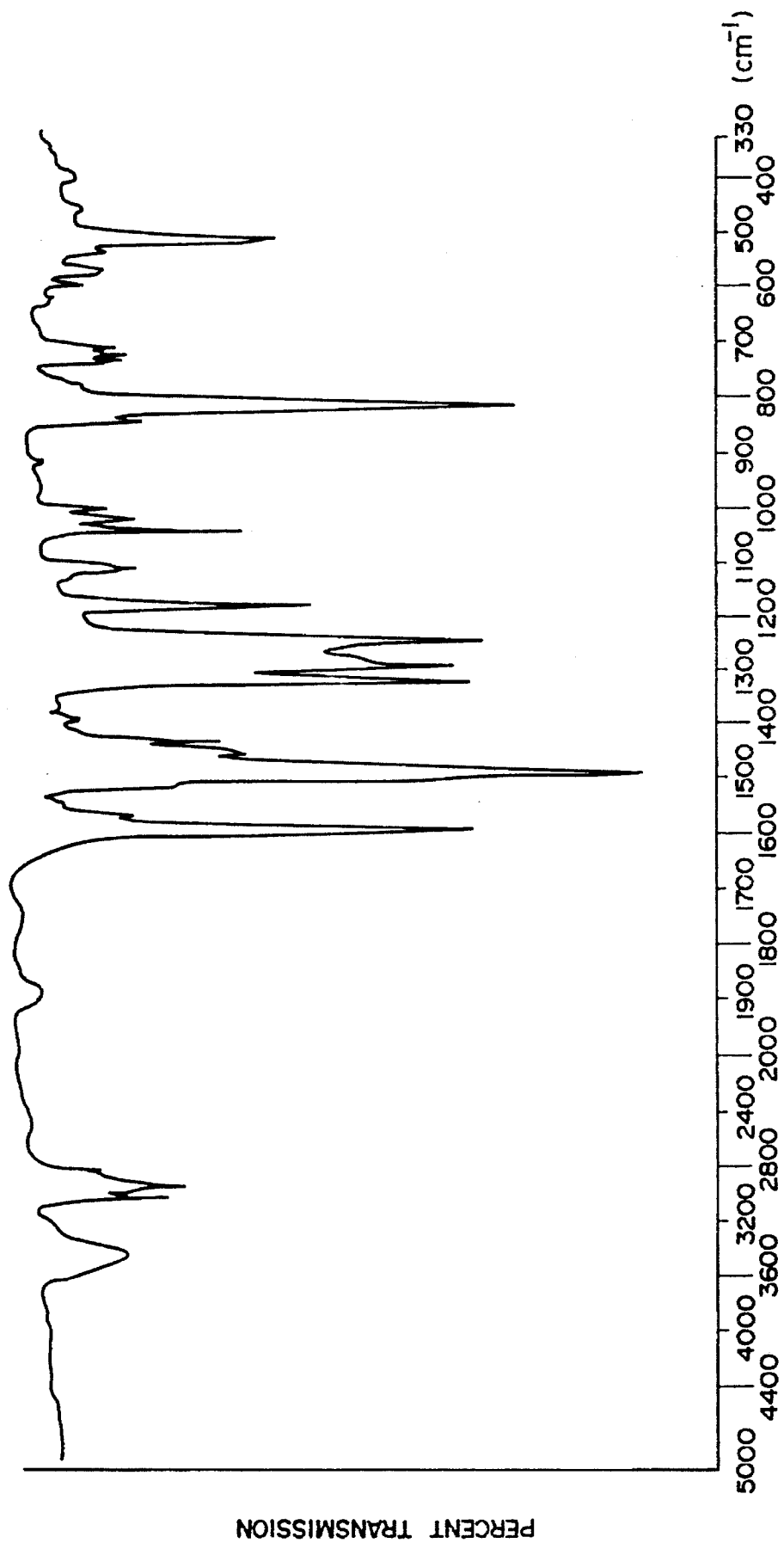
FIG. 12 is an infrared spectrum of an aminobiphenyl compound No. 2-62 for use in the present invention.

An infrared spectrum of the above product (Aminobiphenyl Compound No. 2-62 in Table 3), taken by use of a KBr tablet, is shown in FIG. 12.

The melting points and the results of elemental analysis of further examples of the aminobiphenyl compounds or use in the present invention are shown in Table 4.

TABLE 4

| Amino biphenyl Compound | Formula | Melting point (%) | Elemental Analysis Found (Calculated) | | |
|---|---|---|---|---|---|
|  |  |  | C % | H % | N % |
| No. 2-3 | $H_5C_2$—⌬—⌬—N(—⌬—⌬—$C_2H_5$)(—⌬—$CH_3$) | 125.0–126.0 | 90.08 (89.89) | 7.18 (7.11) | 2.87 (3.00) |
| No. 2-13 | $tC_4H_9$—⌬—⌬—N(—⌬—⌬—$tC_4H_9$)(—⌬—$CH_3$) | Oily | 89.62 (89.43) | 7.77 (7.89) | 2.54 (2.68) |
| No. 2-103 | $CH_3$—⌬—⌬—N(—⌬—⌬—$CH_3$)(—⌬—⌬) | 206.5–207.5 | 91.05 (90.98) | 6.23 (6.23) | 2.60 (2.80) |

TABLE 4-continued

| Amino biphenyl Compound | Formula | Melting point (°C) | Elemental Analysis Found (Calculated) | | |
|---|---|---|---|---|---|
| | | | C % | H % | N % |
| No. 2-107 | H₃CO—⌬—⌬—N(—⌬—⌬—OCH₃)—⌬—⌬ | 208.5–209.5 | 85.77 (85.52) | 5.91 (5.86) | 2.45 (2.62) |
| No. 2-106 | (t)C₄H₉—⌬—⌬—N(—⌬—⌬—ᵗC₄H₉)—⌬—⌬ | 190.5–192.0 | 90.34 (90.20) | 7.33 (7.41) | 2.21 (2.39) |
| No. 2-53 | ⌬—N(—⌬—⌬—C₂H₅)—⌬—CH₃ | 143.0–145.0 | 90.31 (90.02) | 6.77 (6.89) | 2.85 (3.09) |
| No. 2-52 | H₃C—⌬—⌬—N(—⌬—⌬—OCH₃)—⌬—CH₃ | 173.0–174.5 | 87.08 (87.00) | 6.40 (6.42) | 2.77 (3.08) |

The above listed novel aminobiphenyl compounds are useful as electrophotoconductive materials for use in electrophoto-graphic photoconductors and can be optically and/or chemically sensitized by dyes and Lewis acids. The above aminobiphenyl compounds are particularly useful as charge transporting materials for use in the so-called function-separation type photoconductors which include as charge generating materials organic pigments or inorganic pigments.

In the photoconductors according to the present invention, at least one aminobiphenyl compound of the formula (I) is contained in the photoconductive layers 2a, 2b, 2c, 2d and 2e. The aminobiphenyl compounds can be employed in different ways, for example, as shown in FIGS. 13 through 17.

Figure 13:
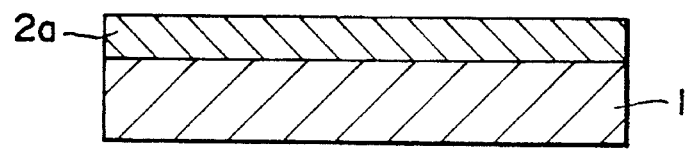
FIGS. 13 to 17 are enlarged schematic illustrations of embodiments of an electrophotographic photoconductor according to the present invention.

In the photoconductor as shown in FIG. 13, a photoconductive layer 2a is formed on an electroconductive support 1, which photoconductive layer 2a comprises an aminobiphenyl compound, a sensitizer dye and a binder agent. In this photoconductor, the aminobiphenyl compound works as a photoconductive material, through which charge carriers which are necessary for the light decay of the photoconductor are generated and transported. However, the aminobiphenyl compound itself scarcely absorbs light in the visible light range and, therefore, it is necessary to add a sensitizer dye which absorbs light in the visible light range in order to form latent electrostatic images by use of visible light.

Figure 14:
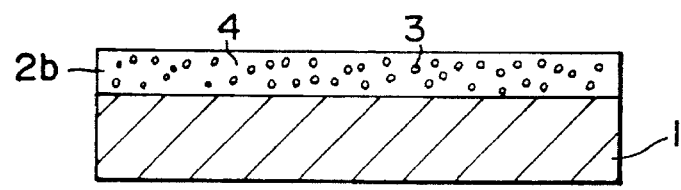

Referring to FIG. 14, there is shown an enlarged cross-sectional view of another embodiment of an electrophotographic photoconductor according to the present invention. In the figure, reference numeral 1 indicates an electroconductive support. On the electroconductive support 1, there is formed a photoconductive layer 2b comprising a charge generating material 3 dispersed in a charge transporting medium 4 comprising an aminobiphenyl compound and a binder agent. In this embodiment, the aminobiphenyl compound works as a charge transporting material; and the aminobiphenyl and the binder agent in combination constitute the charge transporting medium 4. The charge generating material 3, which is, for example, an inorganic or organic pigment, generates charge carriers. The charge transporting medium accepts the charge carriers generated by the charge generating material 3 and transports those charge carriers.

In this electrophotographic photoconductor, it is basically necessary that the light-absorption wavelength regions of the charge generating material 3 and the aminobiphenyl compound not overlap in the visible light range. This is because, in order that the charge generating material 3 produce charge carriers efficiently, it is necessary that light pass through the charge transporting medium 4 and reach the surface of the charge generating material 3. Since the aminobiphenyl compounds of the previously described general formula (I) do not substantially absorb light in the visible range, they can work effectively as charge transporting materials in combination with the charge generating material 3 which absorbs the light in the visible region and generates charge carriers.

Figure 15:
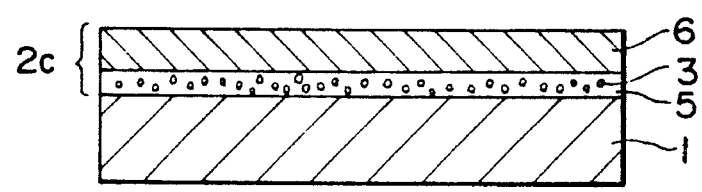

Referring to FIG. 15, there is shown an enlarged cross-sectional view of a further embodiment of an electrophotographic photoconductor according to the present invention. In the figure, there is formed on the electroconductive support 1 a two-layered photoconductive layer 2c comprising a charge generating layer 5 containing the charge generating material 3, and a charge transporting layer 6 containing an aminobiphenyl compound of the previously described formula (I).

In this photoconductor, light which has passed through the charge transporting layer 6 reaches the charge generating layer 5, and charge carriers are generated within the charge generating layer 5. The charge carriers which are necessary for the light decay for latent electrostatic image formation are generated by the charge generating material 3, accepted and transported by the charge transporting layer 6. In the charge transporting layer 6, the aminobiphenyl compound mainly works for transporting charge carriers. The generation and transportation of the charge carriers are performed by the same mechanism as that in the photoconductor shown in FIG. 14.

The electrophotographic photoconductor shown in FIG. 13, the charge generating layer 5 is formed on the charge transporting layer 5 containing the aminobiphenyl compound in the photoconductive layer 2d, thus the overlaying order of the charge generating layer 5 and the charge transporting layer 6 is reversed as compared with the electrophotographic photoconductor as shown in FIG. 12. The mechanism of the generation and transportation of charge carriers is substantially the same as that of the photoconductor shown in FIG. 15.

Figure 17:
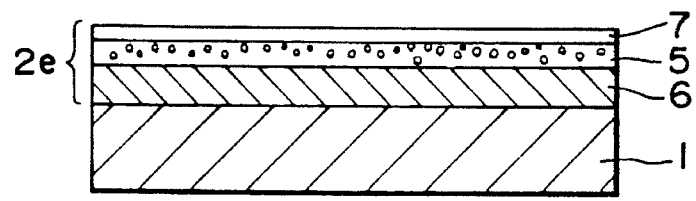

In the above photoconductor, a protective layer 7 may be formed on the charge generating layer 5 as shown in FIG. 17 for protecting the charge generating layer 5.

When the electrophotographic photoconductor according to the present invention as shown in FIG. 13 is prepared, at least one aminobiphenyl compound of the previously described formula (I) is dispersed in a binder resin solution, and a sensitizer dye is then added to the mixture, so that a photoconductive layer coating liquid is prepared. The thus prepared photoconductive layer coating liquid is coated on an electroconductive support 1 and dried, so that a photoconductive layer 2a is formed on the electroconductive support 1.

It is preferable that the thickness of the photosensitive layer 2a be in the range of 3 μm to 50 μm, more preferably in the range of 5 μm to 20 μm. It is preferable that the amount of the aminobiphenyl compound contained in the photoconductive layer 2a be in the range of 30 wt. % to 70 wt. % of the total weight of the photoconductive layer 2a, more preferably about 50 wt. % of the total weight of the photoconductive layer 2a. Further, it is preferable that the amount of the sensitizer dye contained in the photoconductive layer 2a be in the range of 0.1 wt. % to 5 wt. %, more preferably in the range of 0.5 wt. % to 3 wt. %, of the total weight of the photoconductive layer 2a.

As the sensitizer dye, the following can be employed in the present invention: Triarylmethane dyes, such as Brilliant Green, Victoria Blue B, Methyl Violet, Crystal Violet, and Acid Violet 6B; xanthene dyes, such as Rhodamine B, Rhodamine 6G, Rhodamine G Extra, Eosin S, Erythrosin, Rose Bengale, and Fluorescein; thiazine dyes, such as Methylene Blue; cyanin dyes, such as cyanin; and pyrylium dyes, such as 2,6-diphenyl-4-(N,N-dimethylaminophenyl) thiapyrylium perchlorate and benzopyrylium salt (Japanese Patent Publication 48-25658); and 2,4,7-trinitro-9-fluorenone and 2,4-dinitro-9-fluorenone. These sensitizer dyes can be used alone or in combination.

An electrophotographic photoconductor according to the present invention as shown in FIG. 11 can be prepared, for example, as follows. A charge generating material in the form of small particles is dispersed in a solution of one or more aminobiphenyl compounds and a binder agent. The thus prepared dispersion is coated on the electroconductive support 1 and then dried, whereby a photoconductive layer 2b is formed on the electroconductive support 1.

It is preferable that the thickness of the photoconductive layer 2b be in the range of 3 μm to 50 μm, more preferably in the range of 5 μm to 20 μm. It is preferable that the amount of the aminobiphenyl compound contained in the photoconductive layer 2b be in the range of 10 wt. % to 95 wt. %, more preferably in the range of 30 wt. % to 90 wt. %, of the total weight of the photoconductive layer 2b. Further, it is preferable that the amount of the charge generating material 3 contained in the photoconductive layer 2b be in the range of 0.1 wt. % to 50 wt. %, more preferably in the range of 1 wt. % to 20 wt. %, of the total weight of the photoconductive layer 2b.

As the charge generating material 3, the following can be employed in the present invention: Inorganic pigments, such as selenium, a selenium-tellurium alloy, cadmium sulfide, a cadmium sulfide-selenium alloy, and α-silicon; and organic pigments, for example, C.I. Pigment Blue 25 (C.I. 21180), C.I. Pigment Red 41 (C.I. 21200), C.I. Acid Red 52 (C.I. 45100), and C.I. Basic Red 3 (C.I. 45210); azo pigments having a carbazole skeleton (Japanese Laid-Open Patent Application 53-95033), azo pigments having a distyrylbenzene skeleton (Japanese Laid-Open Patent Application 53-133445), azo pigments having a triphenylamine skeleton (Japanese Laid-Open Patent Application 53-132347), azo pigments having a dibenzothiophene skeleton (Japanese Laid-Open Patent Application 54-21728), azo pigments having an oxazole skeleton (Japanese Laid-Open Patent Application 54-12742), azo pigments having a fluorenone skeleton (Japanese Laid-Open Patent Application 54-22834), azo pigments having a bisstilbene skeleton (Japanese Laid-Open Patent Application 54-17733), azo pigments having a distyryl oxadiazole skeleton (Japanese Laid-Open Patent Application 54-2129), azo pigments having a distyryl carbazole skeleton (Japanese Laid-Open Patent Application 54-14967); Phthalocyanine-type pigments such as C.I. Pigment Blue 16 (C.I. 74100); Indigo-type pigments such as C.I. Vat Brown 5 (C.I. 73410) and C.I. Vat Dye (C.I. 73030);

and perylene-type pigments, such as Algo Scarlet B (made by Bayer Co., Ltd.) and Indanthrene Scarlet R (made by Bayer Co., Ltd). These charge generating materials can be used alone or in combination.

An electrophotographic photoconductor according to the present invention as shown in FIG. 15 can be prepared, for example, as follows. A charge generating material 3 is vacuum-evaporated on the electroconductive support 1, whereby a charge generating layer 5 is formed. Alternatively, a charge generating material 3 in the form of fine particles is dispersed in a solution of a binder agent, and this dispersion is applied to the electroconductive support material 1 and then dried, and, if necessary, the applied layer is subjected to buffing to make the surface smooth or to adjust the thickness of the layer to a predetermined thickness, whereby a charge generating layer 5 is formed. A charge transporting layer 6 is then formed on the charge generating layer 5 by applying a solution of one or more aromatic diethyl compounds and a binder agent to the charge generating layer 5 and then drying the applied solution. In this photoconductor, the charge generating material employed is the same as that employed in the photoconductor in FIG. 14.

It is preferable that the thickness of the charge generating layer 5 be 5 μm or less, more preferably 2 μm or less. It is preferable than the thickness of the charge transporting layer 6 be in the range of 3 μm to 50 μm, more preferably in the range of 5 μm to 20 μm. In the case where the charge generating layer 5 comprises a charge generating material in the form of fine particles, dispersed in a binder agent, it is preferable that the amount of the charge generating material in the charge generating layer 5 be in the range of 10 wt. % to 95 wt. %, more preferably in the range of about 50 wt. % to about 90 wt. % of the entire weight of the charge generating layer 5. Further, it is preferable that the amount of the aminobiphenyl compound contained in the charge transporting layer 6 be in the range of 10 wt. % to 95 wt. %, more preferably in the range of 30 wt. % to 90 wt. %, of the total weight of the charge transporting layer 6.

Figure 16:
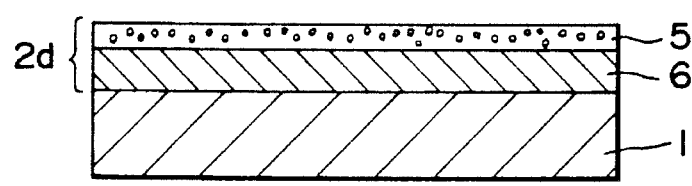

The electrophotographic photoconductor as shown in FIG. 16 can be prepared, for example, by coating a solution of the aminobiphenyl compound and a binder agent on the electroconductive support 1 and drying the same to form a charge transporting layer 4, and then coating on the charge transporting layer 4 a dispersion of finely-divided charge generating material, with addition thereto of a binder agent when necessary, and drying the coated dispersion to form a charge generating layer 5 on the charge transporting layer 4. The thickness of each of the two layers 4 and 5 and the compositions thereof may be the same as those of the photoconductive layer 2c in the photoconductor shown in FIG. 15.

When a protective layer 7 is formed on the charge generating layer 5 of the photoconductive layer by coating an appropriate resin solution, for instance, by performing spray coating, the photoconductor as shown in FIG. 17 can be prepared.

As the electroconductive support 1 for use in the present invention, a metal plate or metal foil, for example, made of aluminum, a plastic film on which a metal, for example, aluminum, is evaporated, or paper which has been treated so as to be electroconductive, can be employed.

As the binder agent for use in the present invention, condensation resins, such as polyamide, polyurethane polyester, epoxy resin, polyketone and polycarbonate; and vinyl polymers such as polyvinylketone, polystyrene, poly-N-vinylcarbazole and polyacrylamide, can be used. These resins can also be employed as a resin component in the above mentioned protective layer 7.

Other conventional electrically insulating and adhesive resins can also be used as the binder agent in the present invention. When necessary, there can be added to the binder resins a plasticizer, for example, halogenated paraffin, polybiphenyl chloride, dimethylnaphthalene and dibutyl phthalate.

In the above described photoconductors according to the present invention, if necessary, an adhesive or barrier layer can be interposed between the electroconductive support and the photoconductive layer. The adhesive layer or the barrier layer can be made of, for example, polyamide, nitrocellulose, or aluminum oxide. It is preferable that the thickness of the adhesive layer or barrier layer be 1 μm or less.

When copying is performed by use of the photoconductors according to the present invention, the surface of the photoconductor is charged uniformly in the dark to a predetermined polarity. The uniformly charge photoconductor is exposed to a light image so that a latent electrostatic image is formed on the photoconductor. The thus formed latent electrostatic image is developed by a developer to a visible image, and, when necessary, the developed image can be transferred to a sheet of paper. The photoconductors according to the present invention have high photosensitivity and excellent flexibility.

Preparation of embodiments of an electrophotographic photoconductor according to the present invention will now be explained in detail by referring to the following examples.

EXAMPLE P-1-1

The following components were ground and dispersed in a ball mill to prepare a charge generating layer coating liquid:

|  | Parts by Weight |
| --- | --- |
| Diane Blue (C.I. Pigment Blue 25, C.I. 21180) (a charge generating pigment of the following formula (CG-1)) | 76 |

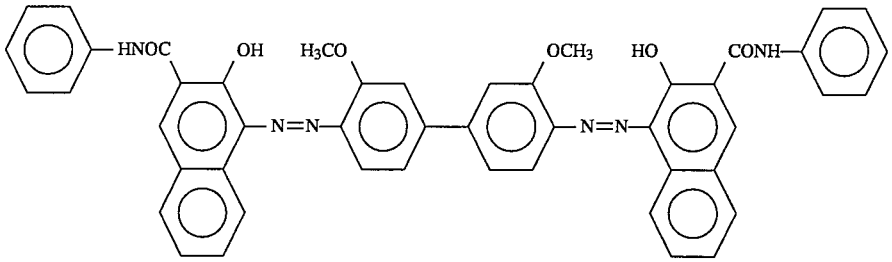

|  | Parts by Weight |
| --- | --- |
| 2% tetrahydrofuran solution of a polyester resin (Vylon 200 made by Toyobo Co., Ltd.) | 1,260 |
| Tetrahydrofuran | 3,700 |

This charge generating layer coating liquid was coated by a doctor blade on the aluminum-evaporated surface of an aluminum-evaporated polyester base film, which served as an electroconductive support, so that a charge generating layer was formed on the electroconductive support with a thickness of about 1 μm when dried at room temperature.

Then the following components were mixed and dissolved, so that a charge transporting layer coating liquid was prepared:

|  | Parts by Weight |
| --- | --- |
| Aminobiphenyl compound No. 1–21 in Table 1 | 2 |
| Polycarbon resin (Panlite K 1300 made by Teijin Limited.) | 2 |
| Tetrahydrofuran | 16 |

The thus prepared charge transporting layer coating liquid was coated on the aforementioned charge generating layer by a doctor blade and dried at 80° C. for 2 minutes and then at 105° C. for 5 minutes, so that a charge transporting layer with a thickness of about 20 μm was formed on the charge generating layer; thus, an electrophotographic photoconductor No. 1-1 according to the present invention was prepared.

The electrophotographic photoconductor No. 1 was charged negatively in the dark under application of −6 kV of corona charge for 20 seconds and then allowed to stand in the dark for 20 seconds without applying any charge thereto. At this moment, the surface potential $V_{po}$ (V) of the photoconductor was measured by a Paper Analyzer (Kawaguchi Electro Works, Model SP-428). The photoconductor was then illuminated by a tungsten lamp in such a manner that the illuminance on the illuminated surface of the photoconductor was 20 lux, and the exposure $E_{1/2}$ (lux.seconds) required to reduce the initial surface potential $V_{po}$ (V) to ½ the initial surface potential $V_{po}$ (V) was measured. The results showed that $V_{po}(V)=-1100$ V and $E_{1/2}=1.62$ lux.seconds.

EXAMPLES P-1-2 through P-1-27

Example P-1-1 was repeated except that the charge generating material and the aminobiphenyl compound working as the charge transporting material employed in Example P-1-1 were respectively replaced by the charge generating materials and the aminodiphenyl compounds as listed in Table 3, whereby electrophotographic photoconductors No. 1-2 through No. 1-27 according to the present invention were prepared.

TABLE 5

| Photo-Conductor | Charge Generating Material | Charge Transporting Material (Aminobiphenyl compound in Table 1) |
| --- | --- | --- |
| No. 1-2 | 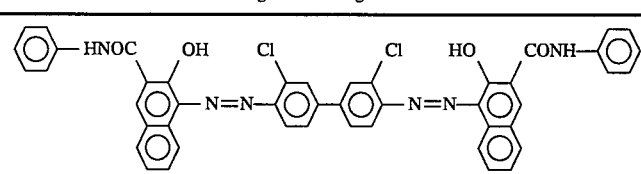<br>CG-2 | No. 1-21 |

TABLE 5-continued

| Photo-Conductor | Charge Generating Material | Charge Transporting Material (Aminobiphenyl compound in Table 2) |
|---|---|---|
| No. 1-3 | CG-3 | No. 1-21 |
| No. 1-4 | CG-4 | No. 1-21 |
| No. 1-5 | CG-5 | No. 1-21 |
| No. 1-6 | CG-6 | No. 1-21 |
| No. 1-7 | β-type copper phthalocyanine | No. 1-2 |
| No. 1-8 | CG-7 | No. 1-2 |
| No. 1-9 | CG-2 | 2 |
| No. 1-10 | CG-3 | 2 |
| No. 1-11 | CG-5 | 2 |
| No. 1-12 | CG-3 | 20 |
| No. 1-13 | CG-5 | 20 |

TABLE 5-continued

| | | |
|---|---|---|
| No. 1-14 | CG-3 | 3 |
| No. 1-15 | CG-5 | 3 |
| No. 1-16 | CG-3 | 22 |
| No. 1-17 | CG-5 | 22 |
| No. 1-18 | CG-3 | 30 |
| No. 1-19 | CG-5 | 30 |
| No. 1-20 | CG-3 | 34 |
| No. 1-21 | CG-5 | 34 |
| No. 1-22 | CG-3 | 8 |
| No. 1-23 | CG-5 | 8 |
| No. 1-24 | CG-3 | 28 |
| No. 1-25 | CG-5 | 28 |
| No. 1-26 | CG-3 | 36 |
| No. 1-27 | CG-5 | 36 |
| No. 1-28 | CG-3 | 37 |
| No. 1-29 | CG-5 | 37 |
| No. 1-30 | CG-3 | 39 |
| No. 1-31 | CG-5 | 39 |
| No. 1-32 | CG-3 | 48 |
| No. 1-33 | CG-5 | 48 |
| No. 1-34 | CG-3 | 62 |
| No. 1-35 | CG-5 | 62 |
| No. 1-36 | CG-3 | 63 |
| No. 1-37 | CG-5 | 63 |
| No. 1-38 | CG-3 | 64 |
| No. 1-39 | CG-5 | 64 |
| No. 1-40 | CG-3 | 66 |
| No. 1-41 | CG-5 | 66 |
| No. 1-42 | CG-3 | 104 |
| No. 1-43 | CG-5 | 104 |
| No. 1-44 | CG-3 | 105 |
| No. 1-45 | CG-5 | 105 |
| No. 1-46 | CG-3 | 106 |
| No. 1-47 | CG-5 | 106 |
| No. 1-48 | CG-3 | 108 |
| No. 1-49 | CG-5 | 108 |

EXAMPLE P-1-50

Selenium was vacuum-evaporated with a thickness of about 1.0 μm on an about 300 μm thick aluminum plate so that a charge generating layer was formed on the aluminum plate.

A charge transporting layer coating liquid was prepared by mixing and dispersing the following components:

| | Parts by Weight |
|---|---|
| Aminobiphenyl compound No. 1-21 in Table 1 | 2 |
| Polyester resin (Polyester Adhesive 49000 made by Du Pont Co.) | 3 |
| Tetrahydrofuran | 45 |

The thus prepared charge transporting layer coating liquid was coated on the aforementioned selenium charge generating layer by a doctor blade, dried at room temperature and further dried under reduced pressure, so that a charge transporting layer about 10 μm thick was formed on the charge generating layer; thus, an electrophotographic photoconductor No. 1-50 according to the present invention was prepared.

EXAMPLE P-1-51

A perylene pigment C.I. Vat Red 23 (C.I. 71130) of the following formula was vacuum-evaporated with a thickness of about 0.3 μm on an about 300 μm thick aluminum plate so that a charge generating layer was formed on the aluminum plate:

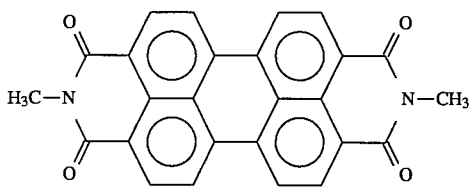

A charge transporting layer coating liquid was prepared by mixing and dispersing the following components:

| | Parts by Weight |
|---|---|
| Aminobiphenyl compound No. 1-21 in Table 1 | 2 |
| Polyester resin (Polyester Adhesive 49000 made by Du Pont Co.) | 3 |
| Tetrahydrofuran | 45 |

The thus prepared charge transporting layer coating liquid was coated on the aforementioned charge generating layer by a doctor blade, dried at room temperature and further dried under reduced pressure, so that a charge transporting layer about 10 μm thick was formed on the charge generating layer; thus, an electrophotographic photoconductor No. 1-51 according to the present invention was prepared.

EXAMPLE P-1-52

One part by weight of Diane Blue (C.I. Pigment Blue 25, C.I. 21180) which was the same as that employed in Example P-1 was added to 158 parts by weight of tetrahydrofuran, and the mixture was ground and dispersed in a ball mill. To this mixture, 12 parts by weight of the aminobiphenyl compound No. 1-21 in Table 1 and 18 parts by weight of a polyester resin (Polyester Adhesive 49000 made by Du Pont Co.) were added and mixed, whereby a photoconductive layer coating liquid was prepared.

The thus prepared photoconductive layer coating liquid was coated on an aluminum-evaporated polyester film by a doctor blade and dried at 100° C. for 30 minutes so that a photoconductive layer with a thickness of about 16 μm was formed on the aluminum-evaporated polyester film, thus, an electrophotographic photoconductor No. 1-52 according to the present invention was prepared.

EXAMPLE P-1-53

The same charge transporting layer coating liquid as that prepared in Example 1 was coated by a doctor blade on the aluminum-evaporated surface of an aluminum-evaporated polyester base film, which served as an electroconductive support, so that a charge transporting layer was formed on the electroconductive support, with a thickness of about 20 μm when dried at room temperature.

Then the following components were ground and dispersed in a ball mill to prepare a dispersion:

thickness of about 0.2 μm was formed on the charge transporting layer. Then a methanol/n-buthanol solution of a polyaminde resin (Trademark "CM-8000" made by Toray Industries, Inc.) was coated on the charge generating layer by spray coating and dried at 120° C. for 30 minutes, whereby a protective layer having a thickness of about 0.5 μm was formed on the charge generating layer. Thus an electrophotographic photoconductor No. 1-53 according to the present invention was prepared.

The thus prepared electrophotographic photoconductors No. 1-2 to No. 1-53 were charged negatively or positively in the dark under application of −6 kV or +6 kV of corona charge for 20 seconds and then allowed to stand in the dark for 20 seconds without applying any charge thereto. At this moment, the surface potential $V_{po}$ (V) of each photoconductor was measured by a Paper Analyzer (Kawaguchi Electro Works, Model SP-428). Each photoconductor was then illuminated by a tungsten lamp in such a manner that the illuminance on the illuminated surface of the photoconductor was 20 lux, so that the exposure $E_{1/2}$ (lux seconds) required to reduce the initial surface potential $V_{po}$ (V) to ½ the initial surface potential $V_{po}$ (V) was measured.

The results are shown in Table 6.

TABLE 6

| Photoconductors | $V_{po}$ (volt) | $E_{1/2}$ (lux sec) |
|---|---|---|
| 1-1 | −1100 | 1.62 |
| 1-2 | −1210 | 1.50 |
| 1-3 | −1310 | 0.80 |
| 1-4 | −1520 | 2.41 |
| 1-5 | −1190 | 0.62 |
| 1-6 | −990 | 0.91 |
| 1-7 | −1220 | 2.00 |

| | Parts by Weight |
|---|---|
| Bisazo Pigment (a charge generating pigment of the following formula (CG-5)) | 13.5 |
| Polyvinyl butyral (Trademark "XYHL" made by Union Carbide Plastic Co., Ltd.) | 5.4 |
| Tetrahydrofuran | 680 |
| Ethyl cellosolve | 1020 |

To the above dispersion, 1700 parts by weight of ethyl cellosolve were further added and the mixture was dispersed, whereby a charge generating layer-coating liquid was prepared. The thus prepared charge generating layer coating liquid was coated on the aforementioned charge transporting layer by spray coating and dried at 100° C. for 10 minutes, whereby a charge generating layer having a TABLE 6-continued

| Photoconductors | $V_{po}$ (volt) | $E_{1/2}$ (lux sec) |
|---|---|---|
| 1-8 | −1420 | 1.87 |

TABLE 6-continued

| Photoconductors | Vpo (volt) | $E_{1/2}$ (lux sec) |
|---|---|---|
| 1-9 | -1120 | 1.32 |
| 1-10 | -1200 | 1.03 |
| 1-11 | -1150 | 0.98 |
| 1-12 | -1080 | 1.10 |
| 1-13 | -1290 | 0.92 |
| 1-14 | -1450 | 1.10 |
| 1-15 | -1110 | 1.04 |
| 1-16 | -1270 | 0.91 |
| 1-17 | -1090 | 0.64 |
| 1-18 | -1250 | 1.11 |
| 1-19 | -1240 | 1.04 |
| 1-20 | -1230 | 0.85 |
| 1-21 | -1050 | 0.69 |
| 1-22 | -1320 | 1.09 |
| 1-23 | -800 | 0.82 |
| 1-24 | -1300 | 1.07 |
| 1-25 | -690 | 0.68 |
| 1-26 | -1140 | 1.00 |
| 1-27 | -1140 | 0.94 |
| 1-28 | -1260 | 1.06 |
| 1-29 | -650 | 0.73 |
| 1-30 | -1180 | 1.05 |
| 1-31 | -1250 | 1.10 |
| 1-32 | -1160 | 0.15 |
| 1-33 | -1210 | 1.12 |

TABLE 6-continued

| Photoconductors | Vpo (volt) | $E_{1/2}$ (lux sec) |
|---|---|---|
| 1-34 | -1220 | 1.11 |
| 1-35 | -1020 | 1.03 |
| 1-36 | -1280 | 1.04 |
| 1-37 | -980 | 0.84 |
| 1-38 | -1470 | 1.18 |
| 1-39 | -1000 | 0.94 |
| 1-40 | -1000 | 0.98 |
| 1-41 | -450 | 0.53 |
| 1-42 | -1130 | 1.05 |
| 1-43 | -1180 | 1.19 |
| 1-44 | -1220 | 1.03 |
| 1-45 | -1240 | 1.08 |
| 1-46 | -1200 | 1.00 |

TABLE 6-continued

| Photoconductors | Vpo (volt) | $E_{1/2}$ (lux sec) |
|---|---|---|
| 1-47 | -1220 | 1.17 |
| 1-48 | -1100 | 0.99 |
| 1-49 | -770 | 0.81 |
| 1-50 | -970 | 2.60 |
| 1-51 | -1520 | 3.98 |
| 1-52 | +1320 | 1.90 |
| 1-53 | +1290 | 0.99 |

Each of the above electrophotographic photoconductors No. 1-1 through No. 1-53 was incorporated in a commercially available electrophotographic copying machine and a latent electrostatic image was formed thereon by being exposed to a light image. The latent electrostatic image was developed with a dry type developer to a visible toner image, electrostatically transferred to a transfer sheet made plain paper and fixed thereto. As=a result, a clear transferred image was obtained by each of the photoconductors. When a liquid developer was employed instead of the dry type developer, clear transfer images were obtained likewise.

EXAMPLE P-2-1

The following components were ground and dispersed in a ball mill to prepare a charge generating layer coating liquid:

| | Parts by Weight |
|---|---|
| Diane Blue (C.I. Pigment Blue 25, C.I. 21180) (a charge generating pigment of the following formula (CG-1)) | 76 |

(CG-1)

[Chemical structure: Ph-HNOC, OH, H₃CO, OCH₃, HO, CONH-Ph with two N=N azo linkages bridging naphthalene and biphenyl units]

| | |
|---|---|
| 2% tetrahydrofuran solution of a polyester resin (Vylon 200 made by Toyobo Co., Ltd.) | 1,260 |
| Tetrahydrofuran | 3,700 |

This charge generating layer coating liquid was coated by a doctor blade on the aluminum-evaporated surface of an aluminum-evaporated polyester base film, which served as an electroconductive support, so than a charge generating layer was formed on the electroconductive support with a thickness of about 1 μm when dried an room temperature.

The following components were then mixed and dissolved, so that a charge transporting layer coating liquid was prepared:

| | Parts by Weight |
|---|---|
| Aminobiphenyl compound No. 2-2 in Table 13 | 2 |
| Polycarbonate resin (Panlite K 1300 | 2 |

| | Parts by Weight |
|---|---|
| made by Teijin Limited.) | |
| Tetrahydrofuran | 16 |

The thus prepared charge transporting layer coating liquid was coated on the aforementioned charge generating layer by a doctor blade and dried at 80° C. for 2 minutes and then at 105° C. for 5 minutes, so that a charge transporting layer with a thickness of about 20 μm was formed on the charge generating layer; thus, an electrophotographic photoconductor No. 2-1 according to the present invention was prepared.

The electrophotographic photoconductor No. 2-1 was charged negatively in the dark under application of −6 kV of corona charge for 10 seconds and then allowed to stand in the dark for 20 seconds without applying any charge thereto. At this moment, the surface potential $V_{po}$ (V) of the photoconductor was measured by a Paper Analyzer (Kawaguchi Electro Works, Model SP-428). The photoconductor was then illuminated by a tungsten lamp in such a manner that the illuminance on the illuminated surface of the photoconductor was 4.5 lux, and the exposure $E_{1/2}$ (lux seconds) required to reduce the initial surface potential $V_{po}$ (V) to ½ the initial surface potential $V_{po}$ (V) was measured. The results showed that $V_{po}$ (V)=−1113 V and $E_{1/2}$=1.72 lux-.seconds.

EXAMPLES P-2-2 through P-2-27

Example P-2-1 was repeated except that the charge generating material and the aminobiphenyl compound working as the charge transporting material employed in Example P-2-1 were respectively replaced by the charge generating materials and the aminobiphenyl compounds as listed in Table 6, whereby electrophotographic photoconductors No. 2-2 through No. 2-27 according to the present invention were prepared.

TABLE 7

| Photo-Conductor | Charge Generating Material | Charge Transporting Material (Aminobiphenyl compound in Table 3) |
|---|---|---|
| No. 2-2 | CG-2 | No. 2-2 |
| No. 2-3 | CG-3 | No. 2-2 |
| No. 2-4 | CG-4 | No. 2-2 |

| Photo-Conductor | Charge Generating Material | Charge Transporting Material (Aminobiphenyl compound in Table 2) |
|---|---|---|

TABLE 7-continued

| No. 2-5 | CG-5 | No. 2-2 |
|---|---|---|
| No. 2-6 | CG-6 | No. 2-2 |
| No. 2-7 | β-type copper phthalocyanine | No. 2-2 |
| No. 2-8 | CG-7 | No. 2-3 |
| No. 2-9 | CG-2 | No. 2-3 |
| No. 2-10 | CG-3 | No. 2-3 |
| No. 2-11 | CG-5 | No. 2-3 |
| No. 2-12 | CG-3 | No. 2-53 |
| No. 2-13 | CG-5 | No. 2-53 |
| No. 2-14 | CG-3 | No. 2-54 |
| No. 2-15 | CG-5 | No. 2-54 |
| No. 2-16 | CG-3 | No. 2-62 |
| No. 2-17 | CG-5 | No. 2-62 |
| No. 2-18 | CG-3 | No. 2-103 |
| No. 2-19 | CG-5 | No. 2-103 |
| No. 2-20 | CG-3 | No. 2-104 |
| No. 2-21 | CG-5 | No. 2-104 |
| No. 2-22 | CG-3 | No. 2-106 |
| No. 2-23 | CG-5 | No. 2-106 |
| No. 2-24 | CG-3 | No. 2-4 |
| No. 2-25 | CG-5 | No. 2-4 |
| No. 2-26 | CG-3 | No. 2-8 |
| No. 2-27 | CG-5 | No. 2-8 |
| No. 2-28 | CG-3 | No. 2-21 |
| No. 2-29 | CG-5 | No. 2-21 |
| No. 2-30 | CG-3 | No. 2-22 |
| No. 2-31 | CG-5 | No. 2-22 |
| No. 2-32 | CG-3 | No. 2-25 |
| No. 2-33 | CG-5 | No. 2-25 |
| No. 2-34 | CG-3 | No. 2-30 |
| No. 2-35 | CG-5 | No. 2-30 |
| No. 2-36 | CG-3 | No. 2-31 |
| No. 2-37 | CG-5 | No. 2-31 |
| No. 2-38 | CG-3 | No. 2-50 |
| No. 2-39 | CG-5 | No. 2-50 |
| No. 2-40 | CG-3 | No. 2-49 |
| No. 2-41 | CG-5 | No. 2-49 |
| No. 2-42 | CG-3 | No. 2-72 |
| No. 2-43 | CG-5 | No. 2-72 |
| No. 2-44 | CG-3 | No. 2-90 |
| No. 2-45 | CG-5 | No. 2-90 |
| No. 2-46 | CG-3 | No. 2-115 |
| No. 2-47 | CG-5 | No. 2-115 |
| No. 2-48 | CG-3 | No. 2-110 |

TABLE 7-continued

| No. 2-49 | CG-5 | No. 2-110 |
| No. 2-50 | CG-3 | No. 2-97 |
| No. 2-51 | CG-5 | No. 2-97 |
| No. 2-52 | CG-3 | No. 2-142 |
| No. 2-53 | CG-5 | No. 2-142 |
| No. 2-54 | CG-3 | No. 2-143 |
| No. 2-55 | CG-5 | No. 2-143 |

EXAMPLE P-2-56

Selenium was vacuum-evaporated with a thickness of about 1.0 μm on an about 300 μm thick aluminum plate so that a charge generating layer was formed on the aluminum plate.

A charge transporting layer coating liquid was prepared by mixing and dispersing the following components:

|  | Parts by Weight |
|---|---|
| Aminobiphenyl compound No. 2-2 in Table 3 | 2 |
| Polyester resin (Polyester Adhesive 49000 made by Du Pont Co.) | 3 |
| Tetrahydrofuran | 45 |

The thus prepared charge transporting layer coating liquid was coated on the aforementioned selenium charge generating layer by a doctor blade, dried at room temperature and further dried under reduced pressure, so that a charge transporting layer about 10 μm thick was formed on the charge generating layer; thus, an electrophotographic photoconductor No. 2-50 according to the present invention was prepared.

EXAMPLE P-2-57

A perylene pigment C.I. Vat Red 23 (C.I. 71130) of the following formula was vacuum-evaporated with a thickness of about 0.3 μm on an about 300 μm thick aluminum plate so that a charge generating layer was formed on the aluminum plate:

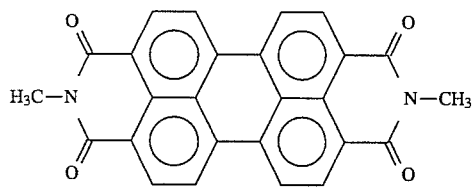

A charge transporting layer coating liquid was prepared by mixing and dispersing the following components:

|  | Parts by Weight |
|---|---|
| Aminobiphenyl compound No. 2-2 in Table 3 | 2 |
| Polyester resin (Polyester Adhesive 49000 made by Du Pont Co.) | 3 |
| Tetrahydrofuran | 45 |

The thus prepared charge transporting layer coating liquid was coated on the aforementioned charge generating layer by a doctor blade, dried at room temperature and further dried under reduced pressure, so that a charge transporting layer about 10 μm thick was formed on the charge generating layer; thus, an electrophotographic photoconductor No. 2-51 according to the present invention was prepared.

EXAMPLE P-2-58

One part by weight of Diane Blue (C.I. Pigment Blue 25, C.I. 21180) which was the same as that employed in Example P-2-1 was added to 158 parts by weight of tetrahydrofuran, and the mixture was ground and dispersed in a ball mill. To this mixture, 12 parts by weight of the aminobiphenyl compound No. 2-2 in Table 3 and 18 parts by weight of a polyester resin (Polyester Adhesive 49000 made by Du Pont Co.) were added and mixed, whereby a photoconductive layer coating liquid was prepared.

The thus prepared photoconductive layer coating liquid was coated on an aluminum-evaporated polyester film by a doctor blade and dried at 100° C. for 30 minutes, so that a photoconductive layer with a thickness of about 16 μm was formed on the aluminum-evaporated polyester film, thus, an electrophotographic photoconductor No. 2-52 according to the present invention was prepared.

EXAMPLE P-2-59

The same charge transporting layer coating liquid as that prepared in Example P-2-1 was coated by a doctor blade on the aluminum-evaporated surface of an aluminum-evaporated polyester base film, which served as an electroconductive support, so that a charge transporting layer was formed on the electroconductive support, with a thickness of about 20 μm when dried at room temperature.

Then the following components were ground and dispersed in a ball mill to prepare a dispersion:

|  | Parts by Weight |
| --- | --- |
| Bisazo Pigment (a charge generating pigment of the following formula (CG-5)) | 13.5 |

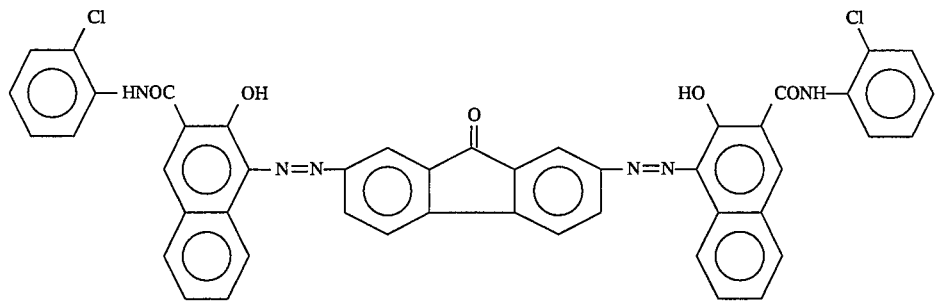

|  |  |
| --- | --- |
| Polyvinyl butyral (Trademark "XYHL" made by Union Carbide Plastic Co., Ltd.) | 5.4 |
| Tetrahydrofuran | 680 |
| Ethyl cellosolve | 1020 |

To the above dispersion, 1700 parts by weight of ethyl cellosolve were further added and the mixture was dispersed, whereby a charge generating layer coating liquid was prepared.

The thus prepared charge generating layer coating liquid was coated on the aforementioned charge transporting layer by spray coating and dried at 100° C. for 10 minutes, whereby a charge generating layer having a thickness of about 0.2 μm was formed on the charge transporting layer.

Then a methanol/n-buthanol solution of a polyaminde resin (Trademark "CM-8000" made by Toray Industries, Inc.) was coated on the charge generating layer by spray coating and dried at 120° C. for 30 minutes, whereby a protective layer having a thickness of about 0.5 μm was formed on the charge generating layer. Thus an electrophotographic photoconductor No. 2-59 according to the present invention was prepared.

The thus prepared electrophotographic photoconductors No. 2-2 to No. 2-59 were charged negatively or positively in the dark under application of −6 kV or +6 kV of corona charge for 20 seconds and then allowed to stand in the dark for 20 seconds without applying any charge thereto. At this moment, the surface potential $V_{po}$ (V) of each photoconductor was measured by a Paper Analyzer (Kawaguchi Electro Works, Model SP-428). Each photoconductor was then illuminated by a tungsten lamp in such a manner that the illuminance on the illuminated surface of the photoconductor was 20 lux, so that the exposure $E_{1/2}$ (lux.seconds) required to reduce the initial surface potential $V_{po}$ (V) to ½ the initial surface potential $V_{po}$ (V) was measured.

The results are shown in Table 8.

TABLE 8

| Photoconductors | Vpo (volt) | $E_{1/2}$ (lux · sec) |
| --- | --- | --- |
| No. 2-1 | −1113 | 1.72 |
| No. 2-2 | −1230 | 1.51 |
| No. 2-3 | −1311 | 1.02 |
| No. 2-4 | −1530 | 2.42 |
| No. 2-5 | −1185 | 0.93 |
| No. 2-6 | −975 | 0.92 |

TABLE 8-continued

| Photoconductors | Vpo (volt) | $E_{1/2}$ (lux · sec) |
| --- | --- | --- |
| No. 2-7 | −1250 | 2.01 |
| No. 2-8 | −1412 | 1.85 |
| No. 2-9 | −1080 | 1.31 |
| No. 2-10 | −1162 | 0.99 |
| No. 2-11 | −1151 | 0.95 |
| No. 2-12 | −1247 | 0.93 |
| No. 2-13 | −1189 | 0.91 |
| No. 2-14 | −1208 | 0.99 |
| No. 2-15 | −1058 | 0.86 |
| No. 2-16 | −1278 | 0.97 |
| No. 2-17 | −1102 | 0.90 |
| No. 2-18 | −1310 | 1.03 |
| No. 2-19 | −1264 | 1.00 |
| No. 2-20 | −1380 | 1.04 |
| No. 2-21 | −1364 | 1.02 |
| No. 2-22 | −1146 | 1.05 |
| No. 2-23 | −1262 | 1.29 |
| No. 2-24 | −1303 | 1.03 |
| No. 2-25 | −1190 | 0.95 |
| No. 2-26 | −1154 | 0.97 |
| No. 2-27 | −1030 | 0.85 |
| No. 2-28 | −1313 | 1.01 |
| No. 2-29 | −1180 | 0.91 |
| No. 2-30 | −1158 | 0.98 |
| No. 2-31 | −1140 | 0.96 |
| No. 2-32 | −1157 | 0.98 |
| No. 2-33 | −1050 | 0.87 |
| No. 2-34 | −1305 | 1.01 |
| No. 2-35 | −1180 | 0.94 |
| No. 2-36 | −1304 | 1.00 |
| No. 2-37 | −1156 | 0.92 |
| No. 2-38 | −1330 | 1.03 |
| No. 2-39 | −1193 | 0.94 |
| No. 2-40 | −1330 | 1.03 |
| No. 2-41 | −1195 | 0.94 |
| No. 2-42 | −1190 | 0.99 |
| No. 2-43 | −1145 | 0.98 |
| No. 2-44 | −1380 | 1.03 |
| No. 2-45 | −1360 | 1.01 |
| No. 2-46 | −1280 | 1.02 |
| No. 2-47 | −1258 | 0.98 |
| No. 2-48 | −1233 | 1.01 |
| No. 2-49 | −1155 | 0.99 |
| No. 2-50 | −1250 | 0.98 |
| No. 2-51 | −1213 | 0.97 |

TABLE 8-continued

| Photoconductors | Vpo (volt) | $E_{1/2}$ (lux · sec) |
|---|---|---|
| No. 2–52 | −1315 | 1.04 |
| No. 2–53 | −1290 | 1.02 |
| No. 2–54 | −1304 | 1.02 |
| No. 2–55 | −1232 | 0.99 |
| No. 2–56 | −953 | 2.59 |
| No. 2–57 | −1450 | 3.80 |
| No. 2–58 | +1302 | 1.85 |
| No. 2–59 | +1315 | 0.97 |

Each of the above electrophotographic photoconductors No. 2-1 through No. 2-59 was incorporated in a commercially available electrophotographic copying machine and a latent electrostatic image was formed thereon by being exposed to a light image. The latent electrostatic image was developed with a dry type developer to a visible toner image, electrostatically transferred to a transfer sheet made of plain paper and fixed thereto. As a result, a clear transferred image was obtained by each of the photoconductors. When a liquid developer was employed instead of the dry type developer, clear transfer images were obtained likewise.

EXAMPLE P-2-60

The following components were ground and dispersed in a ball mill to prepare a charge generating layer coating liquid:

| | Parts by Weight |
|---|---|
| Bisazo Pigment (a charge generating pigment of the following formula (CG-5) | 7.5 |

| | |
|---|---|
| 0.5% tetrahydrofuran solution of a polyester resin (Trademark "Vylon 200" made by Toyobo Co., Ltd.) | 500 |

The thus prepared charge generating layer coating liquid was coated by a doctor blade on the aluminum-evaporated surface of an aluminum-evaporated polyester base film, which served as an electroconductive support, so that a charge generating layer was formed with a thickness of about 1 μm on the electroconductive support when dried at room temperature.

Then the following components were mixed and dissolved, so that a charge transporting layer coating liquid was prepared:

| | Parts by Weight |
|---|---|
| Aminobiphenyl compound No. 2-2 in Table 3 | 1 |
| Polycarbonate resin (Trademark "Panlite K-1300" made by Teijin Limited.) | 1 |
| Tetrahydrofuran | 8 |

The thus prepared charge transporting layer coating liquid was coated on the aforementioned charge generating layer by a doctor blade and dried at 80° C. for 2 minutes and then at 105° C. for 5 minutes, so that a charge transporting layer with a thickness of about 20 μm was formed on the charge generating layer. Thus, an electrophotographic photoconductor No. 2-60 according to the present invention was prepared.

The thus prepared electrophotographic photoconductor No. 2-60 was charged negatively in the dark under application of −6 kV of corona charge for 20 seconds and the initial surface potential Vm(V) of the photoconductor was measured by a Paper Analyzer (Kawaguchi Electro Works, Model SP-428). The photoconductor was then allowed to stand in the dark for 20 seconds without applying any charge thereto. At this moment, the surface potential $V_{po}$ (V) after dark decay of the photoconductor was measured by the Paper Analyzer. The photoconductor was then illuminated by a tungsten lamp in such a manner that the illuminance on the illuminated surface of the photoconductor was 4.5 lux, and the exposure $E_{1/2}$ (lux.seconds) required to reduce the initial surface potential $V_{po}$ (V) to ½ the initial surface potential $V_{po}$ (V) was measured. Furthermore, the residual surface potential Vr(V) when exposed to the light for 30 seconds was measured. The results showed that Vm=−1358 V, $V_{po}$ (V)=−1185 V, $E_{1/2}$=0.93 lux.seconds, and Vr=0 V. The charge transporting layer was transparent.

EXAMPLE P-2-61

Example P-2-60 was repeated except that Aminobiphenyl Compound No. 2-2 employed in the charge transporting layer in Example P-2-60 was replaced by Aminobiphenyl Compound No. 2-104 in Table 3, whereby an electrophotographic photoconductor No. 2-61 according to the present invention was prepared.

The initial surface potential Vm(V), the surface potential $V_{po}$ (V) after dark decay, the exposure $E_{1/2}$ (lux.seconds), and the residual potential Vr(V) of this electrophotographic photoconductor were measured in the same manner as in Example P-1-6i. The results showed that Vm= –1522 V, $V_{po}$ (V)=–1364 V, $E_{1/2}$=1.02 lux.seconds, and Vr= 0 V. The charge transporting layer was transparent.

COMPARATIVE Example P-1

Example P-2-60 was repeated except that Aminobiphenyl Compound No. 1-2 employed as the charge transporting material in Example P-2-60 was replaced by 4,4',4"-trimethyltriphenylamine of the following formula, whereby a comparative electrophotographic photoconductor No. 1 was prepared.

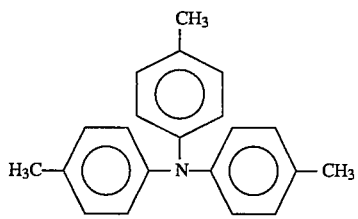

The initial surface potential Vm(V), the surface potential $V_{po}$ (V) after dark decay, the exposure $E_{+c,fra\ +ec}$ (lux.seconds), and the residual potential Vr(V) of this comparative electrophotographic photoconductor were measured in the same manner as in Example P-2-60. The results showed that Vm=–1480 V, $V_{po}$ (V)=–1290 V, $E_{1/2}$=1.24 lux.seconds, and Vr=–130 V. The charge transporting layer was milky white. These results indicate that the photosensitivity of this comparative photoconductor represented by $E_{1/2}$ is lower than those of the above-mentioned electrophotographic photoconductors No. 2-60 and No. 2-61 according to the present invention and the residual potential Vr(V) is higher than those of the electrophotographic photoconductors No. 2-60 and No. 2-61 according to the present invention.

COMPARATIVE EXAMPLE P-2

Example P-2-5 was repeated except that Aminobiphenyl Compound No. 1-2 employed as the charge transporting material in Example P-2-60 was replaced by 4,4',4"-trimethyltriphenylamine, whereby a comparative electrophotographic photoconductor No. 2 was prepared.

The surface potential $V_{po}$ (V) after dark decay, the exposure $E_{1/2}$ (lux.seconds), and the residual potential Vr(V) of this comparative electrophotographic photoconductor were measured in the same manner as in Example P-2-5. The results showed that $V_{po}$ (V)=–1290 V, $E_{1/2}$=1.24 lux.seconds, and Vr= –130 V. The charge transporting layer was milky white.

In the case of the electrophotographic photoconductor No. 2-5 in Example P-2-5, $V_{po}$ (V)=–1185 V, $E_{1/2}$=0.93 lux.seconds, and Vr=0 V. Thus, the photosensitivity of this comparative photoconductor represented by $E_{1/2}$ is lower than that of the electrophotographic photoconductor No. 2-5 according to the present invention and the residual potential (Vr) is higher than that of the photographic photoconductor No. 1-5 according no the present invention.

COMPARATIVE EXAMPLE P-3

The following components were ground and dispersed in a ball mill to prepare a charge generating layer coating liquid:

| | Parts by Weight |
|---|---|
| Bisazo pigment (charge generating material (CG-5)) | 76 |
| 2% tetrahydrofuran solution of a polyester resin (Trademark "Vylon 200" made by Toyobo Co., Ltd.) | 1,260 |
| Tetrahydrofuran | 3,700 |

This charge generating layer coating liquid was coated by a doctor blade on the aluminum-evaporated surface of an aluminum-evaporated polyester base film, which served as an electroconductive support, so that a charge generating layer was formed on the electroconductive support with a thickness of about 1 µm when dried at room temperature. Then the following components were mixed and dissolved, so that a charge transporting layer coating liquid was prepared:

| | Parts by Weight |
|---|---|
| N,N-diphenyl-[1,1'-biphenyl]-4-amine of the following formula serving as | 2 |

|  | Parts by Weight |
|---|---|
| charge transporting material: | 5 |
| 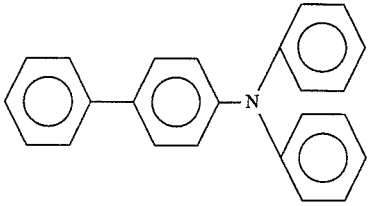 | |
| Polycarbonate resin (Trademark "Panlite K-1300" made by Teijin Limited.) | 2 |
| Tetrahydrofuran | 16 |

The thus prepared charge transporting layer coating liquid was coated on the aforementioned charge generating layer by a doctor blade and dried at 80 °C. for 2 minutes and then at 105° C. for 5 minutes, so that a charge transporting layer with a thickness of about 20 μm was formed on the charge generating layer, whereby a comparative electrophotographic photoconductor No. 3 was prepared.

COMPARATIVE EXAMPLE P-4

Comparative Example P-3 was repeated except that N,N-diphenyl-[1,1'-biphenyl]-4-amine employed as charge transporting material in Comparative Example P-3 was replaced by 4,4',4''-trimethyltriphenylamine, whereby a comparative electrophotographic photoconductor No. 4 was prepared.

The thus prepared comparative electrophotographic photoconductors No. 3 and No. 4 were charged negatively in the dark under application of −6 kV of corona charge for 20 seconds and then allowed to stand in the dark for 20 seconds without applying any charge thereto. At this moment, the surface potential $V_{po}$ (V) of each photoconductor was measured by a Paper Analyzer (Kawaguchi Electro Works, Model SP-428). Each photoconductor was then illuminated by a tungsten lamp in such a manner that the illuminance on the illuminated surface of the photoconductor was 20 lux, so that the exposure $E_{1/2}$ (lux.seconds) required to reduce the initial surface potential $V_{po}$ (V) to ½ the initial surface potential $V_{po}$ (V) was measured.

Furthermore, the surface potential of each comparative electrophotoconductor 30 seconds after the initiation of the exposure to the light was also measured, which surface potential is referred to as Vr. For comparison $V_{po}$ (V) $E_{1/2}$ lux.second) and Vr (V) of Photoconductor No. 1-5 prepared in Example P-1-5 were also measured in the same manner.

The results are shown in the following Table 9:

TABLE 9

|  | Vpo (V) | $E_{1/2}$ | Vr (V) |
|---|---|---|---|
| Photoconductor No. 1–5 comparative | 1190 | 0.62 | –0 |
| Photoconductor No. 3 Comparative | −1363 | 1.30 | 0 |
| Photoconductor No. 4 | −1290 | 1.24 | −129 |

In order to investigate the fatigue characteristics of Photoconductor No. 1-5 and Comparative Photoconductor No. 3 after repeated use (hereinafter referred to as the repeated-use fatigue characteristics), the two photoconductors were subjected to the charging at −7.5 kV and exposure of 30 lux in repetition, so that the changes in the residual surface potential (Vr') of each photoconductor were measured. The results are shown in FIG. 18.

The results shown in Table 9 and in FIG. 18 indicate that Comparative Photoconductor No. 3 is inferior to Photoconductor No. 1-5 in $E_{1/2}$ which represents photosensitivity, and the residual surface potential of Comparative Photoconductor No. 3 increases while in repeated use. Comparative Photoconductor No. 4 is also lower in $E_{1/2}$ than Photoconductor No. 1-5, and has a relatively high residual potential (Vr) in the initial stage before its repeated use.

What is claimed is:

1. A charge transporting material, comprising one or more compounds having the formula (I):

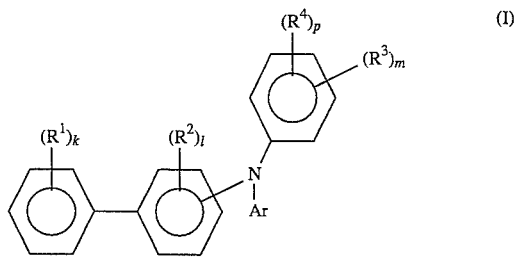

wherein $R^1$ represents hydrogen; an unsubstituted or substituted alkyl group; an alkoxyl group having 1 to 4 carbon atoms; a thioalkoxyl group having 1 to 4 carbon atoms; an aryloxy group; an aralkyl group; a nitro group; an unsubstituted or substituted aryl group; a halogen; an amino group; an unsubstituted or substituted dialkylamino group; $R^2$ represents hydrogen; an unsubstituted or substituted alkyl group; an alkoxyl group having 1 to 4 carbon atoms; or a halogen; $R^3$ represents hydrogen; an alkyl group having 1 to 4 carbon atoms; an alkoxyl group having 1 to 4 carbon atoms; a halogen; a dialkylamino group; an amino group; a thioalkoxyl group having 1 to 4 carbon atoms; an aryloxy group; a methylenedioxy group; an aralkyl group; or an unsubstituted or substituted aryl group; $R^4$ represents hydrogen; an unsubstituted or substituted alkyl group; an alkoxyl group; or a halogen; Ar represents an unsubstituted or substituted monocyclic hydrocarbon group, non-condensed polycyclic hydrocarbon group or heterocyclic group; k is an integer of 0 to 5, l is an integer of 0 to 4, and (p+m) is 0 to 5, provided that when Ar is an unsubstituted phenyl group, $R^1$, $R^2$, $R^3$, and $R^4$ cannot be hydrogen at the same time.

2. The charge transporting material as claimed in claim 1, wherein said alkyl group represented by $R^1$ in formula (I) is an alkyl group having 1 to 4 carbon atoms.

3. The charge transporting material as claimed in claim 1, wherein said aryloxy group represented by $R^1$ is selected from the group consisting of a phenoxy group and a naphthoxy group.

4. The charge transporting material as claimed in claim 1, wherein said aralkyl group represented by $R^1$ is $C_6H_5(CH_2)_n-$, where n is 1 to 4.

5. The charge transporting material as claimed in claim 1, wherein said unsubstituted or substituted aryl group represented by $R^1$ is selected from the group consisting of a phenyl group and a naphthyl group which may have a substituent selected from the group consisting of an alkyl group having 1 to 4 carbon atoms and an alkoxyl group having 1 to 4 carbon atoms.

6. The charge transporting material as claimed in claim 1, wherein said alkyl group represented by $R^2$ is an alkyl group having 1 to 4 carbon atoms.

7. The charge transporting material as claimed in claim 1, wherein said aryloxy group represented by $R^3$ is selected from the group consisting of a phenoxy group and a naphthoxy group.

8. The charge transporting material as claimed in claim 1, wherein said aralkyl group represented by $R^3$ is $C_6H_5(CH_2)_n-$, where n is 1 to 4.

9. The charge transporting material as claimed in claim 1, wherein said unsubstituted or substituted aryl group represented by $R^3$ is selected from the group consisting of a phenyl group and a naphthyl group which may have a substituent selected from the group consisting of an amino group, an unsubstituted or substituted dialkylamino group, an alkoxyl group, a thioalkyl group, an aryloxy group, an unsubstituted or substituted alkyl group, an alkoxyl group having 1 to 4 carbon atoms, and a halogen.

10. The charge transporting material as claimed in claim I, wherein said alkoxyl group represented by $R^4$ is an alkoxyl group having 1 to 4 carbon atoms.

11. The charge transporting material as claimed in claim 1, wherein said alkyl group represented by $R^4$ is an alkyl group having 1 to 4 carbon atoms.

12. The charge transporting material as claimed in claim 1, wherein Ar in formula (I) is

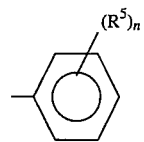

wherein $R^5$ represents hydrogen; an unsubstituted or substituted alkyl group; an alkoxyl group having 1 to 4 carbon atoms; a thioalkoxyl group having 1 to 4 carbon atoms; an aryloxy group; a methylenedioxy group; an aralkyl group; a nitro group; an unsubstituted or substituted aryl group; a halogen; or an amino group; or an unsubstituted or substituted dialkylamino group.

13. The charge transporting material as claimed in claim 12, wherein said alkyl group represented by $R^5$ is an alkyl group having 1 to 4 carbon atoms.

14. The charge transporting material as claimed in claim 12, wherein said aryloxy group represented by $R^5$ is selected from the group consisting of a phenoxy group and a naphthoxy group.

15. The charge transporting material as claimed in claim 12, wherein said aralkyl group represented by $R^5$ is $C_6H_5(CH_2)_n-$ where n is 1 to 4.

16. The charge transporting material as claimed in claim 12, wherein said unsubstituted or substituted aryl group is selected from the group consisting of a phenyl group and a naphthyl group, which may have as a substituent an alkyl group having 1 to 4 carbon atoms or an alkoxyl group having 1 to 4 carbon atoms.

17. A charge transporting material, comprising one or more compounds having the formula (I-1):

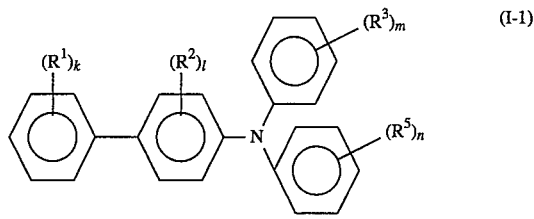

wherein $R^1$ represents hydrogen, an alkyl group having 1 to 4 carbon atoms, an alkoxyl group having 1 to 4 carbon atoms, a thioalkoxyl group, an aryloxy group, a methylenedioxy group, an aralkyl group, a nitro group, or an unsubstituted or substituted aryl group; $R^2$ represents hydrogen, an alkyl group having 1 to 4 carbon atoms, an alkoxyl group having 1 to 4 carbon atoms, a halogen; and $R^3$ and $R^5$ each represent hydrogen, an alkyl group having 1 to 4 carbon atoms, an alkoxyl group having 1 to 4 carbon atoms, a halogen, a dialkylamino group, an amino group, a thioalkoxyl group, an aryloxy group, a methylenedioxy group, an aralkyl group, or an unsubstituted or substituted aryl group, k, m and n are each independently an integer of 0 to 5, and l is an integer of 0 to 4, provided that $R^1$, $R^2$, $R^3$ and $R^5$ cannot be hydrogen at the same time.

18. The charge transporting material as claimed in claim 17, having the formula (I-1):

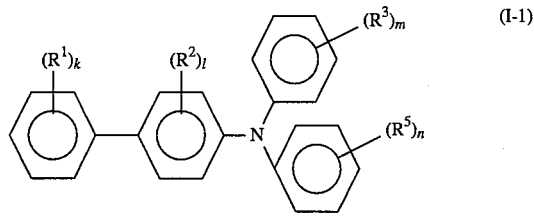

wherein $R^1$, $R^2$, $R^3$, and $R^5$ each represent hydrogen, an alkyl group having 1 to 4 carbon atoms, or an alkoxyl group having 1 to 4 carbon atoms, k, m and n are each independently an integer of 0 to 5, and l is an integer of 0 to 4, provided that $R^1$, $R^2$, $R^3$ and $R^5$ cannot be hydrogen at the same time.

19. An electrophotographic photoconductor comprising an electroconductive support and a photoconductive layer formed thereon comprising at least one aminobiphenyl compound having formula:

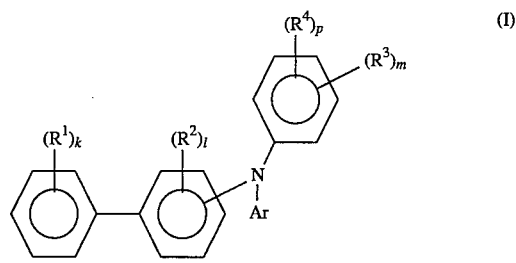

wherein $R^1$ represents hydrogen; an unsubstituted or substituted alkyl group; an alkoxyl group having 1 to 4 carbon atoms; a thioalkoxyl group having 1 to 4 carbon atoms; an aryloxy group; an aralkyl group; a nitro group; an unsubstituted or substituted aryl group; a halogen; an amino group; an unsubstituted or substituted dialkylamino group; $R^2$ represents hydrogen; an unsubstituted or substituted alkyl group; an alkoxyl group having 1 to 4 carbon atoms; or a halogen; $R^3$ represents hydrogen; an alkyl group having 1 to 4 carbon atoms; an alkoxyl group having 1 to 4 carbon atoms; a halogen; a dialkylamino group; an amino group; a thioalkoxyl group having 1 to 4 carbon atoms; an aryloxy group; a methylenedioxy group; an aralkyl group; or an unsubstituted or substituted aryl group; $R^4$ represents hydrogen; an unsubstituted or substituted alkyl group; an alkoxyl group; or a halogen; Ar represents an unsubstituted or substituted monocyclic hydrocarbon group, non-condensed polycyclic hydrocarbon group or heterocyclic group; k is an integer of 0 to 5, l is an integer of 0 to 4, and (p+m) is 0 to 5, provided that when Ar is an unsubstituted phenyl group, $R^1$, $R^2$, $R^3$, and $R^4$ cannot be hydrogen at the same time.

20. The electrophotographic photoconductor as claimed in claim 19, wherein said photoconductive layer further comprises a binder agent which constitutes a charge transporting medium in combination with said aminobiphenyl compound; and a charge generating material dispersed within said charge transporting medium.

21. The electrophotographic photoconductor as claimed in claim 19, wherein said photoconductive layer comprises a charge generating layer containing a charge generating material and a charge transporting layer containing said aminobiphenyl compound as a charge transporting material.

22. The electrophotographic photoconductor as claimed in claim 19, wherein the amount of said aminobiphenyl compound is in the range of 30 wt. % to 70 wt. % of the entire weight of said photoconductive layer.

23. The electrophotographic photoconductor as claimed in claim 20, wherein the amount of said aminobiphenyl compound is in the range of 10 wt. % to 95 wt. % of the entire weight of said photoconductive layer, and the amount of said charge generating material is in the range of 0.1 wt. % to 50 wt. % of the entire weight of said photoconductive layer.

24. The electrophotographic photoconductor as claimed in claim 21, wherein the amount of said charge generating material is in the range of 10 wt. % to 95 wt. % of the entire weight of said charge generating layer, and the amount of said aminobiphenyl compound is in the range of 10 wt. % to 95 wt. % of the entire weight of said photoconductive layer.

25. An electrophotographic photoconductor comprising an electroconductive support and a photoconductive layer formed thereon comprising at least one aminobiphenyl compound having formula:

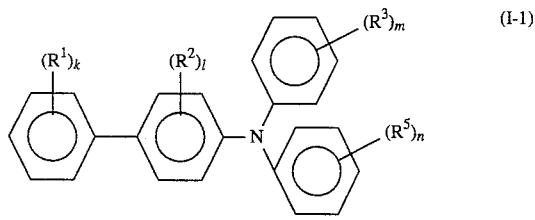

(I-1)

wherein $R^1$ represents hydrogen, an alkyl group having 1 to 4 carbon atoms, an alkoxyl group having 1 to 4 carbon atoms, a thioalkoxyl group, an aryloxy group, a methylenedioxy group, an aralkyl group, a nitro group, or an unsubstituted or substituted aryl group; $R^2$ represents hydrogen, an alkyl group having 1 to 4 carbon atoms, an alkoxyl group having 1 to 4 carbon atoms, a halogen; and $R^3$ and $R^5$ each represent hydrogen, an alkyl group having 1 to 4 carbon atoms, an alkoxyl group having 1 to 4 carbon atoms, a halogen, a dialkylamino group, an amino group, a thioalkoxyl group, an aryloxy group, a methylenedioxy group, an aralkyl group, or an unsubstituted or substituted aryl group, k, m and n are each independently an integer of 0 to 5, and l is an integer of 0 to 4, provided that $R^1$, $R^2$, $R^3$ and $R^5$ cannot be hydrogen at the same time.

26. The electrophotographic photoconductor as claimed in claim 25, wherein said aminobiphenyl compound has the formula

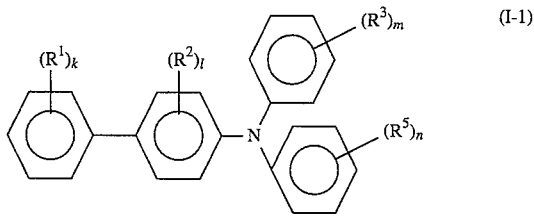

(I-1)

wherein $R^1$, $R^2$, $R^3$, and $R^5$ each represent hydrogen, an alkyl group having 1 to 4 carbon atoms, or an alkoxyl group having 1 to 4 carbon atoms, k, m and n are each independently an integer of 0 to 5, and l is an integer of 0 to 4, provided that $R^1$, $R^2$, $R^3$ and $R^5$ cannot be hydrogen at the same time.

27. The electrophotographic photoconductor as claimed in claim 25, wherein said photoconductive layer further comprises a binder agent which constitutes a charge transporting medium in combination with said aminibiphenyl compound; and a charge generating material dispersed within said charge transporting medium.

28. The electrophotographic photoconductor as claimed in claim 25, wherein said photoconductive layer comprises a charge generating layer containing a charge generating material and a charge transporting layer containing said aminobiphenyl compound as a charge transporting material.

29. The electrophotographic photoconductor as claimed in claim 25, wherein the amount of said aminibiphenyl compound is in the range of 30 wt. % to 70 wt. % of the entire weight of said photoconductive layer.

30. The electrophotographic photoconductor as claimed in claim 27, wherein the amount of said aminobiphenyl compound is in the range of 10 wt. % to 95 wt. % of the entire weight of said photoconductive layer, and the amount of said charge generating material is in the range of 0.1 wt. % to 50 wt. % of the entire weight of said photoconductive layer.

31. The electrophotographic photoconductor as claimed in claim 28, wherein the amount of said charge generating material is in the range of 10 wt. % to 95 wt. % of the entire weight of said charge generating layer, and the amount of said aminobiphenyl compound is in the range of 10 wt. % to 95 wt. % of the entire weight of said photoconductive layer.

32. The electrophotographic photoconductor as claimed in claim 26, wherein said photoconductive layer further comprises a binder agent which constitutes a charge transporting medium in combination with said aminibiphenyl compound; and a charge generating material dispersed within said charge transporting medium.

33. The electrophotographic photoconductor as claimed in claim 26, wherein said photoconductive layer comprises a charge generating layer containing a charge generating material and a charge transporting layer containing said aminobiphenyl compound as a charge transporting material.

34. The electrophotographic photoconductor as claimed in claim 26, wherein the amount of said aminibiphenyl compound is in the range of 30 wt. % to 70 wt. % of the entire weight of said photoconductive layer.

35. The electrophotographic photoconductor as claimed in claim 32, wherein the amount of said aminobiphenyl compound is in the range of 10 wt. % to 95 wt. % of the entire weight of said photoconductive layer, and the amount of said charge generating material is in the range of 0.1 wt.

% to 50 wt. % of the entire weight of said photoconductive layer.

36. The electrophotographic photoconductor as claimed in claim 33, wherein the amount of said charge generating material is in the range of 10 wt. % to 95 wt. % of the entire weight of said charge generating layer, and the amount of said aminobiphenyl compound is in the range of 10 wt. % to 95 wt. % of the entire weight of said photoconductive layer.

37. The electrophotographic photoconductor as claimed in claim 25, wherein said photoconductive layer has a thickness in the range of 3–50 μm.

38. The electrophotographic photoconductor as claimed in claim 37, wherein said photoconductive layer has a thickness in the range of 5–10 μm.

39. The electrophotographic photoconductor as claimed in claim 25, wherein said photoconductive layer contains a sensitizer dye in the amount of 0.1 to 5 wt. % of the total weight.

40. The electrophotographic photoconductor as claimed in claim 28, wherein said charge generating layer has a thickness of 5 μm or less, and said charge transporting layer has a thickness of about 3–50 μm.

41. The electrophotographic photoconductor as claimed in claim 25, which further comprises an adhesive or barrier layer between said electroconductive layer and said photoconductive layer, said adhesive or barrier layer having a thickness of 1 μm or less.

* * * * *

UNITED STATES PATENT AND TRADEMARK OFFICE
CERTIFICATE OF CORRECTION

PATENT NO. : 5,462,826
DATED : October 31, 1995
INVENTOR(S) : Tomoyuki SHIMADA, et al.

It is certified that error appears in the above-identified patent and that said Letters Patent is hereby corrected as shown below:

Column 1, line 58, "belt flue" should read --belt due--;
    line 59, "vulnerable no bean" should read --vulnerable to heat--.

Column 2, line 63, insert "of" before "unclear".

Column 3, line 58, "atoms: or" should read --atoms; or--.

Column 4, line 50, "and 1 may represent and integer" should read --and $\ell$ may represent an integer--.

Column 5, line 8, "as alphenyl" should read --as a phenyl--;
    line 19, ":group" should read --group--.

UNITED STATES PATENT AND TRADEMARK OFFICE
CERTIFICATE OF CORRECTION

PATENT NO. : 5,462,826
DATED : October 31, 1995
INVENTOR(S) : Tomoyuki SHIMADA, et al.

It is certified that error appears in the above-identified patent and that said Letters Patent is hereby corrected as shown below:

Column 6, line 32, "The aminobipheny" should read
--The aminobiphenyl--.

line 37, "presence finely-divided" should read
--presence of (c) finely-divided--.

Column 10, line 24, product Was" should read
--product was--.

line 61, "mixture Was" should read
--mixture was--.

Column 11, line 16, "4-methyl-4'N,N-bis(4-methylphenly) aminobiphenyl" should read --4-methyl-4'-N,N-bis (4-methylphenyl)aminobiphenyl--.

Column 42, line 25, "elementals" should read
--elemental--.

line 39, "of the aove" should read
--of the above--.

line 40, "a Far tablet" should read
--A KBr tablet--.

UNITED STATES PATENT AND TRADEMARK OFFICE
CERTIFICATE OF CORRECTION

PATENT NO. : 5,462,826
DATED : October 31, 995
INVENTOR(S) : Tomoyuki SHIMADA, et al.

It is certified that error appears in the above-identified patent and that said Letters Patent is hereby corrected as shown below:

Column 47, line 6, "medium accepts" should read
--medium 4 accepts--.

Column 50, line 38, "uniformly charge" should read
--uniformly charged--.

Column 51, line 40, "Polycarbon" should read
--Polycarbonate--.

Column 52, line 34, ":surface" should read --surface--.

Column 57, line 32 "With" should read --with--.

Column 58, line 20, "$E_{1/2}$ (lux seconds)" should read
--$E_{1/2}$ (lux•seconds)--.

Column 60, line 20 "As=a result" should read
--As a result--;
    line 56, "dried an room" should read
--dried at room--.

UNITED STATES PATENT AND TRADEMARK OFFICE
CERTIFICATE OF CORRECTION

PATENT NO. : 5,462,826
DATED : October 31, 1995
INVENTOR(S) : Tomoyuki SHIMADA, et al.

It is certified that error appears in the above-identified patent and that said Letters Patent is hereby corrected as shown below:

Column 60, line 65, "in Table 13" should read
--in Table 3--.

Column 62, line 4, "$E_{1/2}$ (lux seconds)" should read
--$E_{1/2}$ (lux•seconds)--.

Column 67, line 35, "polyaminde" should read
--polyamide--.

Column 71, line 5, "Example P-1-6i." should read
--Example P-2-61.--.
   line 53, "$E_{+e,fra\ +cc}$(lux.seconds" should read
--$E_{1/2}$(lux•seconds)--.

Column 72, line 22, "No. 1-5" should read --No. 2-5--;
   line 58, start new ¶, "Then the following".

Column 75, line 21, "I, wherein" should read
--1, wherein--.

UNITED STATES PATENT AND TRADEMARK OFFICE
CERTIFICATE OF CORRECTION

PATENT NO. : 5,462,826
DATED : October 31, 1995
INVENTOR(S) : Tomoyuki SHIMADA, et al.

It is certified that error appears in the above-identified patent and that said Letters Patent is hereby corrected as shown below:

Column 78, line 23, "aminibiphenyl" should read --aminobiphenyl--;

line 32, "aminibiphenyl" should read --aminobiphenyl--;

line 51, "aminibiphenyl" should read --aminobiphenyl--;

line 60, "aminibiphenyl" should read --aminobiphenyl--.

Signed and Sealed this

Thirty-first Day of March, 1998

Attest:

BRUCE LEHMAN

*Attesting Officer*  *Commissioner of Patents and Trademarks*